United States Patent [19]

Hogan, Jr.

[11] Patent Number: 5,981,467
[45] Date of Patent: Nov. 9, 1999

[54] AMINIMIDE-CONTAINING MOLECULES AND MATERIALS AS MOLECULAR RECOGNITION AGENTS

[75] Inventor: Joseph C. Hogan, Jr., Belmont, Mass.

[73] Assignee: Arqule, Inc., Medford, Mass.

[21] Appl. No.: 08/765,173

[22] Filed: Feb. 16, 1996

Related U.S. Application Data

[63] Continuation of application No. 08/204,206, Mar. 27, 1995, Pat. No. 5,705,585.

[51] Int. Cl.$^6$ ................................................ A61K 31/205
[52] U.S. Cl. ............................................................ 514/1
[58] Field of Search ...................................... 514/1

[56] References Cited

U.S. PATENT DOCUMENTS

| | | |
|---|---|---|
| 3,410,880 | 11/1968 | Brockenhurst . |
| 3,450,673 | 6/1969 | McKillip . |
| 3,485,806 | 12/1969 | Bloomquist et al. . |
| 3,488,327 | 1/1970 | Kollinsky et al. . |
| 3,488,389 | 1/1970 | McKillip . |
| 3,499,032 | 3/1970 | Clemens et al. . |
| 3,511,894 | 5/1970 | Markert . |
| 3,527,802 | 9/1970 | Slagel . |
| 3,555,095 | 1/1971 | Slagel . |
| 3,565,868 | 2/1971 | Sedor et al. . |
| 3,567,725 | 3/1971 | Grabowski et al. . |
| 3,583,950 | 6/1971 | Kollinsky et al. . |
| 3,598,790 | 8/1971 | Kollinsky et al. . |
| 3,641,145 | 2/1972 | Culbertson . |
| 3,664,990 | 5/1972 | Slagel . |
| 3,671,473 | 6/1972 | Sedor et al. . |
| 3,676,453 | 7/1972 | Pines et al. . |
| 3,704,128 | 11/1972 | Koda et al. . |
| 3,706,797 | 12/1972 | McKillip et al. . |
| 3,706,800 | 12/1972 | Hartlage et al. . |
| 3,715,343 | 2/1973 | Slagel et al. . |
| 3,728,387 | 4/1973 | Freis et al. . |
| 3,756,994 | 9/1973 | Culbertson . |
| 3,781,319 | 12/1973 | Wawzonek et al. . |
| 3,794,495 | 2/1974 | Ishihara et al. . |
| 3,803,220 | 4/1974 | Gasman . |
| 3,811,887 | 5/1974 | Ishihara et al. . |
| 3,818,065 | 6/1974 | Schoellkopf et al. . |
| 3,828,007 | 8/1974 | Throckmorton . |
| 3,850,969 | 11/1974 | Grimm et al. . |
| 3,893,974 | 7/1975 | Niino et al. . |
| 3,898,087 | 8/1975 | Brutchen et al. . |
| 3,904,749 | 9/1975 | McKillip . |
| 3,925,284 | 12/1975 | Carleton et al. . |
| 3,934,029 | 1/1976 | Kabara .................................... 424/320 |
| 3,934,031 | 1/1976 | Kabara .................................... 424/320 |
| 3,934,035 | 1/1976 | Kabara .................................... 424/320 |
| 3,946,131 | 3/1976 | Biefeld et al. ........................... 428/378 |
| 3,948,866 | 4/1976 | Pennewiss et al. . |
| 3,949,140 | 4/1976 | Biefeld et al. ........................... 428/378 |
| 3,963,703 | 6/1976 | Culbertson . |
| 3,963,776 | 6/1976 | Middleton . |
| 3,968,065 | 7/1976 | Morris et al. . |
| 3,969,298 | 7/1976 | Gasman . |
| 3,983,166 | 9/1976 | Samour . |
| 3,985,807 | 10/1976 | Grimm et al. . |
| 4,005,055 | 1/1977 | Miron et al. . |
| 4,016,340 | 4/1977 | Kolesinski et al. ...................... 526/7 |
| 4,022,623 | 5/1977 | Fitzgerald et al. . |
| 4,046,658 | 9/1977 | Brown . |
| 4,067,830 | 1/1978 | Kresta . |
| 4,070,348 | 1/1978 | Kriemer et al. . |
| 4,078,901 | 3/1978 | Sung et al. ................................ 44/64 |
| 4,080,206 | 3/1978 | Kolesinski et al. ........................ 96/29 |
| 4,097,444 | 6/1978 | Teige et al. . |
| 4,102,916 | 7/1978 | Falk . |
| 4,122,159 | 10/1978 | Madrange et al. ....................... 424/45 |
| 4,140,680 | 2/1979 | Sullivan ................................ 526/287 |
| 4,162,355 | 7/1979 | Tsibris .................................. 526/293 |
| 4,189,481 | 2/1980 | Kabara .............................. 424/248.54 |
| 4,212,905 | 7/1980 | Talbris ................................. 427/221 |
| 4,213,860 | 7/1980 | Tsibris . |
| 4,217,364 | 8/1980 | Kabara ................................. 424/320 |
| 4,260,705 | 4/1981 | Tsibris .................................. 525/330 |
| 4,280,008 | 7/1981 | Schoellkopf et al. ................... 548/301 |
| 4,304,705 | 12/1981 | Heilmann et al. ...................... 260/30.4 |
| 4,378,411 | 3/1983 | Heilmann et al. ...................... 428/500 |
| 4,424,272 | 1/1984 | Taylor ................................... 430/507 |
| 4,451,619 | 5/1984 | Heilmann et al. ...................... 525/379 |
| 4,485,236 | 11/1984 | Rasmussen et al. ..................... 544/69 |
| 4,548,981 | 10/1985 | Kolesinski et al. ..................... 524/555 |
| 4,563,467 | 1/1986 | Soler ..................................... 514/336 |
| 4,617,253 | 10/1986 | Taylor et al. ........................... 430/323 |
| 4,624,995 | 11/1986 | Katritzky et al. ....................... 525/452 |

(List continued on next page.)

FOREIGN PATENT DOCUMENTS

| | | |
|---|---|---|
| 0 185 493 | 6/1986 | European Pat. Off. . |
| 0 212 617 | 4/1987 | European Pat. Off. . |
| 63-17933 | 4/1988 | Japan . |
| 1 181 218 | 2/1970 | United Kingdom . |
| 1 265 163 | 3/1972 | United Kingdom . |
| 93/20935 | 10/1993 | WIPO . |

OTHER PUBLICATIONS

J. Org. Chem., vol. 41, No. 4, 1976, 715–716, "Acyl Migration in a 2–Hydroxylalkyl Aminimides", by Meir Asscher.

Biopolymers, vol. 17, 1693–1711 (1978), "Experimental Conformational Study of Two Peptides Containing a–Aminoisobutyric Acid. Crystal Structure of N–Acetyl–a–Aminoisobutyric Acid Methylamide" by A. Aubry et al.

Tetrahedron Letters No. 31, pp. 2691–2694, 1976, "Pyridines as Leaving Groups in Synthetic Transformations: Nucleophilic Displacements of Amino Groups, and Novel Preparations of Nitriles and Isocyanates", by J.B. Bapat et al.

(List continued on next page.)

*Primary Examiner*—Nathan M. Nutter
*Attorney, Agent, or Firm*—Pennie & Edmonds LLP

[57] ABSTRACT

The design and synthesis of novel aminimide-based molecular modules and the use of the modules in the construction of new molecules and fabricated materials is disclosed. The new molecules and fabricated materials are molecular recognition agents useful in the design and synthesis of drugs, and have applications in separations and materials science.

9 Claims, No Drawings

U.S. PATENT DOCUMENTS

| | | | |
|---|---|---|---|
| 4,645,711 | 2/1987 | Winslow | 428/355 |
| 4,667,012 | 5/1987 | Rasmussen et al. | 528/332 |
| 4,670,528 | 6/1987 | Taylor et al. | 526/263 |
| 4,695,608 | 9/1987 | Engler et al. | 525/308 |
| 4,705,824 | 11/1987 | Lin | 524/612 |
| 4,737,560 | 4/1988 | Heilmann et al. | 526/304 |
| 4,740,568 | 4/1988 | Katritzky et al. | 525/452 |
| 4,777,217 | 10/1988 | Rasmussen et al. | 525/279 |
| 4,777,276 | 10/1988 | Rasmussen et al. | 556/419 |
| 4,785,070 | 11/1988 | Rasmussen et al. | 528/73 |
| 4,816,554 | 3/1989 | Katritzksy et al. | 528/210 |
| 4,841,021 | 6/1989 | Katritzky et al. | 528/407 |
| 4,852,969 | 8/1989 | Babirad et al. | 350/96.34 |
| 4,871,824 | 10/1989 | Heilmann et al. | 526/304 |
| 4,874,822 | 10/1989 | Rasmussen et al. | 525/279 |
| 4,898,923 | 2/1990 | Katritzky et al. | 528/73 |
| 4,948,715 | 8/1990 | Hulme-Lowe et al. | 430/495 |
| 4,981,933 | 1/1991 | Fazio et al. | 526/260 |
| 5,013,795 | 5/1991 | Coleman et al. | 525/279 |
| 5,039,813 | 8/1991 | Fazio et al. | 548/228 |
| 5,066,559 | 11/1991 | Elmasry et al. | 430/111 |
| 5,075,352 | 12/1991 | Elmasry | 523/201 |
| 5,081,197 | 1/1992 | Heilmann et al. | 526/260 |
| 5,091,489 | 2/1992 | Heilmann et al. | 526/90 |
| 5,094,766 | 3/1992 | Kepuscinski et al. | 252/51.5 |
| 5,138,071 | 8/1992 | Schoellkopf et al. | 548/537 |
| 5,147,957 | 9/1992 | Kumar | 528/15 |
| 5,149,806 | 9/1992 | Moren et al. | 544/72 |
| 5,157,108 | 10/1992 | Krepski et al. | 528/503 |
| 5,157,145 | 10/1992 | Schoellkopf et al. | 560/41 |
| 5,175,081 | 12/1992 | Krepski et al. | 430/617 |
| 5,185,102 | 2/1993 | Harelstad et al. | 252/582 |
| 5,194,623 | 3/1993 | Krepski et al. | 548/261 |
| 5,200,471 | 4/1993 | Coleman et al. | 525/326.9 |

OTHER PUBLICATIONS

University College, Hull, Sep. 27, 1952, pp. 453–456, "The Dehydration and Racemisation of N–Acyl–L–aspartic Acids by Acetic Anhydride", by C.C. Barker.

J. Heterocyclic Chem., 23, 375, 1986, "Novel Synthesis of Pyrido[2,1–fl]–as–Triazinium System and its Zwitterionic Derivatives . . . ", by S. Batori.

J. Heterocyclic Chem., 25, 437 (1988), "Regioselectivity in Methylation and Phenylation of the Zwitterionic Pyrido[2, 1–f]–as–triazinium–1– and 3–olates and thiolates[1]", by Sandor Batori et al.

J. Heterocyclic Chem., 27, 1673 (1990), "Synthesis and Regiospecificity in Methylation of Pyrido[1,a] pyrazinium–1– and 3–olates and Pyrido[1,2–b]pyridazinium–z– and 4–olates [1]", by S. Batori et al.

J.C.S. Perkin II, 1978, 1173, "The Basicities of Substituted N–Trimethylammoniophenylacetamidates and N–Trimethylammoniocinnamamidates. The Hammett Correlations and the Thermodynamics of Protonation", by William H. Beck.

Tetrahedron Letters, No. 4, pp. 289–292, 1972, "The Curtius Rearrangement in Aminimides" by Herman P. Benecke et al.

α–aminoisobutyric acids) from Tripeptide to Pentapeptide: Evidence for a 310 Helix , by Ettore Benedetti.

J. Am. Chem. Soc. 1984, 106, 8146–8152, Folded and Extended Structures of Homooligopeptides from α,α–Dialkylated Glycines. A Conformational Energy Computation and X–ray Diffraction Study, Ettore Benedetti et al.

Gaza Chem. Ital. 95, 1965, "Reazione dei diarildiazoalcani–Nota IV. Difenildiazometano e azoici carbonilici", Gian Franco Bettinetti et al.

Nucleosides & Nucleotides, 10(8), 1657–1665, 1991 "Synthesis of N–Aminopyrazinium Analogs of Cytidine and 2'–Deoxycytidine", by Miroslav Bobek et al.

J. Am. Chem. Soc. 1984, 106, 8152–8156, "Folded and Extended Structures of Homooligopeptides from α,α–Dialkylated α–Amino Acids. An Infrared Absorption and H Nuclear Magnetic Resonance Study", by Gian Maria Bonora.

Bull. Soc. Chim. Belg., vol. 84/n4/1975, pp. 299–304, "Synthesis of a Homologous Series of Protected Oligopeptides Derived From L–Norvaline" by G.M. Bonora et al.

Tetrahedron vol. 38, No. 24, pp. 3579–3583, 1982, "(–)–Isovaline: Confirmation of its D–(=R)–Configuration by X–Ray Analysis of Its N–Chloroacetyl Derivative", by R. Bosch et al.

Tetrahedron Letters No. 31, pp. 2689–2690, 1976, "Allylic and Benzylic Deamination By Thermal Cleavage of 1–substituted 1,2–Dihydro–2, 4, 6–Triphenylpyridines" by A.J. Boulton et al.

Chemistry and Industry, Jul. 11, 1970, "Kinetics of reaction between gaseous oxygen and cobalt(II) ammines" by R. Bratchley et al.

Tetrahedron Letters vol. 21, 5059–5060, 1980, "New Cyclic Aminimides Containing Pyrazolone Skeleton", By M. Poje and N. Bregant.

Biopolymers, vol. 12, 2599–2605 (1973), "An Obligatory α–Helical Amino Acid Residue" by Antony W. Burgess et al.

Chemical Communications, No. 14, Jul. 21, 1971, 725–726, "Crystal and Molecular Structures of Two N–Ammonio–amidates", by A.F. Cameron.

Isophthaloyl –, and 2,2'–Terephthaloylbis[1,1,1–trimethylhydrazinium] Dihydroxie, Bis(Inner Salts): Synthesis, Partition Coefficients, Toxicity and Effect on Ganglionic Transmission", by Lindley A. Cates.

Chemical Abstracts, vol. 89, 1978, p. 250, Mosquito larvicidal and pupicidal activity of aminides", by E. Clarke et al.

Meth and Find Exptl Clin Pharmacol 1987; 9(2):101–110, "Pharmacological Properties of Besulpamide, a New Diuretic, in Rats and Dogs", by M. Colombo, et al.

Newcastle Technical Centre, 1274–1280, Jun. 1969, "Light Scattering by Polydisperse Cylindrical Micelles", by J.M. Corkill et al.

Tetrahedron, vol. 49, No. 15, pp. 3185–3192, 1993, "2–Alkoxycarbonylcycloimmonium Ylides, Efficient 1,4–Dipole Equivalents in the Synthesis of New Conjugated Betaines", by Ana M. Cuadro et al.

Journal of Polymer Science, Part A–1, vol. 6, 363–373 (1968), "Aminimides. IV. Homo– and Copolymerization Studies on Trimethylamine Methacrylimide", by B.M. Culbertson.

Aminimides, vol. 3, No. 6, Nov.–Dec. 1970, 715–722, "Aminimides. VIII Synthesis and Homo–and Copolymerization Studies of 1,11–Trimethylactrylylhydrazinium Chloride and 1,1,1–Trimethylmethacrylylhydrazinium Chloride", by B.M. Culbertson et al.

Journal of Polymer Science: Part A–1, vol. 6, 2197–2207 (1968), "Aminimides V. Preparation and Polymerization Studies of Trimethylamine–4–Vinylbenzimide", by B.M. Culbertson et al.

Applied Polymer Symposium No. 26, 399–410 1975, "Synthesis and Polymerization Studies of Aminimide Monomers Containing Acetoxyl or Carboxylic Acid Residues", by B.M. Culbertson et al.

Meth and Find Exptl Clin Pharmacol 1987; 9(2):111–119, "Acute, Subacute and Subchronic Toxicity of Besulpamide", by I. Demestre et al.

Acids, "Efficient Synthesis of Optically Pure Isomers of β–Methylphenylalanine" by Ramalinga Dharanipragada et al.

Inorg. Nucl. Chem. Letters, vol. 10, pp. 233–235, 1974, "Ortho–Metallation Reactions With 1–Benzoyliminopyridinium Betaine", by Shelton A. Dias et al.

J. Chem Soc., 162, 1975, J.C.S. Dalton, "Metal–Ylide Complexes. Part I. Metallation Reactions . . . ", by Shelton A. Dias et al.

Chemical Abstracts, vol. 70, 1969, 264, "Synthesis of 1–alkyl–1, 1–dimethylhydrazinium salts and N–alkyldimethylaminoacetimides and their properties", Kameyama, Eilichi et al.

Meth and Find Exptl Clin Pharmacol 1987; 9(2):121–126, "Pharmacokinetics of Besulpamide in Rats and Dogs", by J. Esteve.

Chemical Abstracts, vol. 115, 1991, p. 44, "Elimination of disturbances of the heart electric stability and arrhythmias with a synthetic analog of acetylcholine", by F.Meerson et al.

Polymer Bulletin 22, 449–454(1989), "Synthesis and reactivity of highly versatile VDMO–VBC copolymers" by Robert C. Fazio et al.

Tetrahedron, vol. 31, pp. 2559–2569, 1975, "N–(6, 7–Methylenedioxy–3–Quinazolinio)Amidates–I Synthesis Spectra and Some Dark Reactions", J. Fetter.

FEBS Letters, vol. 155, No. 2, "The crystal structure of a 310 helical decapeptide containing α–aminoisobutyric acid" by A.K. Francis.

J. Chem. Soc. Perkin Trans. II 1982, pp. 1235–1239, "The Crystal Structure of the Amino–terminal Pentapeptide of Suzukacillin. Occurrence of a Four–fold Peptide Helix", by Athappilly K. Francis.

Biopolymers, vol. 22, 1499–1505 (1983), "Crystal Structure of Boc–Ala–Aib–Ala–Aib–Aib–Methyl Ester, A Pentapeptide Fragment of the channel–Forming Inonophore Suzukacillin", by A.K. Francis et al.

J. Heterocyclic Chem., 26, (Sep.–Oct. 1989), 1373–1382, Study of the Structure of Besulpamide, 1–[–Chloro–3–sulfamoylbenzoyl)amino]2,4,6–trimethylpyridinium hydroxide inner salt, and related compounds, using X–ray Crystallography and $^1$H and $^{13}$C Nuclear Magnetic Resonance Spectroscopy, Jordi Frigola et al.

Chemical Communications, 1968, 917–918, "The Crystal Structure of a Novel Heterocycle containing an Intramolecular Carbon–Nitrogen Hydrogen Bond", by Charles J. Fritchie et al.

metric Study of Complexation of para–substituted N–Ammoniobenz–amidates by Boron Trifluoride", by Jean–Francois Gal et al.

Intra–Science Chemistry Reports, vol. 5, No. 4, 1971, pp. 305–316 "Studies on the Biologically–Active Conformations of Angiotensin" by Garland Marshall.

Acta Chem. Scand. 9 (1955), No. 9, 1498–1509, "The Reaction of Hydrazine with Cinnamic Acid Derivatives", by W.O. Godtfredsen et al.

Polymer Letters, vol. 2, pp. 1095–1096 (1964), "Thermally Reversible Homopolymer Gel Systems", by Howard Haas et al.

Tetrahedron Letters, No. 26, pp. 1733–1737, 1964, "Reaktionen von Benzol–Derivaten Mit Nitrenen", by Klaus Hafner et al.

Int. J. Peptide Protein Res. 21, 1983, 392–405, "Peptides containing dipropylglycine", by Paul M. Hardy et al.

Bull. Soc. Chim. Belg., 65, pp. 291–296, 1956, "Syntheses des isocyanates de vi2nyle et d'isoprpenyle", by R. Hart.

Journal of Fluorine Chemistry, 51, 1991 419–431, "Amine-(polyfluoroalkoxyacyl)imide Surfactants[1]", by Lisa Haywood et al.

Journal of Polymer Science, vol. 22, 3149–3160(1984), "Chemistry of Alkenyl Azlactones. IV. Preparation and Properties of Telechelic Acrylamides Derived from Amine-–terminated Oligomers" by Steven M. Heilmann et al.

J. Med. Chem. 1991, 34, 1777–1789, "Synthesis, Conformational Properties, and Antibody Recognition of Peptides Containing β–Turn Mimetics Based on α–Alkylproline Derivatives" by Mark G. Hinds.

Biopolymers, vol. 22, 517–530(1983), "Conformational and Dynamic Considerations in the Design of Peptide Hormone Analogs", by Victor J. Hruby et al.

Alkenyloxazolonen" by Von Klaus Hubner et al.

Liebigs Ann. Chem. 1977, 506–527, "Additionen mit Chinolinium–, Isochinolinium– und Phenanthridinium–N–imid", by Rolf Huisgen et al.

Organic Mass Spectrometry, 1971, vol. 5, pp. 61 to 71, "The Mass Spectra of N–Acyliminopyridinium and Isoquinolinium Betaines", by M. Ikeda et al.

Journal of Polymer Science: Part A: Polymer Chemistry, vol. 25, 1363–1382 1987, "Thermal Decomposition Behavior of Bis–aminimides and Their Application to Polymerization of Epoxide" by Shinzo Inubushi et al.

Journal of Polymer Science, Part A:, Polymer Chemistry, vol. 26, 1779–1789 (1988), "Tough Epoxy Resins Cured with Aminimides", by Shinzo Inubushi et al.

Can. J. Chem., vol. 52, 1974, 3671–3675, "New Route to Cyclic Azomethine Imines", By P.C. Ip et al.

Journal of Molecular Structure, 243 (1991) 365–368, "A Multinuclear NMR Study On Some Cyclic Aminimides and Related Compounds", by J. Jazwinski.

Chemical Abstracts, vol. 72, 1970, 45292, "Reactive surfactants. II. Synthesis of 2–acyl–1,1,1–trimethylhydrazinium hydroxide inner salts and their properties", by E. Kameyama et al.

Chem. Phar. Bull., vol. 23, 1975, 452–455, "Studies on Ketene and Its Derivatives. LXVIII Reaction of Kiketene with N–Imino–pyridinium, –quinolinium, and –isoquinolium Ylides", Tetsuzo Kato et al.

Gazzetta Chimica Italiana, 117, 1987, 509–511, "The Structure of the Pyridine 1–Benzimide Mono Cation", by Alan r. Katritzky.

Angew: Chem. Int. Ed. Engl. 23 420–429, 1984, Pyrylium Mediated Transformations of Primary Amino Groups into Other Functional Groups, by Alan R. Katritzky et al.

Heterocycles, vol. 18, 1982, "Pyrazolo(1,5–c)Pyrimidines from pyrylium Salts and Amidrazones and Pyridine Imidoyl–N–Imides from Inidoyl Chlorides", by Alan R. Katritzky et al.

J. Am. Chem. Soc. 1991, 113, 2275–2283, "Topographic Design of Peptide Neurotransmitters and Hormones on Stable Backbone Templates: Relation of conformatioin and Dynamics to Bioactivity" by Wieslaw M. Kazmierski et al.

J. Org. Chem., 1981, 46, 2490–2497, Relative Reactivity and Structures of Benzoyltrimethylhydrazone and 1–Benzoyl–2–methylpyrazolidine, by Spencer Knapp.

Journal of Polymer Science: Polymer Chemistry Edition, vol. 21, 3597–3600 1983, "Synthesis of Polymers Containing Pyridinium Ylide and Iminopyridinium Ylide Structure", by S. Kondo et al.

hydraziniumsalzen by Karl–Heinz Konig et al.

Tetrahedron, vol. 38, No. 14, pp. 2165–2181, 1982, "Syntheses von 2–Methylalanin–Peptiden, die pH–Abhangigkeit Ihrer ⁻C–NMR–Spektren und Eine Neue Methode Zur Auswertung uber CS–Diagramme," by Dieter Leibfritz.

Chemica Scripta. 1978–79, 13, 195–196, "Electron Deficient Heteroaromatic Ammonioamidates, 20[1]; N–(3–Quinazolinio)amidates, 8[1]", by M. Lempert–Sreter, et al.

Tetrahedron, 1960, vol. 11, pp. 39 to 51., "Synthesis of Peptides Derived From Alpha–Methylalanine", by M.T. Leplawy et al.

Helvetica Chimica Acta—vol. 65, Fasc. 1 (1982)–Nr. 18, "18. Azimine. VI. [12]) 1–Alkoxycarbonyl–2,3–dialkyl– und –2,3–diaryl–azimine" by von Christian Leuenberger.

Monatshefte fur Chemie, 120, 749–758 (1989), "1–Amino–2–hydrazinopyrimidin–N–ylides. Unusual Tautomers of 1–Aminopyrimidin–2–hydrazones", by Jurgen Liebscher.

J.C.S. Perkin, Trans 2, 1977, 909–914, "Mono– and Di–protonation Sites in N–Ammonio–amidates: a Specro–scopic Study", by Milica Liler et al.

J.C.S. Perkins II, 1980, 380, "The Kinetics of Hydrolysis of N–Trimethylammonioacetamide and of Substituted N–Trimethylammoniobenzamides in Concentrated Sulphuric Acid", by Milica Liler et al.

Tetrahedron Letters No. 48, 4263–4266, 1974, "Cyclic Aminimides Containing The pyrazolone Skeleton", by William J.S. Lockley.

Canadian Journal of Chemistry, vol. 50, 1972, "Reaction of Diphenylcyclopropenethione with Pyridinium Imines", by J.W. Lown et al.

Tetrahedron Letters No. 5., 425–428, 1971, "Cycloadditions of Aminoisocyanates to Heterocumulenes", by Walter Lwowski et al.

Liebigs Ann. Chem. 1980 715–724, "Die Kristallstruktur von α(tert–Butyloxcarbonylamino)–isobuttersaure" by Wilfried Mayr et al.

Canadian Journal of Chemistry, vol. 45, 1967, 2619–2622, "Aminimides. II. A one–step synthesis of aminimides from carboxylic acid esters", by William J. McKillip.

Chemical Reviews, 1973, vol. 73, No. 3, pp. 255–281, "The Chemistry of Aminimides", by W.J. McKillip et al.

Chemical Abstracts, vol. 114, 1991, p. 40, "Antiarrhythmic effect of adaptive activation of the vagal system and a new synthetic acetylcholine analog", by F.Z. Meerson.

Journal of Polymer Science: Polymer Chemistry Edition, vol. 21: 1159–1164 1983, Synthesis of Aminimide Monomers and Polymers, Avinash C. Mehta et al.

Journal of Polymer Science: Part A: Polymer Chemistry, vol. 29, 29–37(1991), "Copolymers of 2–Vinyl–4,4–Dimethylazlactone with Styrene and Ethyl α–Hydroxymethylacrylate" by Jeno Muthiah et al.

Acc. Chem. Res. 1981, 14, pp. 356–362, "Alamethicin, A Transmembrane Channel" by Ramakrishnan Nagaraj et al.

Journal of the American Chemical Society, 101:1, Jan. 3, 1979, "Stereochemically Constrained Linear Peptides. Conformations of Peptides Containing α–Aminoisobutyric Acid", by R. Nagaraj et al.

Acta Cryst. (1980), B36, 1498–1500, "Structure of a Peptide Oxazolone: 2–(1'–Benzyloxycarbonylamino–1'–methylethyl)–4,4–dimethyl–5–oxazolone", by C.M.K. Nair et al.

Tetrahedron Letters, vol. 30, No. 49, pp. 6845–6848, 1989, "Asymmetric Synthesis of Unusual Amino Acids: Synthesis of Optically Pure Isomers of α–methyltyrosine", by Ernesto Nicolas.

Journal of Applied Polymer Science, vol. 27, 2361–2368 1982, "Aminimide as Hardener/Curing Promoter for One Part Epoxy Resin Composition", by Hideki Niino et al.

Chem Pharm Bull, vol. 11 (1963), pp. 774–748, "Pyridazine Derivatives IV. The Structures of Aminopyridazines", by Yoshiro Nitta.

Journal of Applied Polymer Science, vol. 27, 2361–2368 (1982), "Aminimide as Hardener/Cruing Promotor for One Part Epoxy Resin Composition", by Hideri Nhno and Saburo Noguchi.

Chem. Pharm. Bull., vol. 14(5) 518–523, 1966, "Reaction of N–Aminopyridinium Derivatives.V. Syntheses of 1–(N–Methylacetamido)alkylpyridinium Salts and Their Reaction with Cyanide Ion", by Toshihiko Okamoto et al.

Ollis

J. Am. Chem. Soc., vol. 103, No. 11, 1981, pp. 2948–2955, "Sensitivity of Polypeptide Conformation to Geometry. Theoretical Conformational Analysis of Oligomers of – Aminoisobutyric Acid", by Yvonne Paterson et al.

J. Org. Chem., 1982, 47, 5023–5025, Degradation of Aminimides Obtained from Enamines and (Ehoxycarbonyl)nitrene", by Lucio Pellacani et al.

Journal of Molecular Structure, 86 (1982) 341–347, "Quantum Theory of the Structure and Bonding in Proteins", by David Peters and Jane Peters.

J.C.S. Dalton I, 1978, 1155, "Reactions of 2–Azidopyridine and 1–Pyridinio Ylides with Transition–metal Complexes", by Maddalena Pizzotti.

The Journal of Organic Chemistry, vol. 33, No. 10, Oct. 1968, "Bridgehead Nitrogen Heterocycles. I. A Convenient Synthesis of Pyrazolo[1,5–a]pyridines", by K.T. Potts et al.

Biochemical and Biophysical Research Communications, vol. 103, No. 3, 1981, pp. 898–904, "Hydrophobic Channels in Crystals of an x–Aminoisobutyric Acid Pentapeptide", by Ch. Pulla Rao et al.

Biopolymers, vol. 21, 2461–2472 (1982), "Molecular Structure of t–Butyloxycarbonyl–Leu–Aib–Pro–Val–Aib–Methyl Ester, a Fragment of Alamethicin and Suzukacillin: a $3_{10}$–Helical Pentapeptide", by Ch. Pulla Rao et al.

Makromol. Chem., Rapid Commun. 5,67–70 (1984), "Chemistry of Alkenylazlactones, $2^{a)}$ Reaction with thiols", by Jerald K. Rasmussen et al.

J. Hetrocyclic Chem., 27, 1041 (1990), "Synthesis of Some N–S[Pyridyl(phenyl)carbonylamino]–alkyl–1,2,3,6–tetrahydropyridines", by Kinfe K. Redda.

J. Med. Chem., 1979, vol. 22, No. 9, 1079, "Syntheses of N–Substituted 2(3,4)–Pyridylcarboxylic Acid Hydrazides with Analgesic and Antiinflammatory Activity", by Kinfe Redda et al.

Journal of Pharmaceutical Sciences, vol. 81, No. 5, May 1992, "Synthesis and Pharmacological Evaluation of Some N–[Pyridyl(phenyl)carbonylamino]methyl–1,2,3,6–tetrahydropyridines" by Kinfe K. Redda et al.

Tetrahedron, vol. 49, No. 18, pp. 3767–3780, 1993, "Electrophilic Amination of Pyrimidine–2–thiones—Synthesis of Zwitterionic 2–Aminothiopyrimidinium–N–ylides, Pyrimidine–2–ones and Bicyclic Pyrimidinium Compounds", by Beate Riemer et al.

Acta Cryst. (1983), C39, 894–896, "tert–Butyloxcarbonyl–α–aminoisobutyryl–α–aminoisobutyrate Benzyl Ester, $C_{20}H_{30}N_2O_5$", by Patrick Van Roey et al.

Int. J. Peptide Protein Res. 19, 1982, 499–505, "Crystal and molecular structure of tert.–butyloxycarbonyl–L–hydroxy–prolyl–α–aminoisobutryl–α–aminoisobutryl–L–phenylalaninol" by Patrick Van Roey et al.

Biopolymers, vol. 32, 407–410 (1992), "Peptidomimetics as Receptors Agonists or Peptidase Inhibitors: A Structural Approach in the Field of Enkephalins, ANP and CCK" by Bernard P. Roques.

Tetrahedron Letters No. 52, pp. 4859–4862, 1976, "Regiospecific Versus Non–Regiospecific Photoinduced Ring–Enlargement of 3–Substituted 1–Iminopyridinium Ylides", by Jacques S. et al.

Liebigs Ann. Chem. 1982, 1304–1321, "The α–Helical Conformation of the Undecapeptide Boc–L–Ala–[Aib–Ala]$_2$–Glu(OBzl)–Ala–[Aib–Ala]$_2$–OMe: Synthesis, X–Ray Crystal Structure, and Conformation in Solution", by Heribert Schmitt.

Liebigs Ann. chem. 1988, 1025–1031, "Asymmetric Synthesis of Boc–L–Val–(R)–α–MePro–OMe, Boc–L–Val–(R)– Proome, and of Boc–L–Val–(R)–α–MePhe–OMe, Ac–L–Val–(R)–α–MePhe–OMe and Their Analogues. A New Strategy for the Synthesis of Non–Proteinogenic Dipeptides", by Ulrich Schollkopf.

Angew. Chem., 90 (1978), Nr. 2, pp. 136–138, "Asymmetrische Syntheses von x–Alkyl–x–aminocarbon–sauren durch Alkylierung von 1–chiral–sustituierten 2–Imidazonin–5–onen", by Von Ulrich Schollkopf et al.

Angew Chem. Int. Ed. Engl. 18 (1979), No. 11, Enantioselective Synthesis of α–Methyl–αaminocarboxylic Acids by Alkylation of the Lactim Ether of cyclo–(I–ala–I–Ala), by Ulrich Schollkopf et al.

Angew, Chem. Internat. Edit., vol. 14(1975), No. 8, "Applications of Field Desorption Mass Spectrometry in Inorganic Chemistry: Salts", by H.R. Schulten.

Biophy.J., vol. 64, Apr. 1993, 1017–1028, "The permeation properties of small organic cations in gramicidin A channels", by Sang–Ah Seoh.

J.C.S. Chem. Comm., 1978, pp. 996–997, "The $3_{10}$ Helical Conformation of a Pentapeptide Containing a–Aminoisobutyric Acid (Aib): X–Ray Crystal Structure of Tos–(Aib)$_5$–OMe", by N. Shamala et al.

Chemical Abstracts, vol. 115, 1991, p. 45, "Regulation of the carnitive–dependent metabolism of fatty acids in the rat myocardium", Zh. Shutenko et al.

Hydroxethyldimethylamine Acylimides" by Robert J. Small.

J. Am. Chem. Soc., 1981, vol. 103, pp. 1493–1501,"Crystal Structures and Conformational Calculations of Fragments of Alamethicin Containing Aminoisobutyric" by G. David Smith.

J. Org. Chem., vol. 59, No. 14, 1974, "Stevens Rearrangement of Carbamoylaminimides" by Richard F. Smith et al.

Bull. Soc. Chem., France—1969 No. 6, 2175–2179, "No. 382—Syntheses Photochimique de (1–H)–Diazepines–1,2" by Jacques Streith et al.

Chem. Ber. III, 780–790 (1978), "Pyrazolium–Betaine aus 1, 1–Dialkylhydrazinen und Acetylencarbonsaureestern", by Wolfgage Sucrow et al.

Chem. Pharm. Bull., vol. 31, 1983, 1378–1381, "1,3–dipolar Cycloaddition Reaction of 1–Methylperimidine 3–Ylides with Dimethyl Accetylenedierboxylate", by Yasumitsu Tamura et al.

J. Heterocyclic Chem., 9, Aug. 1972, 865, "Synthesis of 3–substituted N–Aminopyridinium Salts(I)", by Yasumitsu Tamura et al.

J.C.S. Perkin I, 1973, 2580–2583, "Synthesis and Thermal Reaction of 2,2–Diacyl–N–(1–pyridinio)vinyl–aminides: Formation of Pyrazolo[1,5–a]pyridines and Isoxazoles", by Yasumitsu Tamura et al.

Organic Preparations and Procedures 1(3), 217–219 (1969), "A convenient synthesis of 5–oxazolones. 2–phenyl–5–oxazolone" by Lloye D. Taylor et al.

Polymer Letters, vol. 7, pp. 597–603(1969), "The Synthesis of Vinyl Peptide Monomers", by L.D. Taylor et al.

Journal of Polymer Science: Part C: Polymer Letters, vol. 24, 287–289 (1986),"A Polymer whose Aqueous Solutions Show the Properties of Negative Thixotropy and Thermoreversible Gelation: (Poly–Trimethylamine p–Vinlybenzimide), by Lloyd D. Taylor et al.

Makromol Chem., Rapid Commun. 3, 779–782(1982), "Synthesis of Poly(4,4–dimethyl–2–vinly–5–oxazolone) an Interesting Material for Preparing Polymeric Agents", by Lloye D. Taylor et al.

Polymer Letters, vol. 9, pp. 187–190(1971), "Synthesis and Polymerization of 2–vinyl–4,4–Dimethyl–5–Oxazolone" by L.D. Taylor et al.

Eur. J. Med. Chem.—Chem. Ther. 1982–17, N. 3, pp. 265–270, "Aminimides ethyleniques a action vasodilatatrice peripherique", by Mohamed Tichniouin et al.

Eur. J. Med. Chem., 1982, 17, No. 3, pp. 265–270, "Aminimides ethyleniques a action vasodilatatrice peripherique", by M. Tichniovin et al.

J. Chem. Soc. Perkin Trans. 1988, "Reactions of Some 1,3–Diaminoucleophiles with Azlactones" by Ahmad M. Tikdari et al.

Int. J. Peptide Protein Res. 22, 1983, 603–610, "Bioorganic stereochemistry", by Claudio Toniolo et al.

Biopolymers, vol. 22, 205–215(1983), "Preferred Conformations of Peptides Containing α,α–Disubstituted α–Amino Acids, by Claudio Toniolo et al.

Bull Chem. Soc. Japan, 1980, 53, 1149, "Reaction of Ethyl Aziodoformate with Morpholines", by Teruko Tshuchida et al.

J. Chem. Soc. Perkin Trans. 11, 1993, "On the Nature of Nitrogen–Nitrogen Bonding in Cyclic Aminimides", by Shinji Tsuchiya.

Chem. Pharm. Bull. 31(12)456804572 1983, "Thermal Rearrangements of Cyclic Amine Ylides. III.[1)] Intramolecular Cyclization of 2–Ethynylpyridine N–Imides to 3–Azaindolizine Derivatives", by Takashi Tsuchiya et al.

J. Org. Chem., vol. 44, No. 16, 1979, 2850–2855, "On the Bond Character of N–Containing Ylides", by Shinji Tsuchiya et al.

Chem. Pharm. Bull., 30 (10)3757, 1982, "Studies on Diazepines. XVIII. Photochemical Synthesis of 3H–1,3–Benzodiazepines from Quinoline N–Acylimides", by Takashi Tsuchiya et al.

Bull Chem. Soc. Japan, 1983, 2073, "Double Cycloaddition Reaction of Imidazolium Methylides. Intermolecular 1,3–Dipolar and Intramolecular Diels–Alder Cycloaddition Reactions", by Otohiko Tsuge et al.

Journal American Chemical Society, vol. 82, 1960, 5718–5721, "The Rearrangement of 1,1–Dimethyl–1–p–nitrobenzylamine–2–acetamide", by S. Wawzonek.

Journal of Chemistry, 28, 1963, vol. 28, 2376–2377, The Resolution of 1–Ethyl–1–methyl–1–p–nitrobenzylamine–2–acetamide", by S. Wawzonek et al.

Organic Preparations and Procedures Int. 8(5), 215–217 (1976), "Electrolytic Prepartion of bis–Dimethyl–2–Hydroxypropylamineazobenzimides", by S. Wawzonek et al.

J. Med. Chem., 1982, 25, 720–723, "Synthesis of N–[[(Substituted–phenyl)carbonyl]amino]–1,2,3,6–tetrahydropyridines with Analgesic and Hyperglycemic Activity", by Jupita M. Yeung.

J. Med. Chem, 1987, 30, 104–108, "Synthesis of N–(3, 6–Dihydro–1(2H)–pyridinyl)benzamides with Hyperglycemic–Hypoglycemic Activity", by Jupita M. Yeung et al.

J. Med. Chem. 1982, 25, 191–195, "Synthesis of N–(Carbonylamino)–1,2,3,6–tetrahydropyridines with Analgesic, Antiinflammatory, and Hyperglycemic Activity", by Jupita M. Yeung et al.

AMINIMIDE-CONTAINING MOLECULES AND MATERIALS AS MOLECULAR RECOGNITION AGENTS

CROSS REFERENCE TO RELATED APPLICATIONS

This is a continuation of U.S. application Ser. No. 08/204,206, filed Mar. 27, 1995, now U.S. Pat. No. 5,705,585.

1. FIELD OF THE INVENTION

The present invention relates to the logical development of biochemical and biopharmaceutical agents and of new materials including fabricated materials such as fibers, beads, films, and gels. Specifically, the invention relates to the development of molecular modules based on aminimide and related structures, and to the use of these modules in the assembly of molecules and fabricated materials with tailored properties, which are determined by the contributions of the individual building modules. The molecular modules of the invention are preferably chiral, and can be used to synthesize new compounds and fabricated materials which are able to recognize biological receptors, enzymes, genetic materials, and other chiral molecules, and are thus of great interest in the fields of biopharmaceuticals, separation and materials science.

2. BACKGROUND OF THE INVENTION

The discovery of new molecules has traditionally focused in two broad areas, biologically active molecules, which are used as drugs for the treatment of life-threatening diseases, and new materials, which are used in commercial, especially high-technological applications. In both areas, the strategy used to discover new molecules has involved two basic operations: (i) a more or less random choice of a molecular candidate, prepared either via chemical synthesis or isolated from natural sources, and (ii) the testing of the molecular candidate for the property or properties of interest. This discovery cycle is repeated indefinitely until a molecule possessing the desirable properties is located. In the majority of cases, the molecular types chosen for testing have belonged to rather narrowly defined chemical classes. For example, the discovery of new peptide hormones has involved work with peptides; the discovery of new therapeutic steroids has involved work with the steroid nucleus; the discovery of new surfaces to be used in the construction of computer chips or sensors has involved work with inorganic materials, etc. As a result, the discovery of new functional molecules, being ad hoc in nature and relying predominantly on serendipity, has been an extremely time-consuming, laborious, unpredictable, and costly enterprise.

A brief account of the strategies and tactics used in the discovery of new molecules is described below. The emphasis is on biologically interesting molecules; however, the technical problems encountered in the discovery of biologically active molecules as outlined here are also illustrative of the problems encountered in the discovery of molecules which can serve as new materials for high technological applications. Furthermore, as discussed below, these problems are also illustrative of the problems encountered in the development of fabricated materials for high technological applications.

2.1 Drug Design

Modern theories of biological activity state that biological activities, and therefore physiological states, are the result of molecular recognition events. For example, nucleotides can form complementary base pairs so that complementary single-stranded molecules hybridize resulting in double- or triple-helical structures that appear to be involved in regulation of gene expression. In another example, a biologically active molecule, referred to as a ligand, binds with another molecule, usually a macromolecule referred to as ligand-acceptor (e.g. a receptor or an enzyme), and this binding elicits a chain of molecular events which ultimately gives rise to a physiological state, e.g. normal cell growth and differentiation, abnormal cell growth leading to carcinogenesis, blood-pressure regulation, nerve-impulse-generation and -propagation, etc. The binding between ligand and ligand-acceptor is geometrically characteristic and extraordinarily specific, involving appropriate three-dimensional structural arrangements and chemical interactions.

2.1.1 Design and Synthesis of Nucleotides

Recent interest in gene therapy and manipulation of gene expression has focused on the design of synthetic oligonucleotides that can be used to block or suppress gene expression via an antisense, ribozyme or triple helix mechanism. To this end, the sequence of the native target DNA or RNA molecule is characterized and standard methods are used to synthesize oligonucleotides representing the complement of the desired target sequence (see, S. Crooke, The FASEB Journal, Vol. 7, April 1993, p. 533 and references cited therein). Attempts to design more stable forms of such oligonucleotides for use in vivo have typically involved the addition of various functional groups, e.g., halogens, azido, nitro, methyl, keto, etc. to various positions of the ribose or deoxyribose subunits (cf., *The Organic Chemistry of Nucleic Acids*, Y. Mizuno, Elsevier Science Publishers BV, Amsterdam, The Netherlands, 1987).

2.1.2 Glycopeptides

As a result of recent advances in biological carbohydrate chemistry, carbohydrates increasingly are being viewed as the components of living systems with the enormously complex structures required for the encoding of the massive amounts of information needed to orchestrate the processes of life, e.g., cellular recognition, immunity, embryonic development, carcinogenesis and cell-death. Thus, whereas two naturally occurring amino acids can be used by nature to convey 2 fundamental molecular messages, i.e., via formation of the two possible dipeptide structures, and four different nucleotides convey 24 molecular messages, two different monosaccharide subunits can give rise to 11 unique disaccharides, and four dissimilar monosaccharides can give rise to up to 35,560 unique tetramers each capable of functioning as a fundamental discreet molecular messenger in a given physiological system.

The gangliosides are examples of the versatility and effect with which organisms can use saccharide structures. These molecules are glycolipids (sugar-lipid composites) and as such are able to position themselves at strategic locations on the cell wall: their lipid component enables them to anchor in the hydrophobic interior of the cell wall, positioning their hydrophilic component in the aqueous extracellular millieu. Thus the gangliosides (like many other saccharides) have been chosen to act as cellular sentries: they are involved in both the inactivation of bacterial toxins and in contact inhibition, the latter being the complex and poorly understood process by which normal cells inhibit the growth of adjacent cells, a property lost in most tumor cells. The structure of ganglioside GM, a potent inhibitor of the toxin secreted by the cholera organism, featuring a branched complex pentameric structure is shown below.

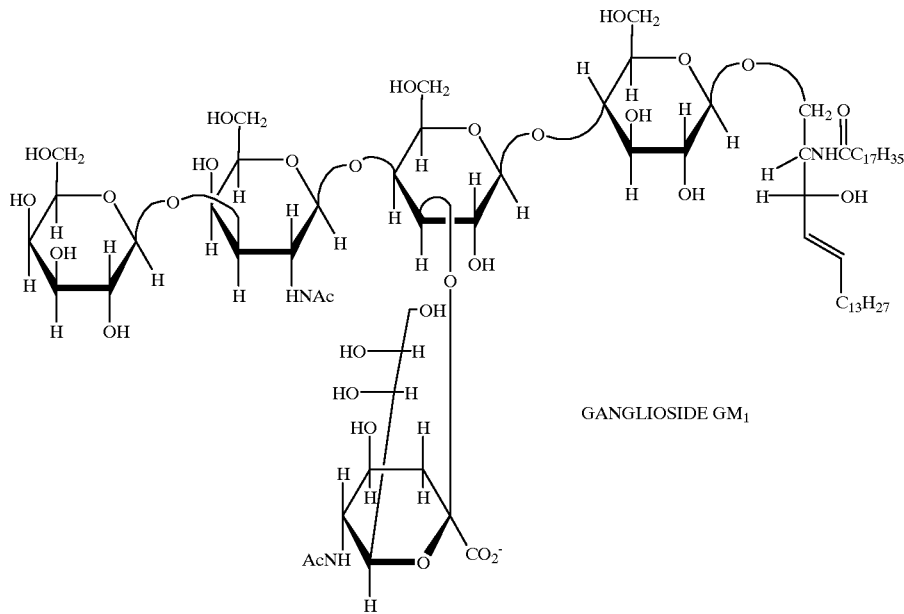
GANGLIOSIDE GM$_1$
The oligosaccharide components of the glycoproteins (sugar-protein composites) responsible for the human blood-group antigens (the A, B, and O blood classes) are shown below.
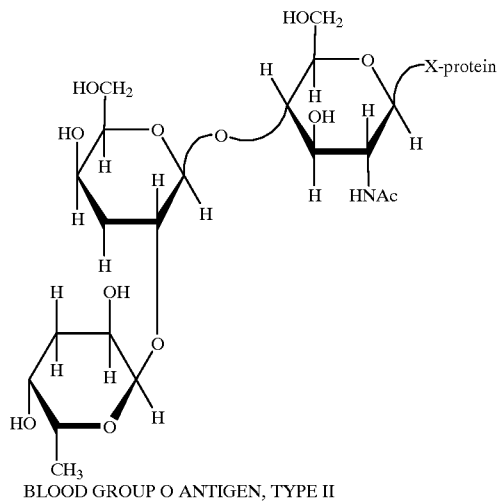
BLOOD GROUP O ANTIGEN, TYPE II -continued

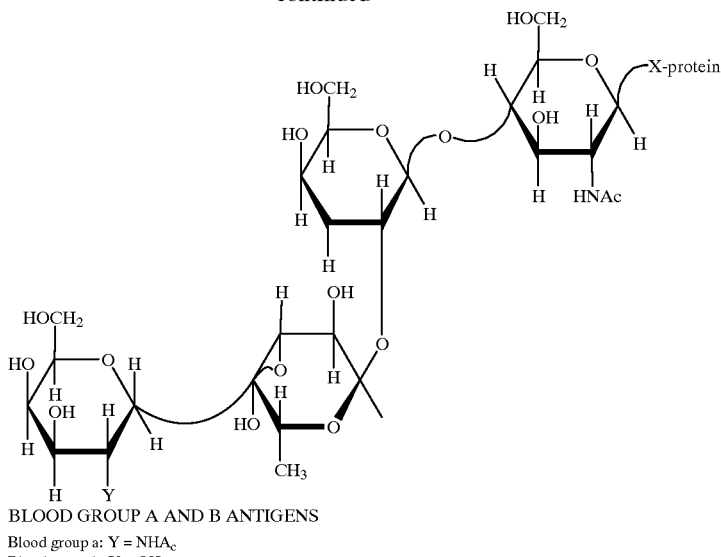

BLOOD GROUP A AND B ANTIGENS
Blood group a: Y = NHA$_c$
Blood group b: Y = OH

Interactions involving complementary proteins and glycoproteins on red blood cells belonging to incompatible blood classes cause formation of aggregates, or clusters and are the cause for failed transfusions of human blood.

Numerous other biological processes and macromolecules are controlled by glycosylation (i.e., the covalent linking with sugars). Thus, deglycosylation of erythropoetin causes loss of the hormone's biological activity; deglycosylation of human gonadotropic hormone increases receptor binding but results in almost complete loss of biological activity (see Rademacher et al., *Ann. Rev. Biochem* 57, 785 (1988); and glycosylation of three sites in tissue plasminogen activating factor (TPA) produces a glycopolypeptide which is 30% more active than the polypeptide that has been glycosylated at two of the sites.

2.1.3 Design and Synthesis of Mimetics of Biological Ligands

A currently favored strategy for development of agents which can be used to treat diseases involves the discovery of forms of ligands of biological receptors, enzymes, or related macromolecules, which mimic such ligands and either boost, i.e., agonize, or suppress, i.e., antagonize the activity of the ligand. The discovery of such desirable ligand forms has traditionally been carried out either by random screening of molecules (produced through chemical synthesis or isolated from natural sources), or by using a so-called "rational" approach involving identification of a lead-structure, usually the structure of the native ligand, and optimization of its properties through numerous cycles of structural redesign and biological testing. Since most useful drugs have been discovered not through the "rational" approach but through the screening of randomly chosen compounds, a hybrid approach to drug discovery has recently emerged which is based on the use of combinatorial chemistry to construct huge libraries of randomly-built chemical structures which are screened for specific biological activities. (S. Brenner and R. A. Lerner, 1992, *Proc. Natl. Acad. Sci. USA* 89:5381)

Most lead-structures which have been used in "rational" drug design are native polypeptide ligands of receptors or enzymes. The majority of polypeptide ligands, especially the small ones, are relatively unstable in physiological fluids, due to the tendency of the peptide bond to undergo facile hydrolysis in acidic media or in the presence of peptidases. Thus, such ligands are decisively inferior in a pharmacokinetic sense to nonpeptidic compounds, and are not favored as drugs. An additional limitation of small peptides as drugs is their low affinity for ligand acceptors. This phenomenon is in sharp contrast to the affinity demonstrated by large, folded polypeptides, e.g. proteins, for specific acceptors, e.g. receptors or enzymes, which is in the subnanomolar range. For peptides to become effective drugs, they must be transformed into nonpeptidic organic structures, i.e., peptide mimetics, which bind tightly, preferably in the nanomolar range, and can withstand the chemical and biochemical rigors of coexistence with biological fluids.

Despite numerous incremental advances in the art of peptidomimetic design, no general solution to the problem of converting a polypeptide-ligand structure to a peptidomimetic has been defined. At present, "rational" peptidomimetic design is done on an ad hoc basis. Using numerous redesign-synthesis-screening cycles, peptidic ligands belonging to a certain biochemical class have been converted by groups of organic chemists and pharmacologists to specific peptidomimetics; however, in the majority of cases the results in one biochemical area, e.g. peptidase inhibitor design using the enzyme substrate as a lead cannot be transferred for use in another area, e.g. tyrosine-kinase inhibitor design using the kinase substrate as a lead.

In many cases, the peptidomimetics that result from a peptide structural lead using the "rational" approach comprise unnatural α-amino acids. Many of these mimetics exhibit several of the troublesome features of native peptides (which also comprise α-amino acids) and are, thus, not favored for use as drugs. Recently, fundamental research on the use of nonpeptidic scaffolds, such as steroidal or sugar structures, to anchor specific receptor-binding groups in fixed geometric relationships have been described (see for example Hirschmann, R. et al., 1992 *J. Am. Chem. Soc.*, 114:9699–9701; Hirschmann, R. et al., 1992 *J. Am. Chem. Soc.*, 114:9217–9218); however, the success of this approach remains to be seen.

In an attempt to accelerate the identification of lead-structures, and also the identification of useful drug candidates through screening of randomly chosen compounds, researchers have developed automated methods for the generation of large combinatorial libraries of peptides and certain types of peptide mimetics, called "peptoids", which are screened for a desirable biological activity. For example, the method of H. M. Geysen, (1984 *Proc. Natl. Acad. Sci. USA* 81:3998) employs a modification of Merrifield peptide synthesis wherein the C-terminal amino acid residues of the peptides to be synthesized are linked to solid-support particles shaped as polyethylene pins; these pins are treated individually or collectively in sequence to introduce additional amino-acid residues forming the desired peptides. The peptides are then screened for activity without removing them from the pins. Houghton, (1985, *Proc. Natl. Acad. Sci. USA* 82:5131; and U.S. Pat. No. 4,631,211) utilizes individual polyethylene bags ("tea bags") containing C-terminal amino acids bound to a solid support. These are mixed and coupled with the requisite amino acids using solid phase synthesis techniques. The peptides produced are then recovered and tested individually. Fodor et al., (1991, *Science* 251:767) described light-directed, spatially addressable parallel-peptide synthesis on a silicon wafer to generate large arrays of addressable peptides that can be directly tested for binding to biological targets. These workers have also developed recombinant DNA/genetic engineering methods for expressing huge peptide libraries on the surface of phages (Cwirla et al., 1990, *Proc. Natl. Acad. Sci. USA* 87:6378).

In another combinatorial approach, V. D. Huebner and D. V. Santi (U.S. Pat. No. 5,182,366) utilized functionalized polystyrene beads divided into portions each of which was acylated with a desired amino acid; the bead portions were mixed together and then split into portions each of which was subjected to acylation with a second desirable amino acid producing dipeptides, using the techniques of solid phase peptide synthesis. By using this synthetic scheme, exponentially increasing numbers of peptides were produced in uniform amounts which were then separately screened for a biological activity of interest.

Zuckerman et al., (1992, *Int. J. Peptide Protein Res.* 91:1) also have developed similar methods for the synthesis of peptide libraries and applied these methods to the automation of a modular synthetic chemistry for the production of libraries of N-alkyl glycine peptide derivatives, called "peptoids", which are screened for activity against a variety of biochemical targets. (See also, Symon et al., 1992, *Proc. Natl. Acad. Sci. USA* 89:9367). Encoded combinatorial chemical syntheses have been described recently (S. Brenner and R. A. Lerner, 1992, *Proc. Natl. Acad. Sci. USA* 89:5381).

In addition to the lead structure, a very useful source of information for the realization of the preferred "rational" drug discovery is the structure of the biological ligand acceptor which, often in conjunction with molecular modelling calculations, is used to simulate modes of binding of the ligand with its acceptor; information on the mode of binding is useful in optimizing the binding properties of the lead-structure. However, finding the structure of the ligand acceptor, or preferably the structure of a complex of the acceptor with a high affinity ligand, requires the isolation of the acceptor or complex in the pure, crystalline state, followed by x-ray crystallographic analysis. The isolation and purification of biological receptors, enzymes, and the polypeptide substrates thereof are time-consuming, laborious, and expensive; success in this important area of biological chemistry depends on the effective utilization of sophisticated separation technologies.

Crystallization can be valuable as a separation technique but in the majority of cases, especially in cases involving isolation of a biomolecule from a complex biological milieu, successful separation is chromatographic. Chromatographic separations are the result of reversible differential binding of the components of a mixture as the mixture moves on an active natural, synthetic, or semisynthetic surface; tight-binding components in the moving mixture leave the surface last en masse resulting in separation.

The development of substrates or supports to be used in separations has involved either the polymerization/crosslinking of monomeric molecules under various conditions to produce fabricated materials such as beads, gels, or films, or the chemical modification of various commercially available fabricated materials e.g., sulfonation of polystyrene beads, to produce the desired new materials. In the majority of cases, prior art support materials have been developed to perform specific separations or types of separations and are thus of limited utility. Many of these materials are incompatible with biological macromolecules, e.g., reverse-phase silica frequently used to perform high pressure liquid chromatography can denature hydrophobic proteins and other polypeptides. Furthermore, many supports are used under conditions which are not compatible with sensitive biomolecules, such as proteins, enzymes, glycoproteins, etc., which are readily denaturable and sensitive to extreme pH's. An additional difficulty with separations carried out using these supports is that the separation results are often support-batch dependent, i.e. they are irreproducible.

Recently a variety of coatings and composite-forming materials have been used to modify commercially available fabricated materials into articles with improved properties; however the success of this approach remains to be seen.

If a chromatographic support is equipped with molecules which bind specifically with a component of a complex mixture, that component will be separated from the mixture and may be released subsequently by changing the experimental conditions (e.g. buffers, stringency, etc.) This type of separation is appropriately called affinity chromatography and remains an extremely effective and widely used separation technique. It is certainly much more selective than traditional chromatographic techniques, e.g chromatography on silica, alumina, silica or alumina coated with long-chain hydrocarbons, polysaccharide and other types of beads or gels which in order to attain their maximum separating efficiency need to be used under conditions that are damaging to biomolecules, e.g. conditions involving high pressure, use of organic solvents and other denaturing agents, etc.

The development of more powerful separation technologies depends significantly on breakthroughs in the field of materials science, specifically in the design and construction of materials that have the power to recognize specific molecular shapes under experimental conditions resembling those found in physiological media, i.e. these experimental conditions must involve an aqueous medium whose temperature and pH are close to the physiological levels and which contains none of the agents known to damage or denature biomolecules. The construction of these "intelligent" materials frequently involves the introduction of small molecules capable of specifically recognizing others into existing materials, e.g. surfaces, films, gels, beads, etc., by a wide variety of chemical modifications; alternatively molecules capable of recognition are converted to monomers and used to create the "intelligent" materials through polymerization reactions.

3. SUMMARY

A new approach to the construction of novel molecules is described. This approach involves the development of aminimide-based molecular building blocks, containing appropriate atoms and functional groups, which may be chiral and which are used in a modular assembly of molecules with tailored properties; each module contributing to the overall properties of the assembled molecule. The aminimide building blocks of the invention can be used to synthesize novel molecules designed to mimic the three-dimensional structure and function of native ligands, and/or interact with the binding sites of a native receptor. This logical approach to molecular construction is applicable to the synthesis of all types of molecules, including but not limited to mimetics of peptides, proteins, oligonucleotides, carbohydrates, lipids, polymers and to fabricated materials useful in materials science. It is analogous to the modular construction of a mechanical device that performs a specific operation wherein each module performs a specific task contributing to the overall operation of the device.

The invention is based, in part, on the following insights of the discoverer. (1) All ligands share a single universal architectural feature: they consist of a scaffold structure, made e.g. of amide, carbon-carbon, or phosphodiester bonds which support several functional groups in a precise and relatively rigid geometric arrangement. (2) Binding modes between ligands and receptors share a single universal feature as well: they all involve attractive interactions between complementary structural elements, e.g., charge- and π-type interactions, hydrophobic and Van der Waals forces, hydrogen bonds. (3) A continuum of fabricated materials exists spanning a dimensional range from 100 Å to 1 cm in diameter comprising various materials of varied construction, geometries, morphologies and functions, all of which possess the common feature of a functional surface which is presented to a biologically active molecule or a mixture of molecules to achieve recognition between the molecule (or the desired molecule in a mixture) and the surface. And (4) Aminimide structures, which have remained relatively unexplored in the design and synthesis of biologically active compounds and especially of drugs, would be ideal building blocks for constructing backbones or scaffolds bearing the appropriate functional groups, that either mimic desired ligands and/or interact with appropriate receptor binding sites; furthermore, aminimide modules may be utilized in a variety of ways across the continuum of fabricated materials described above to produce new materials capable of specific molecular recognition. These aminimide building blocks may be chirally pure and can be used to synthesize molecules that mimic a number of biologically active molecules, including but not limited to peptides, proteins, oligonucleotides, polynucleotides, carbohydrates, lipids, and a variety of polymers and fabricated materials that are useful as new materials, including but not limited to solid supports useful in column chromatography, catalysts, solid phase immunoassays, drug delivery vehicles, films, and "intelligent" materials designed for use in selective separations of various components of complex mixtures.

Working examples describing the use of aminimide-based modules in the modular assembly of a variety of molecular structures are given. The molecular structures include functionalized silica surfaces useful in the optical resolution of racemic mixtures; peptide mimetics which inhibit human elastase, protein-kinase, and the HIV protease; polymers formed via free-radical or condensation polymerization of aminimide-containing monomers; and lipid-mimetics useful in the detection, isolation, and purification of a variety of receptors.

In accordance with the objectives of the present invention, the aminimide-based molecules of interest possess the desired stereochemistry and, when required, are obtained optically pure. In addition to the synthesis of single molecular entities, the synthesis of libraries of aminimide-based molecules, using the techniques described herein or modifications thereof which are well known in the art to perform combinatorial chemistry, is also within the scope of the invention. Furthermore, the aminimide-containing molecules possess enhanced hydrolytic and enzymatic stabilities, and in the case of biologically active materials, are transported to target ligand-acceptor macromolecules in vivo without causing any serious side-effects.

4. DETAILED DESCRIPTION OF THE INVENTION

To the extent necessary to further understand any portion of the detailed description, the following earlier filed U.S. patent applications are expressly incorporated herein by reference thereto: AMINIMIDE COMPOSITIONS AND BIOLOGICALLY USEFUL DERIVATIVES THEREOF, Ser. No. 07/906,770, filed Jun. 30, 1992; AMINIMIDE-BASED SUPPORT MATERIALS AND FUNCTIONAL-IZED SURFACES, Ser. No. 07/906,769, filed Jun. 30, 1992; DIRECTED PURE CHIRAL-ISOMER LIGANDS, RECOGNITION AGENTS AND FUNCTIONALLY USEFUL MATERIALS FROM SUBSTITUTED AMINIMIDES AND DERIVATIVES CONTAINING AN ASYMMETRIC CENTER, Ser. No. 08/041,559, filed Apr. 2, 1993.

4.1 Physical and Chemical Properties of the Aminimide Functional Group

Aminimides are zwitterionic structures described by the resonance hybrid of the two energetically comparable Lewis structures shown below.

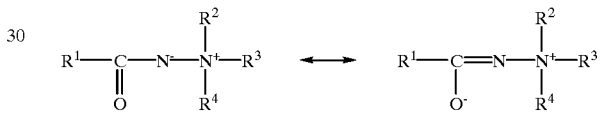

The tetrasubstituted nitrogen of the aminimide group can be asymetric rendering aminimides chiral as shown by, the two enantiomers below.

As a result of the polarity of their structures, but lack of net charge, simple aminimides are freely soluble in both water and (especially) organic solvents.

Dilute aqueous solutions of aminimides are neutral and of very low conductivity; aminimide conjugate acids are weakly acidic, $pK_a \cong 4.5$. A striking property of aminimides is their hydrolytic stability, under acidic, basic, or enzymatic conditions. For example, boiling trimethyl amine benzamide in 6 N NaOH for 24 hrs leaves the aminimide unchanged. Upon thermolytic treatment, at temperatures exceeding 180° C., aminimides decompose to give isocyanates as follows.

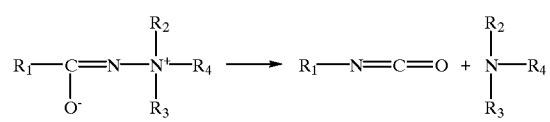

4.1.1 Use of the Aminimide Group as a Mimetic of the Amide Group

The aminimide group mimics several key structural features of the amide group, such as overall geometry (e.g. both functional groups contain a planar carbonyl unit and a tetrahedral atom linked to the acylated nitrogen) and aspects of charge distribution (e.g. both functional groups contain a carbonyl with significant negative charge development on the oxygen). These structural relationships can be seen below, where the resonance hybrids of the two groups are drawn.

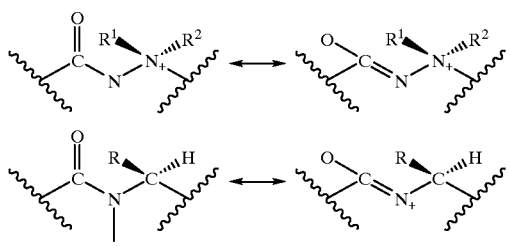

Being hydrolytically and enzymatically more stable than amides and possessing novel solubility properties due to their zwitterionic structures, aminimides are valuable building blocks for the construction of mimetics of biologically active molecules with superior pharmacological properties. For the construction of these mimetics, the aminimide backbone is used as a scaffold for the geometrically precise attachment of structural units possessing desired stereochemical and electronic features, such as suitable chiral atoms, hydrogen-bonding centers, hydrophobic and charged groups, π-systems, etc. Furthermore, multiple aminimide units can be linked in a variety of modes, using likers of diverse structures, to produce polymers of a great variety of structures. Specific molecular forms are chosen for screening and further study using several criteria. In one instance a certain aminimide structure is chosen because it is novel and has never been tested for activity as a biopharmaceutical agent or as material for device construction. In a preferable instance an aminimide ligand is chosen because it incorporates structural features and properties suggested by a certain biochemical mechanism. In another preferable case the aminimide structure is the result of assembly of molecular modules each making a specific desirable contribution to the overall properties of the aminimide-containing molecule.

Summarizing, aminimides are functional groups with unusual and very desirable physiochemical properties, which can be used as molecular modules for the construction of molecular structures that are useful as biopharmaceutical agents and as new materials for high technological applications.

4.2 General Synthetic Routes to Aminimides 4.2.1 Aminimides via Alkylation of N,N-Disubstituted Hydrazones Alkylation of an acyl hydrazide (hydrazone) followed by neutralization with a base produces an aminimide.

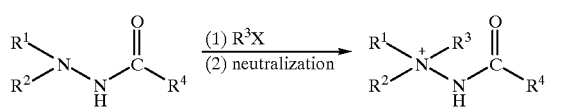

This alkylation is carried out in a suitable solvent such as a hydroxylic solvent e.g. water, ethanol, isopropanol or a dipolar aprotic solvent e.g., DMF, DMSO, acetonitrile, usually with heating.

The acyl hydrazide is produced by the reaction of a 1,1-disubstituted hydrazine with an activated acyl derivative or an isocyanate, in a suitable organic solvent, e.g. methylene chloride, toluene, ether, etc. in the presence of a base such as triethylamine to neutralize the haloacid generated during the acylation.

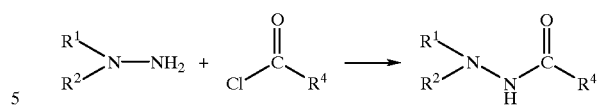

Activated acyl derivatives include acid chlorides, chlorocarbonates, chlorothiocarbonates, etc.; the acyl derivative may also be replaced with a suitable carboxylic acid and a condensing agent such as dicyclohexylcarbodiimide (DCC).

The alkylating agent $R^3X$ used in the hydrazone alkylation may be an alkyl halide (X=Cl, Br, I), a tosylate (X=OTs), or some other suitable reactive species, such as an epoxide. The conversion of phenyl isocyanate to an aminimide using the commercially available 1,1-dimethylhydrazine and ethylene oxide as the hydrazone alkylating agent is given below:

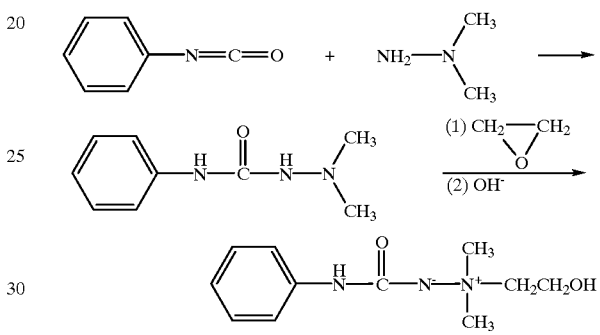

The desired 1,1-disubstituted hydrazines may be readily prepared in a number of ways well known in the art; one is the reaction of a secondary amine with $NH_2Cl$ in an inert organic solvent.

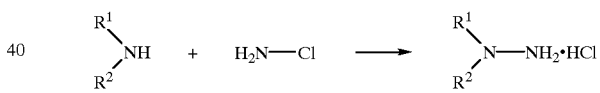

The above route to aminimides is broadly applicable and allows the incorporation of a wide variety of aliphatic, aromatic and heterocyclic groups into various positions in the aminimide structure.

4.2.2 Aminimides via Acylation of 1,1,1-Trialkyl Hydrazinium Salts

Acylation of a suitable trialkyl hydrazinium salt by an acyl derivative or isocyanate in the presence of a strong base in a suitable organic solvent, e.g. dioxane, ether, acetonitrile, etc. produces good yields of aminimides.

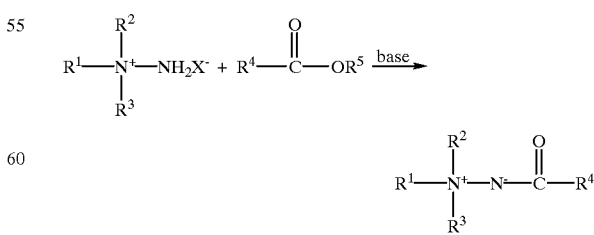

The acyl derivatives for the acylation reaction are the same as those required for the synthesis of the hydrazones outlined above.

The required hydrazinium salts may be prepared by routine alkylation of a 1,1-disubstituted hydrazines or by treatment of a tertiary amine with a haloamine (see 78 *J. Am. Chem. Soc.* 1211 (1956)).

Hydrazinium salts, being chiral at nitrogen, may be resolved, e.g. by treatment with a chiral acid followed by separation of the diastereomers (e.g. using chromatography or fractional crystallization and the resulting enantiomers used in stereoselective syntheses of aminimides.

When one of the alkyl groups in a hydrazinium salt is an ester group, the ester may be saponified efficiently using LiOH in a mixture of methanol and water, producing a useful α-hydrazinium acid after neutralization of the reaction mixture with an acid.

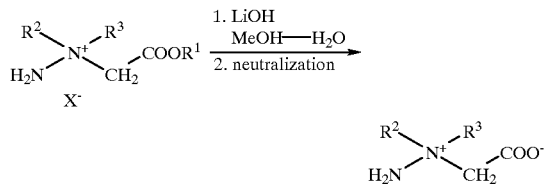

Suitably protected hydrazinium carboxylates may be used in condensation reactions to produce aminimides. Procedures analogous to those known to be useful in effecting peptide bond formation are expected to be useful; e.g. DCC or other carbodiimides may be used as condensing agents in solvents such as DMF.

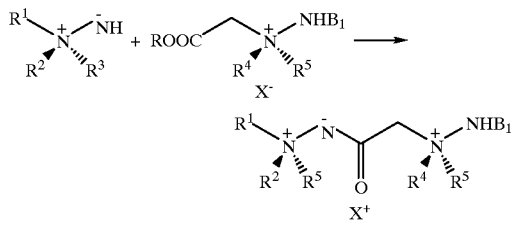

Alternatively, the hydrazinium carboxylate units may be coupled with α-amino-acids or with other nucleophiles, such as amines, thiols, alcohols, etc., using standard techniques, to produce molecules of wide utility as ligand mimetics and new materials for high technological applications.

The α-hydrazinium esters may in turn be produced by the alkylation of a 1,1-disubstituted hydrazine with a haloester under standard reaction conditions, such as those given above for the alkylation of hydrazones.

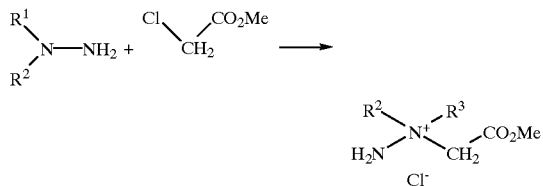

Alternatively, these hydrazinium esters may be produced by standard alkylation of the appropriate α-hydrazino ester.

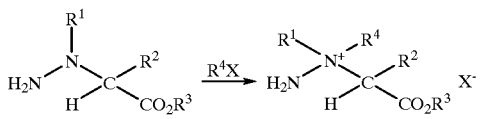

The required 1,1-disubstituted hydrazine for the above reaction may be obtained by acid or base hydrolysis of the corresponding hydrazone (see 108 *J. Am. Chem. Soc.* 6394 (1986)); the alkylated hydrazone is produced from the monosubstituted hydrazone by the method of Hinman and Flores (24 *J. Org. Chem.* 660 (1958)).

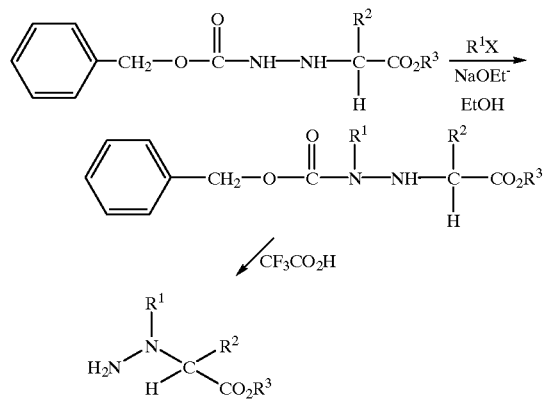

The monosubstituted hydrazones required above may be obtained by reduction of the Schiff base formed from an α-keto ester and a suitable hydrazone. This reduction may also be carried out stereoselectively, if desired, using DuPHOS-Rhodium catalysis (114 *J. Am. Chem. Soc.* 6266 (1992); 259 *Science* 479 (1993)), as shown:

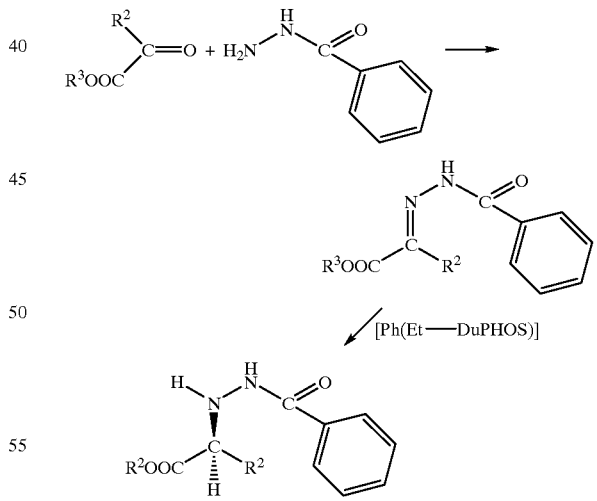

In a variation of the synthesis given above, α-halo aminimides are prepared using an α-halo acyl halide.

These halo aminimides may be reacted with nucleophiles containing reactive hydroxyl, thio, or amino groups to give complex aminimide structures.

4.2.3 Aminimides via the Hydrazine-Epoxide-Ester Reaction

A very useful and versatile synthesis of aminimides involves the one-pot reaction of an epoxide, an asymmetrically disubstituted hydrazine, and an ester in a hydroxylic solvent, usually water or an alcohol, which is allowed to proceed usually at room temperature over several hours to several days.

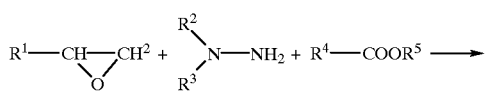

-continued

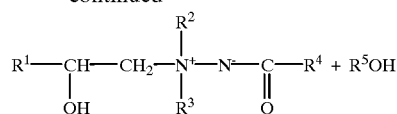

In the equation above, $R^1$, $R^2$ and $R^3$ are selected from a set of diverse structural types (e.g. alkyl, cycloalkyl, aryl, aralkyl, alkaryl or many substituted versions thereof), and $R^4$ and $R^5$ are alkyl or cycloalkyl.

The rates for the above reaction increase with increasing electrophilicity of the ester component. Generally, a mixture of 0.1 mol of each of the reactants in 50–100 ml of an appropriate solvent is stirred for the required period at room temperature (the reaction may be monitored by thin layer chromatography). At the end of this period the solvent is removed in vacuo to give the crude product.

If substituent $R^4$ of the ester component in the above aminimide formation contains a double bond, an aminimide with a terminal double bond results which may be epoxidized, e.g. using a peracid under standard reaction conditions, and the resulting epoxide used as starting material for a new aminimide formation; thus a structure containing two aminimide subunits results. If the aminimide-formation and epoxidation sequence is repeated n times, a structure containing n aminimide subunits results; thus for $R^4$=propene, n repetition of the sequence results in the structure shown below:

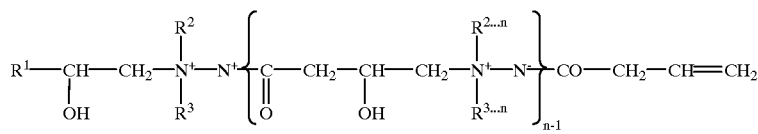

where the designations $R^2$ and $R^3$ are used to illustrate the manner in which the hydrazine substituents $R^2$ and $R^3$ can be varied in each polymerization step to produce oligomers or polymers of diverse structures.

A related aminimide polymerization sequence utilizes an ester moiety bonded directly to the epoxide group.

An additional related polymerization sequence involves the use of bifunctional epoxides and esters of the following form

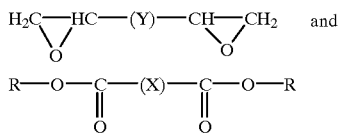

so as to produce polymers of the following structure (shown for the case of reaction with dimethyl hydrazine):

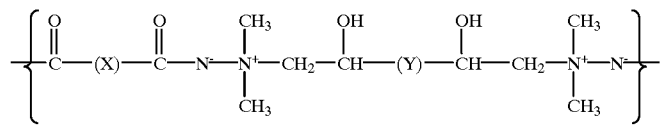

where X and Y are alkyl, cycloalkyl, aryl, aralkyl or alkaryl linkers.

4.2.4 Synthesis of Enantiomerically-Pure Aminimides

Enantiomerically-pure aminimides may be produced by acylation of chiral hydrazinium salts as shown in the example below.

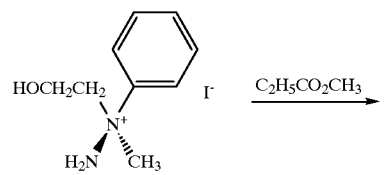

Chirally-pure hydrazinium salts may be obtained by resolution of the racemates; resolution can be effected by forming salts with optically pure acids, e.g. tartaric acid, and separating the resulting diastereomers by means of chromatography or fractional crystallization (see, e.g., 103 *J. Chem. Soc.* 604 (1913)); alternatively the racemic modification is resolved by subjecting it to chromatographic separation using a chiral stationary chromatographic support, or if feasible, by the use of a suitable enzyme system.

Alternatively, enantiomerically-pure aminimides may be obtained by resolution of the racemic modifications using one of the techniques described above for the resolution of racemic hydrazinium salts (for an example, see 28 *J. Org. Chem.* 2376 (1963)).

An additional approach to the synthesis of chiral aminimides involves chiral synthesis; an example is provided by the reaction of (S)-(−)-propylene oxide with 1,1-dimethylhydrazine and methyl-(R)-3-hydroxy-butyrate, all of which are commercially available.

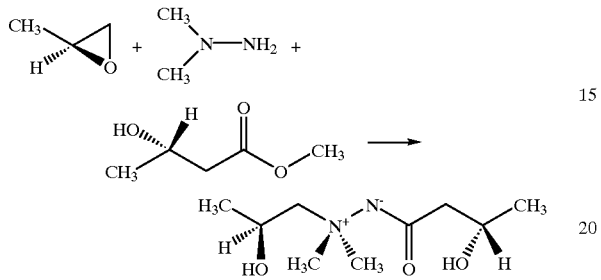

A variety of chiral epoxides, produced by chiral epoxidations such as those developed by Sharpless (Asynn. Syn., J. D. Morrison ed., Vol. 5, Ch. 7+8, Acad. Press, New York, N.Y., 1985), and chiral esters, produced by standard procedures, may be used to produce a wide variety of chiral aminimides.

Chirally-pure aminimide molecular building blocks are especially preferred since they will be used to produce a vast array of molecules useful as new materials for high technological applications and as molecular recognition agents, including biological ligand mimetics to be used as drugs, diagnostics, and separation agents.

4.4 Synthesis of Specific Classes of Aminimides 4.4.1 Synthesis of Chiral Aminimide-Containing Conjugates The synthetic routes outlined above may be utilized to produce a wide variety of chiral aminimide conjugates of the following general structure:

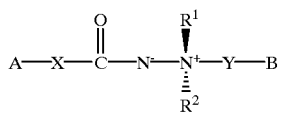

The substituents A and B shown may be of a variety of structures and may differ markedly in their physical or functional properties, or may be the same; they may also be chiral or symmetric. A and B are preferably selected from 1) amino acid derivatives of the form (AA)N, which would include, for example, natural and synthetic amino acid residues (N=1) including all of the naturally occurring alpha amino acids, especially alanine, arginine, asparagnine, aspartic acid, cysteine, glutamine, glutamic acid, glycine, histidine, isoleucine, leucine, lysine, methionine, phenylalanine, proline, serine, threonine, tryptophan, tyrosine; the naturally occurring distributed amino acids, such as amino isobutyriz acid, and isovaline, etc.; a variety of synthetic amino acid residues, including alpha-disubstituted variants, species with olefinic substitution at the alpha position, species having derivatives, variants or mimetics of the naturally occurring side chains; N-substituted glycine residues; natural and synthetic species known to functionally mimic amino acid residues, such as statine, bestatin, etc. Peptides (N=2–30) constructed from the amino acids listed above, such as angiotensinogen and its family of physiologically important angiotensin hydrolysis products, as well as derivatives, variants and mimetics made from various combinations and permutations of all the natural and synthetic residues listed above. Polypeptides (N=31–70), such as big endothelin, pancreastatin, human growth hormone releasing factor and human pancreatic polypeptide. Proteins (N>70) including structural proteins such as collagen, functional proteins such as hemoglobin, regulatory proteins such as the dopamine and thrombin receptors.

2) a nucleotide derivative of the form (NUCL)N, which includes natural and synthetic nucleotides (N=1) such as adenosine, thymine, guanidine, uridine, cystosine, derivatives of these and a variety of variants and mimetics of the purine ring, the sugar ring, the phosphate linkage and combinations or some of all of these. Nucleotide probes (N=2–25) and oligonucleotides (N>25) including all of the various possible homo and heterosynthetic combinations and permutations of the naturally occurring nucleotides, derivatives and variants containing synthetic purine or pyrimidine species or mimics of these, various sugar ring mimetics, and wide variety of alternate backbone analogues including but not limited to phosphodiester, phosphorothionate, phosphorodithionate, phosphoramidate, alkyl phosphotriester, sulfamate, 3'-thioformacetal, methylene(methylimino), 3-N-carbamate, morpholino carbamate and peptide nucleic acid analogues.

3) a carbohydrate derivative of the form (CH)n. This would include natural physiologically active carbohydrates such as including related compounds such as glucose, galactose or sialic acids, beta-D-glueasylamine and nojorimycin which are both inhibitors of glucosidase, pseudo sugars, such as 5a-carba-2-D-galactopyranose, which is known to inhibit the growth of Klebsiella pneumonia (n=1), synthetic carbohydrate residues and derivatives of these (n=1) and all of the complex oligomeric permutations of these found in nature, including high mannose oligosaccharides, the known antibiotic streptomycin (n>1).

4) a naturally occurring or synthetic organic structural motif. This term is defined as meaning an organic molecule having a specific structure that has biological activity, such as having a complementary structure to an enzyme, for instance. This term includes any of the well known base structures of pharmaceutical compounds including pharmacophores or metabolites thereof. These include beta-lactams, such as penicillin, known to inhibit bacterial cell wall biosynthesis; bidenzazepines, known to bind to CNS receptors, used as antidepressants; polyketide macrolides, known to bind to bacterial ribosymes, etc. These structural motifs are generally known to have specific desirable binding properties to ligand acceptors.

5) a reporter element such as a natural or synthetic dye or a residue capable of photographic amplification which possesses reactive groups which may be synthetically incorporated into the aminimide structure or reaction scheme and may be attached through the groups without adversely interfering with the reporting functionality of the group. Preferred reactive groups are amino, thio, hydroxy, carboxylic acid, carboxylic acid ester, particularly methyl ester, acid chloride, isocyanate alkyl halides, aryl halides and oxirane groups.

6) an organic moiety containing a polymerizable group such as a double bond or other functionalities capable of undergoing condensation polymerization or copolymerization. Suitable groups include vinyl groups, oxirane groups, carboxylic acids, acid chlorides, esters, amides, lactones and lactams. Other organic moiety such as those defined for R and R' may also be used.

7) a macromolecular component, such as a macromolecular surface or structures which may be attached to the aminimide modules via the various reactive groups outlined above in a manner where the binding of the attached species to a ligand-receptor molecule is not adversely affected and the interactive activity of the attached functionality is determined or limited by the mmacromolecule. This includes porous and non-porous inorganic macromolecular components, such as, for example, silica, alumina, zirconia, titania and the like, as commonly used for various applications, such as normal and reverse phase chromatographic separations, water purification, pigments for paints, etc.; porous and non-porous organic macromolecular components, including synthetic components such as styrene-divinyl benzene beads, various methacrylate beads, PVA beads, and the like, commonly used for protein purification, water softening and a variety of other applications, natural components such as native and functionalized celluloses, such as, for example, agarose and chitin, sheet and hollow fiber membranes made from nylon, polyether sulfone or any of the materials mentioned above. The molecular weight of these macromolecules may range from about 1000 Daltons to as high as possible. They may take the form of nanoparticles (dp=100–1000 Angstroms), latex particles (dp=1000–5000 Angstroms), porous or non-porous beads (dp=0.5–1000 microns), membranes, gels, macroscopic surfaces or functionalized or coated versions or composites of these.

A and/or B may be a chemical bond to a suitable organic moiety, a hydrogen atom, an organic moiety which contains a suitable electrophilic group, such as an aldehyde, ester, alkyl halide, ketone, nitrile, epoxide or the like, a suitable nucleophilic group, such as a hydroxyl, amino, carboxylate, amide, carbanion, urea or the like, or one of the R groups defined below. In addition, A and B may join to form a ring or structure which connects to the ends of the repeating unit of the compound defined by the preceding formula or may be separately connected to other moieties.

A more generalized structure of the composition of this invention is defined by the following formula:

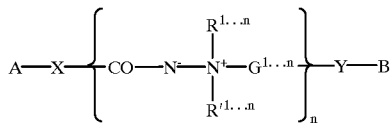

wherein:
a. at least one of A and B are as defined above and A and B are optionally connected to each other or to other compounds;
b. X and Y are the same or different and each represents a chemical bond or one or more atoms of carbon, nitrogen, sulfur, oxygen or combinations thereof;
c. R and R' are the same or different and each represents B, cyano, nitro, halogen, oxygen, hydroxy, alkoxy, thio, straight or branched chain alkyl, carbocyclic aryl and substituted or heterocyclic derivatives thereof, wherein R and R' may be different in adjacent n units and have a selected stereochemical arrangement about the carbon atom to which they are attached;
d. G is a chemical bond or a connecting group that includes a terminal carbon atom for attachment to the quaternary nitrogen and G may be different in adjacent n units; and
e. $n \geq 1$.

Preferably, if G is a chemical bond, Y includes a terminal carbon atom for attachment to the quaternary nitrogen; and if n is 1 and X and Y are chemical bonds, R and R' are the same, A and B are different and one is other than H or R.

As used herein, the phrase linear chain or branched chained alkyl groups means any substituted or unsubstituted acyclic carbon-containing compounds, including alkanes, alkenes and alkynes. Alkyl groups having up to 30 carbon atoms are preferred. Examples of alkyl groups include lower alkyl, for example, methyl, ethyl, n-propyl, isopropyl, n-butyl, isobutyl or tert-butyl; upper alkyl, for example, cotyl, nonyl, decyl, and the like; lower alkylene, for example, ethylene, propylene, propyldiene, butylene, butyldiene; upper alkenyl such as 1-decene, 1-nonene, 2,6-dimethyl-5-octenyl, 6-ethyl-5-octenyl or heptenyl, and the like; alkynyl such as 2-ethynyl, 2-butynyl, 1-pentynyl and the like. The ordinary skilled artisan is familiar with numerous linear and branched alkyl groups, which are within the scope of the present invention.

In addition, such alkyl group may also contain various substituents in which one or more hydrogen atoms has been replaced by a functional group. Functional groups include but are not limited to hydroxyl, amino, carboxyl, amide, ester, ether, and halogen (fluorine, chlorine, bromine and iodine), to mention but a few. Specific substituted alkyl groups can be, t-or example, alkoxy such as methoxy, ethoxy, butoxy, pentoxy and the like, polyhydroxy such as 1,2-dihydroxypropyl, 1,4-dihydroxy-1-butyl , and the like; methylamino, ethylamino, dimethylamino, diethylamino, triethylamino, cyclopentylamino, benzylamino, dibenzylamino, and the like; propanoic, butanoic or pentanoic acid groups, and the like; formamido, acetamido, butanamido, and the like, methoxycarbonyl, ethoxycarbonyl or the like, chloroformyl, bromoformyl, 1,1-chloroethyl, bromo ethyl and the like, or dimethyl or diethyl ether groups or the like.

As used herein, substituted and unsubstituted carbocyclic groups of up to about 20 carbon atoms means cyclic carbon-containing compounds, including but not limited to cyclopentyl, cyclohexyl, cycloheptyl, admantyl, and the like, such cyclic groups may also contain various substituents in which one or more hydrogen atoms has been replaced by a functional group. Such functional groups include those described above, and lower alkyl groups as described above. The cyclic groups of the invention may further comprise a heteroatom. For example, in a specific embodiment, $R_2$ is cycohexanol.

As used herein, substituted and unsubstituted aryl groups means a hydrocarbon ring bearing a system of conjugated double bonds, usually comprising an even number of 6 or more (pi) electrons. Examples of aryl groups include, but are not limited to, phenyl, naphthyl, anisyl, toluyl, xylenyl and the like. According to the present invention, aryl also includes aryloxy, aralkyl, aralkyloxy and heteroaryl groups, e.g., pyrimidine, morpholine, piperazine, piperidine, benzoic acid, toluene or thiophene and the like. These aryl groups may also be substituted with any number of a variety of functional groups. In addition to the functional groups described above in connection with substituted alkyl groups and carbocylic groups, functional groups on the aryl groups can be nitro groups.

As mentioned above, $R_2$ can also represent any combination of alkyl, carbocyclic or aryl groups, for example, 1-cyclohexylpropyl, benzylcyclohexylmethyl, 2-cyclohexyl-propyl, 2,2-methylcyclohexylpropyl, 2,2-methylphenylpropyl, 2,2-methylphenylbutyl, and the like.

In one embodiment of the invention, at least one of A and B represent an organic or inorganic macromolecular surface. Examples of preferred macromolecular surfaces include ceramics such as silica and alumina, porous and nonporous beads, polymers such as a latex in the form of beads, membranes, gels, macroscopic surfaces or coated versions or composites or hybrids thereof. This functionalized surface may be represented as follows:

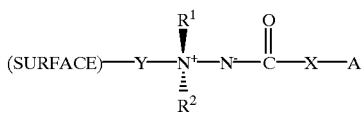

In a further embodiment of the invention, the above roles of A and B are reversed, so that B is the substituent selected from the foregoing list and A represents a functionalized surface, as shown below:

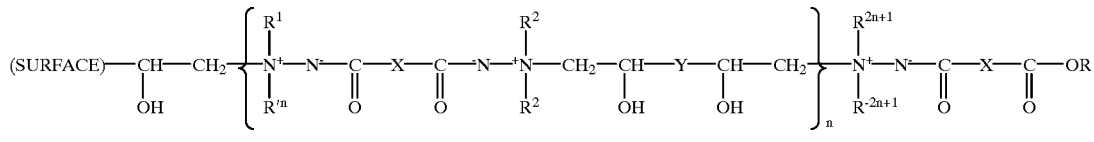

or

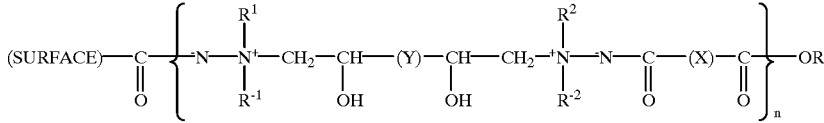

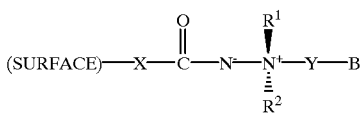

In a third preferred embodiment of the invention, either A, B, or both contain one or more double bonds capable of undergoing free-radical polymerization or copolymerization to produce achiral or chiral oligomers, polymers, copolymers, etc.

Another embodiment of the invention relates to a composition having the structure

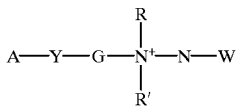

wherein A, Y, R, $R^1$ and G are as defined above and
W is —H
or —$H_2X^-$ where $X^-$ is an anion, such as a halogen or tosyl anion.

Yet another aspect of the invention relates to a lipid mimetic composition having the structure

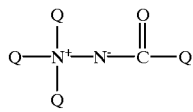

wherein Q is a chemical bond; an electrophilic group; a nucleophilic group; R; an amino acid derivative; a nucleotide derivative; a carbohydrate derivative; an organic structural motif; a reporter element; an organic moiety containing a polymerizable group; a macromolecular component; or the substituent X(T) or X(T)$_2$; wherein R is an alkyl, cycloalkyl, aryl, aralkyl or alkaryl group or a substituted or heterocyclic derivative thereof, and T is a linear or branched hydrocarbon having between 12 and 20 carbon atoms some of which are optionally substituted with oxygen, nitrogen or sulfur atoms or by an aromatic ring; and provided that at least two T substituents are present in the structure of the composition.

In the description that follows, $R^n$ where n is an integer will be used to designate a group from the definition of R and $R^1$.

Another aspect of the invention relates to functionalized polymers having the structure:

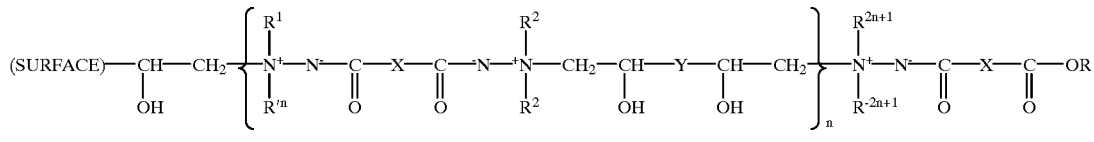

wherein
a. X and Y are connecting groups;
b. $R^n$ or $R'^n$ (where n=an integer) each represent alkyl, cycloalkyl, aryl, aralkyl and alkaryl;
c. (STRUCTURE) is a macromolecular component; and
d. n≧1.

The invention also contemplates various methods of producing an aminimide-functional support. One method comprises the steps of reacting a polymer or oligomer containing pendant moieties of OH, NH or SH with a compound of the formula:

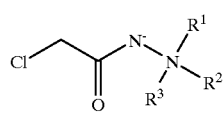

wherein $R^1$ and $R^2$ each represent alkyl, cycloalkyl, aryl, aralkyl or alkaryl, and $R^3$ is an amino acid derivative; a nucleotide derivative; a carbohydrate derivative; an organic structural motif; a reporter element; an organic moiety containing a polymerizable group; or a macromolecular component;

coating the reacted polymer or oligomer onto a support to form a film thereon; and heating the coated support to crosslink the film.

Another method comprises the steps of coating a mixture of multifunctional esters and multifunctional epoxides onto a support to form a film thereon; and reacting the coated support with 1,1'-dialkylhydrazine to crosslink the film.

A third method comprises the steps of coating a mixture of an aminimide-functional vinyl monomer, a difunctional vinyl monomer and a vinyl polymerization initiator onto a support to form a film thereon; and heating the coating support to form a crosslinked film.

The aminimide-functionalized support prepared according to the previous methods are another aspect of the invention.

The ability to derivatize an aminimide scaffold in numerous ways using the synthetic techniques outlined above as well as those given below, offers a vast array of structures capable of recognizing specific molecular entities via establishment of specific types of binding interactions. Thus the aminimide shown below is in principle capable of establishing the following interactions: π-stacking involving the phenyl group; hydrogen bonds; acid-base interactions involving the anionic nitrogen; salt bridges involving the quarternary nitrogen; steric interactions with the bulky isopropyl substituent; and hydrophobic interactions involving the hydrocarbon chain.

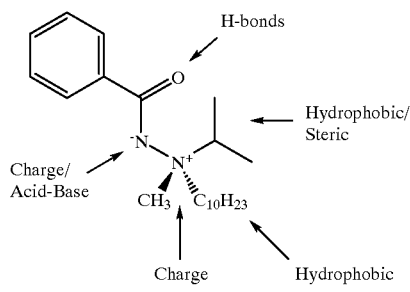

As a further example, possible interactions between a recognition target and a specific supported aminimide are shown below. Experimental procedures for the synthesis of specific chiral aminimides are given below.

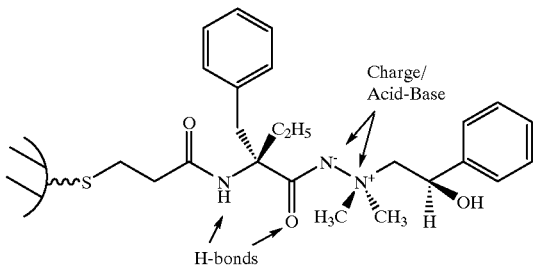

4.4.2 Sequential Catenation of Aminimide Subunits Producing Sequences of Various Sizes By choosing aminimide building blocks possessing functional groups capable of establishing predictable binding interactions with target molecules, and using synthetic techniques such as those broadly described above to effect catenation (linking) of the building blocks, it is possible to construct sequences of aminimide subunits mimicking selected native oligomers or polymers, e.g. peptides and polypeptides, which have better stability and pharmacokinetic properties than those of the native sequencers. Specific syntheses of multisubunit aminimides are outlined below.

4.4.2.1 Catenation of Aminimide Subunits via Alkylation/Acylation Cycles

The following steps are involved in this synthesis:

1. Acylation of a chiral hydrazinium salt, prepared as described above, with a molecule capable of functioning both as an acylating and as an alkylating agent producing an aminimide; BrCH$_2$COCl and other bifunctional species, such as bromoalkyl isocyanates, 2-bromoalkyl oxazolones, etc., may be used as acylating agents under the reaction conditions given above.

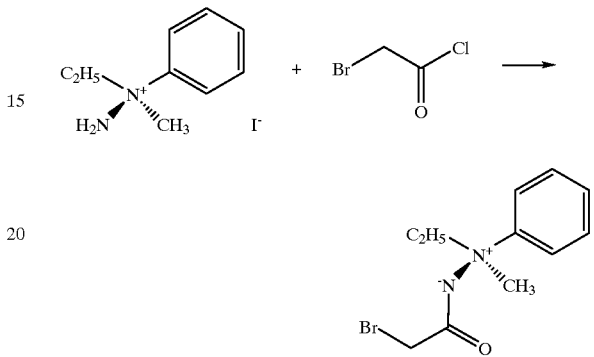

2. Reaction of the product of the above reaction with an asymmetrically disubstituted hydrazine to form a diastereomeric mixture of aminimide hydrazinium salts under reaction conditions similar to those described above.

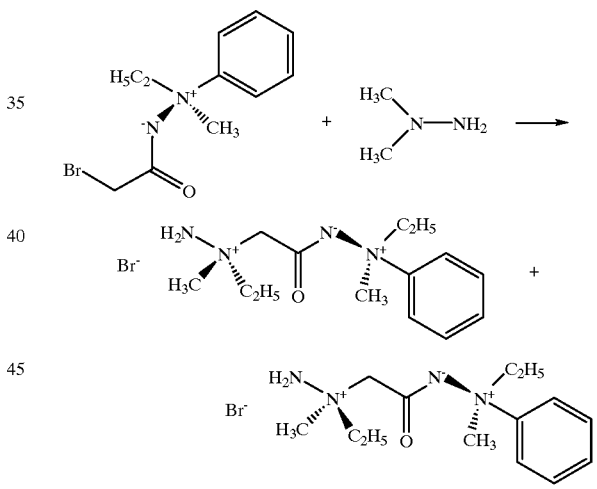

3. Isolation of the diastereomers produced in step 2 as described above, e.g. by fractional crystallization or by chromatography using techniques familiar to those skilled in the art.

4. Acylation of the desired diastereomer from step 3 with a bifunctional acyl derivative similar to those listed in step 1 above producing a dimeric type structure.

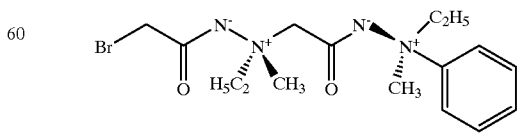

5. Repetition of steps 2, 3 and 4 the required number of times to build the desired aminimide subunit sequence.

6. Capping of the assembled sequence if desired, for example, by reaction with an acylating agent, such as acetyl chloride.

The experimental conditions (e.g. reaction-solvent, temperature and time, and purification procedures for products) for all of the above reactions were described above and are also well-known and practiced in the art. As the molecular weight of the products increases (e.g. in step 5 above) solubility and reaction-rate problems may develop if the reactions are run under the conditions that successfully gave products of much smaller molecular weight. As is well known from the art of peptide synthesis, this is probably due to conformational (folding) effects and to aggregation phenomena, and procedures found to work in the related peptide cases are expected to be very useful in the case of aminimide catenations. For example, reaction solvents such as DMF, or N-methyl pyrollidone, and chaotropic (aggregate-breaking) agents, such as urea, are expected to be helpful in alleviating reactivity problems as the molecular-weight of the product increases.

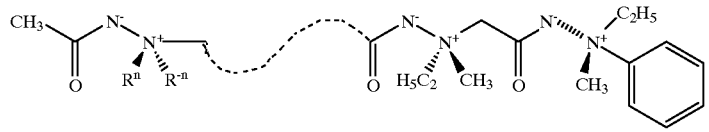

4.4.2.2 Catenation of Aminimide Subunits via Acylation/Alkylation Cycles

The following steps are involved in this synthesis; experimental conditions for running the reactions are given above.

1. Alkylation of an asymmetrically disubstituted acyl hydrazide, prepared as outlined above, with a molecule capable of functioning both as an alkylating and an acylating agent to form a racemic mixture of aminimides; as before the use of $BrCH_2COCl$ is shown below, but other bifunctional species, such as bromoalkyl isocyanates, 2-bromoalkyl oxazolones, etc. may also be used.

2. Reaction of the racemate from above with an asymmetrically disubstituted hydrazine to form the hydrazone:

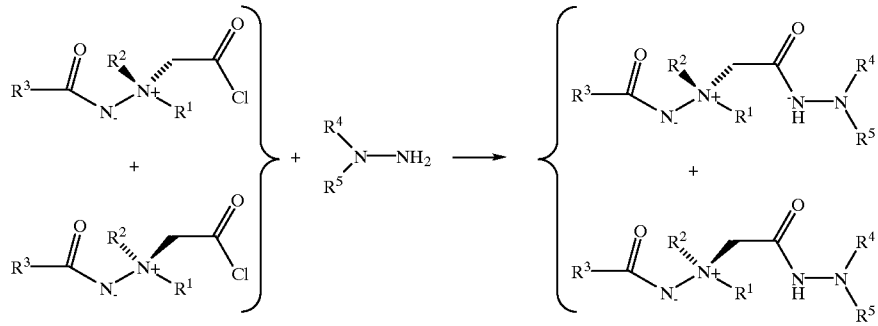

3. Resolution of the racemic modification from the previous step as described above.

4. Alkylation of the product from step 3 with a bifunctional molecule capable of alkylation and acylation, which may be the same as that used in step 1 or different, to form a mixture of diastereomeric aminimides.

5. Reaction of the diastereomers from step 4 with a suitable asymmetrically disubstituted hydrazine to form the diastereomeric hydrazones, as shown:

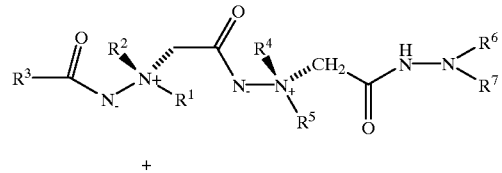

+

-continued

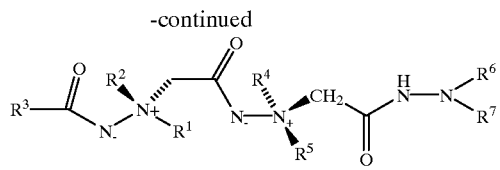

6. Separation of the diastereomers as described above.

7. Repetition of steps 4, 5 and 6 to build the desired sequence of aminimide subunits.

8. Capping of the sequence, if desired, using e.g. methyl bromide to produce a sequence such as shown below.

4.4.2.3 Catenation of Aminimide Subunits Using Hydrazinolysis of an Ester in the Presence of an Epoxide The following steps are involved in this synthesis; experimental conditions for running the reactions are given above.

1. Formation of an aminimine from the reaction of an 1,1-asymmetrically disubstituted hydrazine with an epoxide; the reaction is illustrated for a chiral epoxide below (the chiral epoxide may be obtained by e.g. a Sharples epoxidation):

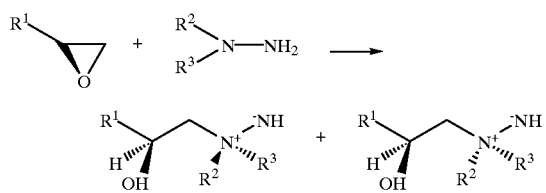

The aminimine is normally not isolated, but used directly for the following reaction.

2. The aminimine is reacted-with an ester-epoxide to give an aminimine; for the mixture of diastereomeric aminimides above and the ester-epoxide shown below, the following is obtained.

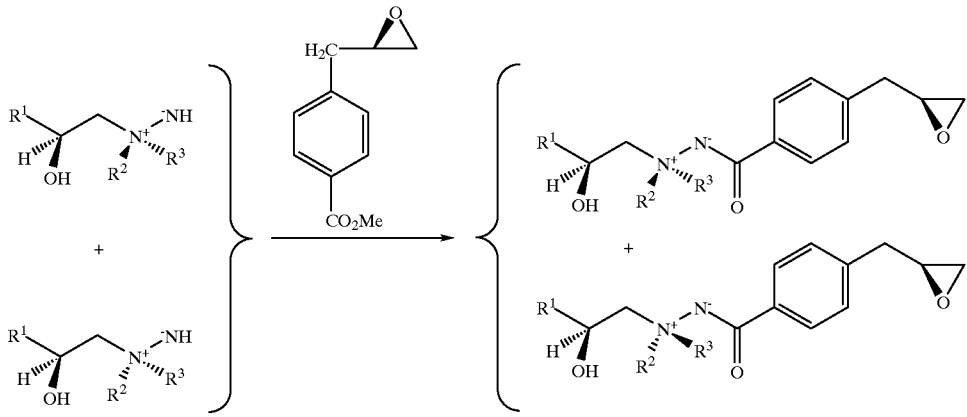

3. Separation of the diastereomeric aminimides as described above.

4. Reaction of the desired diastereomeric aminimide with an asymmetrically disubstituted hydrazine to form diastereomeric aminimide-aminimines:

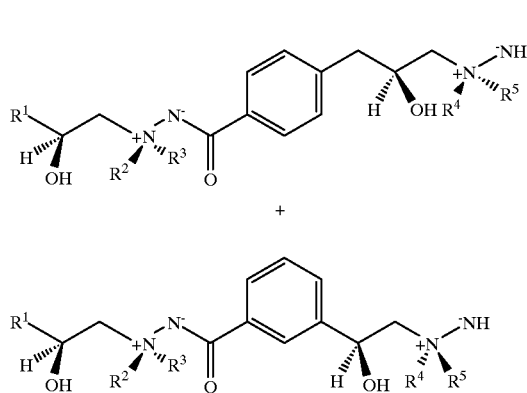

5. Repetition of steps 2, 3 and 4 above using the appropriate hydrazines and epoxy-esters in each step to produce the desired aminimide sequence.

6. "Capping" of the final sequence, if desired, by acylation with a simple ester, such as methyl acetate, to produce the designed aminimide ligand shown:

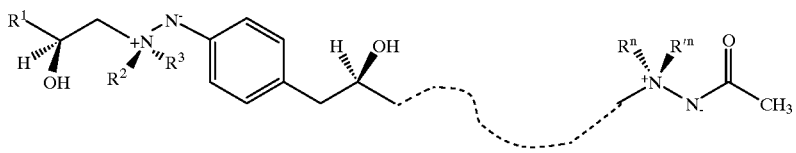

4.4.2.4 Catenation of α-Hydrazinium Esters or Carboxylic Acids

The following steps are involved in this synthesis; experimental conditions for running the reaction are given above.

1. Treatment of a chirally-pure hydrazinium salt (produced as described above) with a strong base, such as NaOMe in an alcohol solvent, to form the imino anion:

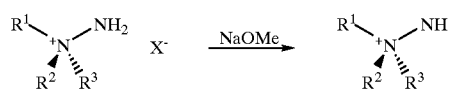

2. Addition of an α-hydrazinium ester (again produced as discussed above) to an appropriately blocked imino-anion-containing mixture from step 1 to form the hydrazinium-aminimide, as shown.

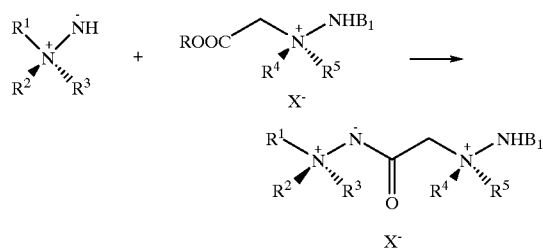

In the equation above, B1 is an appropriate protecting group such as BOC (t-butoxy carbonyl.

3. Removal of B1 followed by repetition of steps 1 and 2 the required number of times to obtain the desired aminimide sequence, followed by a "capping" step, using a simple ester as acylating agent.

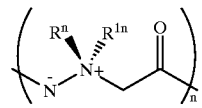

Alternatively, the α-hydrazinium carboxylic acids may be obtained by treatment of the esters with LiOH in MeOH/H$_2$O at room temperature, as described above, and coupled with each other using condensation reactions promoted by DCC or other agents. Protecting groups used in traditional peptide synthesis are expected to be useful here as well.

4.4.3 Synthesis of Aminimide-Containing Peptides and Proteins

Aminimide subunits may be introduced into any position of a polypeptide via chemical synthesis, using one of the procedures outlined above, including the techniques for dealing with problematic reactions of high molecular weight species. The resulting hybrid molecules are expected to have improved properties over the native molecules; for example, the aminimide group may confer greater hydrolytic and enzymatic stability to the hybrid molecule over its native counterpart.

As an example of a synthesis of an aminimide-modified peptide, the modification of a peptide attached to a Merrifield solid phase synthesis support by alkylation with aminimide-containing molecule is shown below.

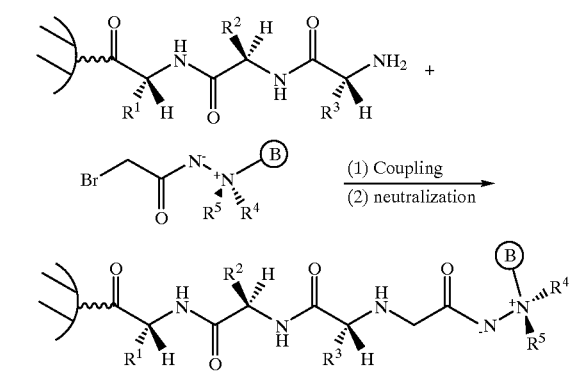

If moiety B contains a functional group which can be used to link additional aminimide and natural or unnatural amino acid subunits, e.g. via acylation reactions, complex hybrid structures may be obtained using the experimental procedures outlined above.

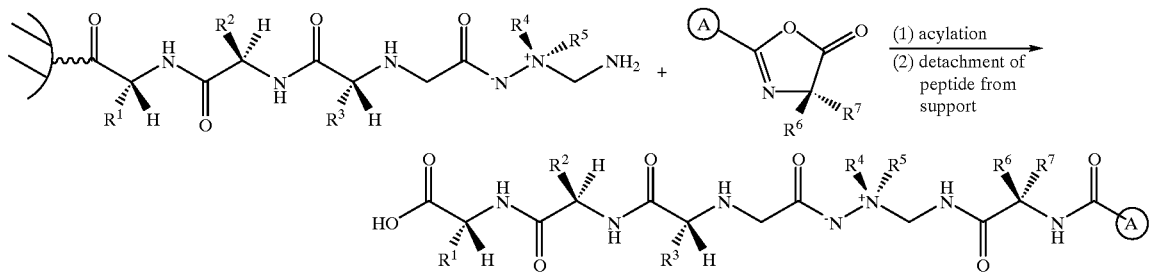

4.4.4 Synthesis and Polymerization of Chiral Aminimide-Containing Monomers

The conversion of many of the aminimide structures described above into monomer building blocks which can be polymerized to give novel macromolecules, which are useful in a variety of high technological applications, is contemplated. The following synthetic approaches are expected to be very useful in the production of new materials.

(a) Free-Radical Polymerization of Vinyl Aminimides

Chiral (as well as achiral) vinylaminimide monomers of the general structures shown below may be readily prepared, following the procedures outlined above, and used in free-radical polymerizations, according to experimental procedures well-known in the art, to produce a vast array of novel polymeric materials.

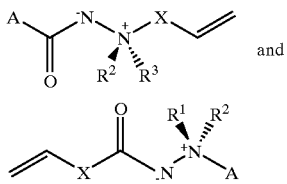

Additional monomeric structures useful in preferred free radical polymerizations include those shown below; they produce polymeric chains capable of being crosslinked into more rigid structures. The monomers shown below may be prepared using the synthetic procedures outlined above, and the polymerization/crosslinking reactions may be run using standard polymerization techniques. See, for example, *Practical Macromolecular Organic Chemistry*, Braun, Cherdron and Kern, trans. by K. Ivin, 3ed., Vol Z, Harwood Academic Publishers, New York, N.Y. 1984.

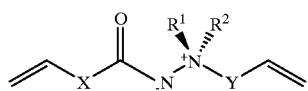

The monomers shown above may be polymerized with other alkenes or dienes, which are either commercially available or readily prepared using standard synthetic reactions and techniques, to furnish copolymers with novel structures and molecular recognition characteristics.

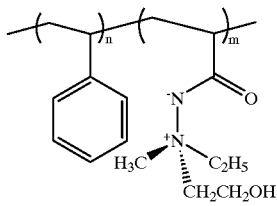

(b) Condensation Polymerizations Producing Aminimide-Containing Macromolecules

Sequential condensations of aminimide-forming molecules may be used to produce a variety of novel polymers of controlled size. An example involving dimeric epoxides and esters is given below; processes involving trimeric and more complex epoxides and esters are also contemplated; and experimental conditions for running these polymerizations (including techniques for resolving experimental difficulties as product molecular weight increases) have been described above.

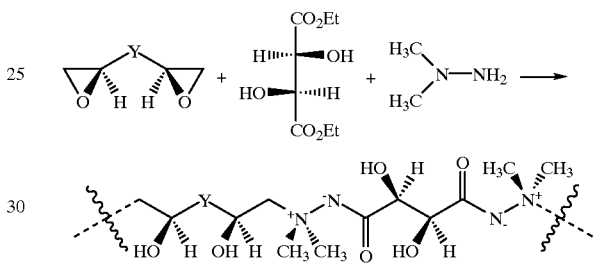

When the polymerization reaction is carried out with molecules immobilized on a support, e.g. silica, a support capable of specific molecular recognition is produced; an example of such a support is given below:

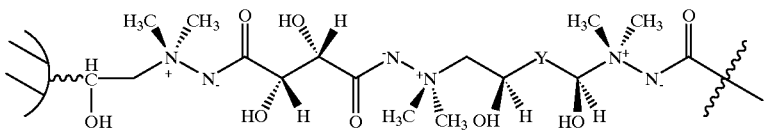

4.4.5 Lipid Mimetics

Aminimide conjugate structures containing two long-chain alkyl groups capable of producing bilayer membrane structures are preferred embodiments of the present invention. Many uses of these amphiphilic, surface-active compounds are envisioned. They may be used to isolate and stabilize biologically-active molecules from the cell-wall; they are useful in the construction of affinity chromatography supports for the isolation and purification of amphiphilic macromolecules, e.g. receptors, enzymes, etc.; and they may serve as effective delivery systems for the administration of drugs.

The structure of one preferred lipid mimetic is shown below. Substituents R may be chosen from a variety of structures of various sizes including structures of ligands of biological receptors or enzymes; a preferred combination of substituents involves sterically small groups for $R_1$ and $R_2$ and a group such as A or B described above for $R_3$; the long-chain alkyl groups are 4–20 carbons in length; group X is a linker composed of atoms chosen from the set of C, H, N, O, and S.

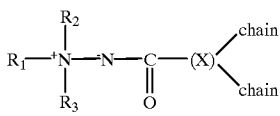

A further desirable variation of the surface-active structure shown above is as follows:

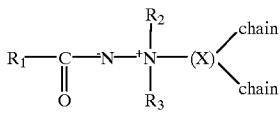

In the above structure, X is a linker group (e.g. CH); one or more substituents R are chosen from the group of structures A and B described above and the remaining substituent(s) in preferably a sterically small group, e.g. H, or $CH_3$. An additional desirable amphiphilic structure is shown below; substituent structures are similar to those listed above.

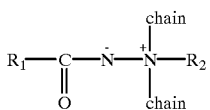

An example of a synthesis of a lipid mimetic is given below; the required experimental conditions for the reactions that follow are similar to those described above for related transformations.

Thus,

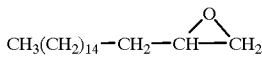

is combined with $(CH_3)_2NNH_2$ and $CH_3COOCH_3$ to produce $CH_3(CH_2)_{14}CH_2CH(OH)CH_2N(CH_3)_2NCOCH_3$, which is then combined with $CH_3(CH_2)_{14}CH_2Br$ under alklaline conditions to produce:

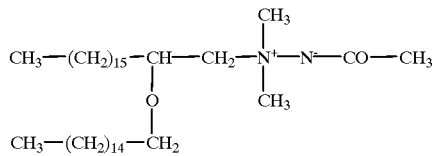

4.4.6 Fabrication of Aminimide-Containing Macromolecular Structures Capable of Specific Molecular Recognition In an embodiment of the invention aminimide molecular building blocks may be utilized to construct new macromolecular structures capable of recognizing specific molecules ("intelligent macromolecules"). The "intelligent macromolecules" may be represented by the following general formula:

P-C-L-R where,
R is a structure capable of molecular recognition;
L is a linker;
P is a macromolecular structure serving as a supporting platform;
C is a polymeric structure serving as a coating which surrounds P.

Structure R may be a native ligand or a biological ligand-acceptor or a mimetic thereof, such as those described above.

Linker L may be a chemical bond or one of the linker structures listed above, or a sequence of subunits such as amino acids, aminimide monomers, oxazolone-derived chains of atoms, etc.

Polymeric coating C may be attached to the supporting platform either via covalent bonds or "shrink wrapping," i.e. the bonding that results when a surface is subjected to coating polymerization well known to those skilled in the art. This coating element may be
1) a thin crosslinked polymeric film 10–50 Å in thickness;
2) a crosslinked polymeric layer having controlled microporosity and variable thickness, or
3) a controlled microporosity gel. When the support platform is a microporous particle or a membrane, as described below, the controlled microporosity gel may be engineered to completely fill the porous structure of the support platform. The polymeric coatings may be constructed in a controlled way by carefully controlling a variety of reaction parameters such as the nature and degree of coating crosslinking, polymerization initiator, solvent, concentration of reactants, and other reaction conditions, such as temperature, agitation, etc., in a manner that is well known to those skilled in the art.

The support platform P may be a pellicular material having a diameter (dp) from 100 Å to 1000μ, a latex particle (dp 0.1–0.2μ), a microporous bead (dp 1–1000μ), a porous membrane, a gel, a fiber, or a continuous macroscopic surface. These may be commercially available polymeric materials, such as silica, polystyrene, polyacrylates, polysulfones, agarose, cellulose, etc. or synthetic aminimide-containing polymers such as those described below.

Any of the elements P, C, L, or R containing an aminimide-based structure is derived from a form of the element containing a precursor to the aminimide-based structure. The multisubunit recognition agents above are expected to be very useful in the development of targeted therapeutics, drug delivery systems, adjuvants, diagnostics, chiral selectors, separation systems, and tailored catalysts.

In the present specification the terms "surface", "substrate", and "structure" refer to either P, P linked to C or P linked to C and L as defined above.

Thus, another aspect of the invention relates to a three-dimensional crosslinked random copolymer containing, in copolymerized form about 1 to 99 parts of a free-radically polymerizable monomer containing an aminimide group; up to 98 parts of a free-radically addition-polymerizable comonomer; and about 1 to 50 parts of at least one crosslinking monomer.

The comonomer used in this copolymer may be water-soluble or water-insoluble, and the copolymer is fashioned into a water-insoluble bead, a water-insoluble membrane or a latex particle, or can be a swollen aqueous gel suitable for use as an electrophoresis gel.

This copolymer is preferably the reaction product of about 1 to 99 parts of a condensation-polymerizable monomer containing a moiety cluster selected from the group consisting of (1) at least three epoxy groups, (2) at least three ester groups, (3) at least one epoxy and at least two ester groups and (4) at least one ester and at least two epoxy groups; about 1 to 99 parts of a second condensation-polymerizable monomer containing a moiety cluster selected from the group consisting of (1) at least two ester groups, (2) at least two epoxy groups and (3) at least one ester and one epoxy group; and an amount of 1,1-dialkylhydrazine equivalent, on a molar basis, substantially equal to-the total molar content of epoxy groups.

4.4.6.1 Amminimide Containing Support Materials

Commercially available or readily obtainable chromatographic support materials for chromatographic and other applications, as well as other fabricated materials may be derivatized with tailored aminimide moieties, through chemical modification, producing novel materials capable of recognizing specific molecular structures.

The following general structures are contemplated.

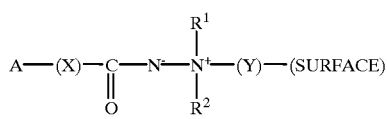

and

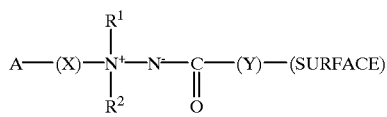

In the structures above, A is selected from the group consisting of amino acids, oligopeptides, polypeptides and proteins, nucleotides, oligonucleotides, polynucleotides, carbohydrates, molecular structures associated with therapeutic agents, metabolites, dyes, photographically active chemicals, and organic structures having desired steric, charge, hydrogen-bonding or hydrophobicity elements; X and Y are chemical bonds or groups consisting of atoms selected from the set of C, H, N, O, S; $R^1$ and $R^2$ are chosen from the group of alkyl, cycloalkyl, aryl, aralkyl, alkaryl and, preferably, structures mimicking the side-chains of naturally-occurring amino acids.

Surfaces and other structures functionalized with multiple aminimide subunits are also preferred; general structures are shown below.

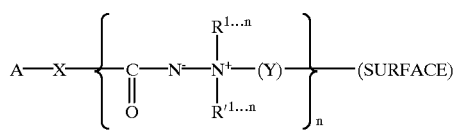

and

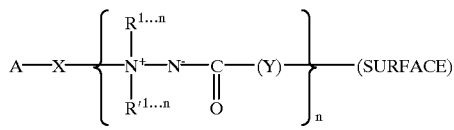

In the above structures $R^{1\cdots n}$ and $R'^{1\cdots n}$ are used to illustrate the manner in which the hydrazine substituents $R^1$ and $R^2$ can be varied in each polymerization step described above to produce a functional supported oligomer or polymer.

The following chemical modifications can be used to prepare aminimide-functionalized surfaces.

4.4.6.1.1 Functionalization of Ester and Epoxy Surfaces

A surface bearing ester groups can be treated with an epoxide; containing desired group B, and a disubstituted hydrazine to form an aminimide surface as follows:

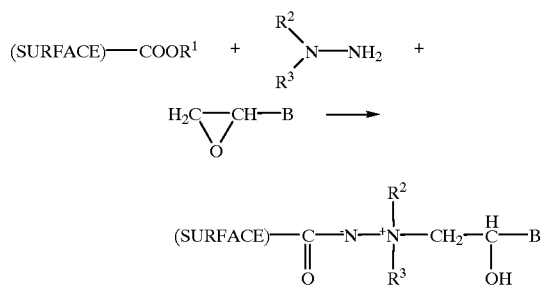

To carry out the above reaction, the surface is treated with a solution containing a 10% molar excess of the epoxide (based on the calculated number of reactive ester groups of the surface), and a stoichiometric amount of the hydrazine (with respect to the amount of the epoxide) in an appropriate solvent, such as an alcohol, with shaking. The mixture is then allowed to stand at room temperature for 1 week with occasional shaking. At the end of this period, the solvent is removed by decantation, and the surface is thoroughly washed with fresh solvent and air dried.

This approach allows the functionalization of readily available supports containing ester groups.

The above reaction sequence can also be employed with an epoxide-functionalized surface:

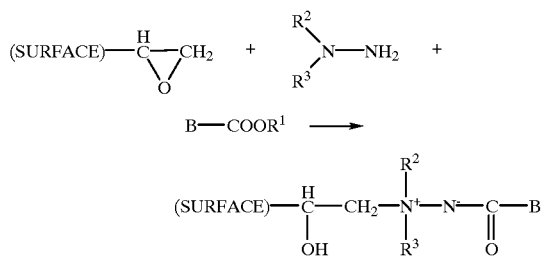

To carry out the above reaction, the surface is treated with a solution containing a 10% molar excess of the ester (based on the calculated number of reactive epoxide groups of the support), and a stoichiometric amount of the hydrazine (with respect to the amount of the ester used), in an appropriate solvent, such as an alcohol, with shaking. The mixture is then allowed to stand at room temperature for 1 week with occasional shaking. At the end of this period, the solvent is removed by decantation, and the surface is thoroughly washed with fresh solvent and air dried.

The foregoing reaction can be modified by utilizing an ester whose substituent B contains a double bond. After completion of the reaction shown above, the double bond of the ester can be epoxidized using one of a variety of reactions including the asymetric epoxidation of Sharples (e.g., utilizing a peracid under suitable reaction conditions well-known in the art), and the product used as the epoxide in a new repetition of the aminimide-forming reaction. The overall process can be repeated to form oligomers and polymers.

For example, using β,γ-butenoic acid methyl ester as the ester, n repetitions of the above reaction sequence produces a compound of the form:

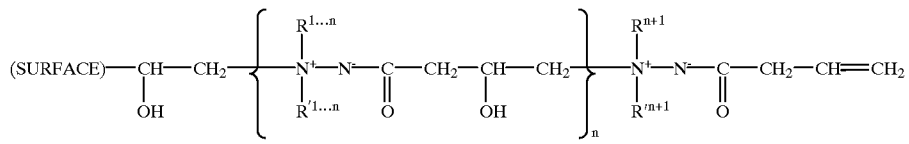

where the designations $R^{1\cdots n}$ and $R'^{1\cdots n}$ are used to illustrate the manner in which the hydrazine substituents $R^2$ and $R^3$ are varied in each polymerization step, if desired, to produce an oligomer or polymer.

The foregoing reactions can be carried out using bifunctional esters of the form ROOC—X—COOR', where X is a linker and R and R' are alkyl groups as defined above, and/or bifunctional epoxides of the form shown below,

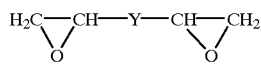

wherein Y is a linker as defined above, to form desirable polymers. If an ester-functionalized surface is reacted with bifunctional esters and epoxides, the resulting surface will have the following general structure.

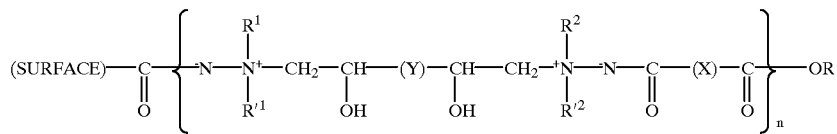

If an epoxide-functionalized surface is reacted as above the derivatized surface will have the following general structure.

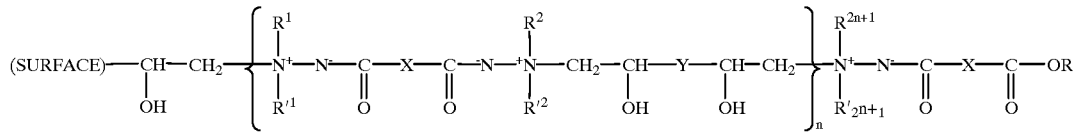

4.4.6.1.2 Functionalization of Amine Surfaces

An amine-functionalized surface can be converted to an ester-bearing surface by reaction with an acrylic ester as shown in sequence (a) below. This reaction is followed by reaction with hydrazine and an epoxide as shown in sequence (b).

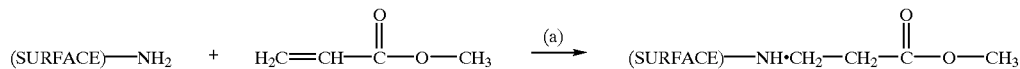

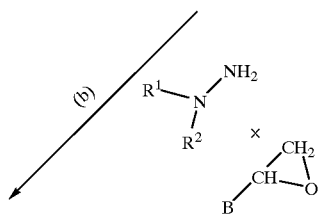

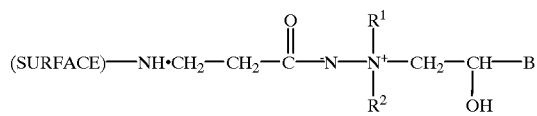

For reaction (a), a 10% molar excess of methyl acrylate (based on the number of reactive amino groups the surface as determined by a titration with acid) is dissolved in an appropriate solvent, such as an alcohol, and added to the surface. After addition is complete, the mixture is shaken at room temperature for 2 days. The solvent is then removed by decantation and the surface is washed thoroughly with fresh solvent in preparation for the next step.

For reaction (b) the stoichiometric amount of a 1:1 mixture of the hydrazine and the epoxide, is combined in an appropriate solvent, such as an alcohol, and quickly added to the solvent-wet surface from reaction (a). The mixture is shaken at room temperature for 3 days. The solvent is then removed by decantation, and the surface is washed thoroughly with fresh solvent and dried.

The above reaction sequence can also be employed with an epoxide-functionalized surface, in which case substituent B in the structure above represents the surface and the desired functional group bears the amine moiety. One way of obtaining such a surface is to react a silica surface with a silicic ester containing an epoxide group to produce a so-called "epoxy silica", as shown below.

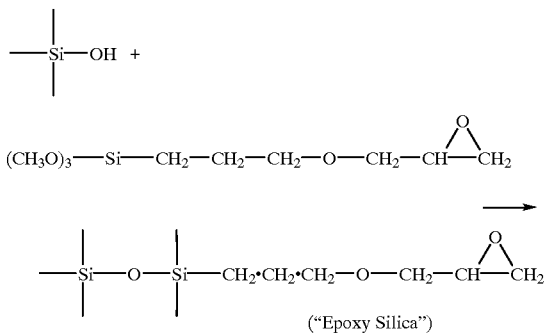

4.4.6.1.3 Functionalization of Carboxylic-Acid-Containing Surfaces

A surface functionalized with a carboxylic acid group can be reacted with an 1,1-dialkylhydrazine and a coupling agent, such as dicyclohexyl carbodiimide (DCC), to form a hydrazone-containing surface as shown in step (a) below. This surface can then be coupled with a desired group B bearing a substituent capable of alkylating the hydrazone to give an aminimide structure (after treatment with base), as shown in step (b):

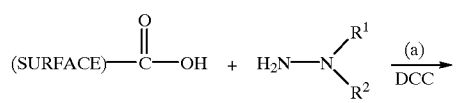

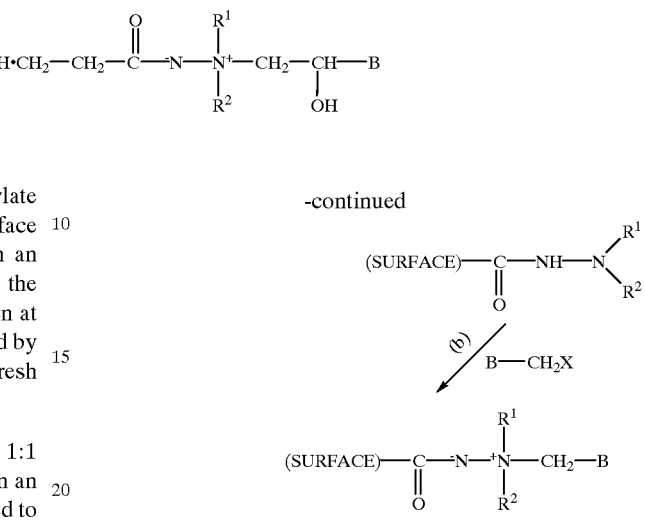

Substituent B is a surface functionalized with an alkylating agent capable of reacting with a hydrazone.

To perform the above chemical modification of a carboxyl-bearing surface, the surface is treated with a 10% molar excess equimolar amounts of the N,N-dimethylhydrazine and DCC in a suitable solvent, such as methylene chloride, and the mixture is shaken for 2 hours at room temperature. The slurry is then removed by decantation and the surface is washed thoroughly with fresh solvent to remove any residual precipitated dicyclohexyl urea. The surface is then treated with a stoichiometric amount of the alkylating agent in a suitable solvent, warmed to 70° C. and held at this temperature for 6 hours. The mixture is then cooled, the solvent is removed by decantation, and the surface is washed with fresh solvent and dried.

4.4.6.1.4 Functionalization of Surfaces Capable of Hydrazide Alkylation

A surface bearing a group capable of alkylating acyl hydrazones can be functionalized to contain aminimide groups as follows:

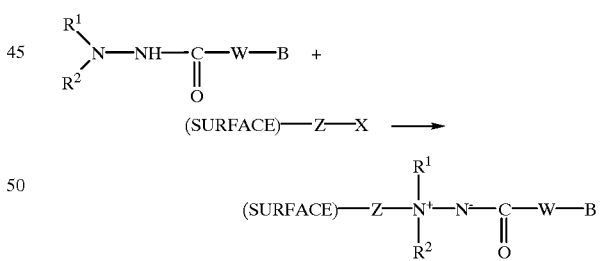

In the equation above, Z and W are linkers composed of atoms selected from the set of C, N, H, O, S, and X is a suitable leaving group, such as a halogen or tosylate.

A hydrazone bearing a desired group B is produced by reacting the appropriate 1,1'-dialkylhydrazine with any of a variety of derivatives containing B via reactions that are well-known in the art. These derivatives may be acid halides, azlactones (oxazolones), isocyanates, chloroformates, or chlorothioformates.

4.4.6.1.5 Functionalization of Surface Bearing —NH, —SH, or —OH Groups with Chloromethyl Aminimides Surfaces functionalized with —NH$_2$, —SH, or —OH groups can be functionalized by treating them with chloromethyl aminimides in the presence of strong base using the experimental conditions outlined above:

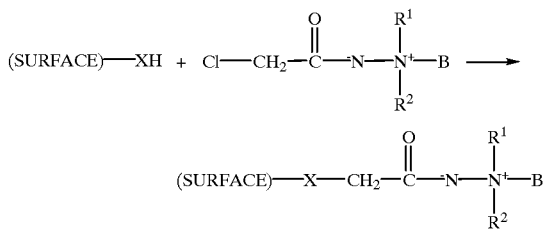

The required chloromethyl aminimides can be prepared by known literature procedures (See, e.g., 21 *J. Polymer*

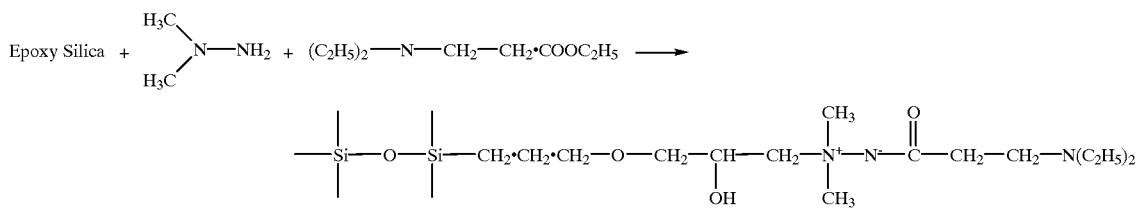

*Sci., Polymer Chem. Ed.* 1159 (1983)), or by using the techniques described above.

4.4.6.1.6 Functionalization of Oxazolone-Containing Surfaces

Oxazolone-containing surfaces can be functionalized by first reacting them with 1,1'-dialkylhydrazine as shown in step (a) below followed by alkylation of the resulting hydrazone with an alkylating agent B—$CH_2$—X as shown in step (b); reaction conditions similar to those described above are expected to be effective in carrying out these modifications.

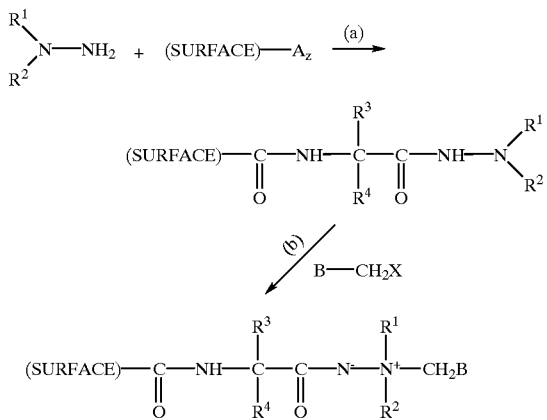

In the structures above, $R^3$ and $R^4$ are derived from the five membered azlactone ring denoted by Az.

Although the previous discussions are specifically directed to the functionalization of surfaces, these reactions can also be used to construct aminamide linkages to the other species of A and B which are described in this application.

4.4.7 Preparation of Aminimide-Based Coatings for Support Materials

It is possible to produce aminimide-functionalized composite support materials by coating various soluble amin- imide formulations on the surfaces of existing supports, and subsequently crosslinking the resulting coatings in place to form mechanically stable surfaces. The coating may be engineered for a particular application (e.g., to take the form of a thin non-porous film or to possess localized microporosity for enhanced surface area) by judicious selection of process conditions, monomer loading levels, the crosslinking mechanism and the amount of crosslinker.

For example, any of the foregoing reactions can be carried out with a vinyl aminimide in contact with a selected surface, which is polymerized according to well-known techniques (see, e.g., U.S. Pat. No. 4,737,560). The polymerization results in a surface coated with a polymer containing aminimide side-chains. Other coating procedures employing aminimide functional groups are described below in greater detail.

4.4.8 Synthesis of Aminimide-Containing Materials Via Polymerizations of Aminimide-Based Molecules In addition to utilizing aminimide chemistry to chemically modify commercially available or readily obtainable surfaces, new surfaces and other materials can be fabricated de novo from aminimide precursors bearing polymerizable groups by polymerizations and/or copolymerizations in the presence or absence of crosslinking agents. Depending upon the properties for the desired material, various combinations of monomers, crosslinkers, and ratios thereof may be employed. The resultant support materials may be latex particles, porous or non-porous beads, membranes, fibers, gels, electrophoresis gels, or hybrids thereof. Furthermore, the monomers and crosslinking agents may or may not all be aminimides.

Vinyl or condensation polymerizations may be advantageously employed to prepare the desired aminimide-containing materials. Vinyl polymerization can include use of one or more monomers of the form $CH_2$=CH—X that are copolymerizable with aminimides; suitable examples include styrene, vinyl acetate, and acrylic monomers. If desired, compatible non-aminimide crosslinkers, such as divinyl benzene, may be employed (either singly or in combination as the other such agents).

Condensation polymerization may be accomplished using multifunctional epoxides and multifunctional esters with the appropriate amounts of an 1,1'-dialkylhydrazine, using the reaction conditions described above. Either the ester component or the epoxide component should be at least trifunctional to obtain three-dimensionally crosslinked polymer structures; preferably, both components are trifunctional.

The nature and conditions of processing, the ratio of the various monomers and the ratio of crosslinker to total monomer content can be varied to produce a variety of product structures (e.g., beads, fibers, membranes, gels, or hybrids of the foregoing) and to tailor the mechanical and surface properties of the final product (e.g., particle size and shape, porosity, and surface area). Appropriate parameters for a particular application are readily selected by those skilled in the art.

4.4.9 Combinatorial Libraries of Peptidomimetics Derived From Aminimide Modules The synthetic transformations of aminimides outlined above may be readily carried out on solid supports in a manner analogous to performing solid phase peptide synthesis, as described by Merrifield and others (see for example, Barany, G., Merrifield, R. B., Solid Phase Peptide Synthesis, in The Peptides Vol. 2, Gross E., Meienhofer, J. eds., p. 1–284, Acad. Press, New York 1980; Stewart, J. M., Yang, J. D., Solid Phase Peptide Synthesis, 2nd ed., Pierce Chemical Co., Rockford, Ill. 1984; Atherton, E., Sheppard, R. C., Solid Phase Peptide Synthesis, D. Rickwood & B. D. Hames eds., IRL Press ed. Oxford U. Press, 1989). Since the assembly of the aminimide-derived structures is modular, i.e., the result of serial combination of molecular subunits, huge combinatorial libraries of aminimide-based oligomeric structures may be readily prepared using suitable solid-phase chemical synthesis techniques, such as those of described by Lam (K. S. Lam, et al. *Nature* 354, 82 (1991)) and Zuckermann (R. N. Zuckermann, et al. *Proc. Natl. Acad. Ser. USA*, 89, 4505 (1992); J. M. Kerr, et al., *J. Am Chem. Soc.* 115, 2529 (1993)). Screening of these libraries of compounds for interesting biological activities, e.g., binding with a receptor or interacting with enzymes, may be carried out using a variety of approaches well known in the art. With "solid phase" libraries (i.e., libraries in which the ligand-candidates remain attached to the solid support particles used for their synthesis) the bead-staining technique of Lam may be used. The technique involves tagging the ligand-candidate acceptor (e.g., an enzyme or cellular receptor of interest) with an enzyme (e.g., alkaline phosphatase) whose activity can give rise to color production thus staining library support particles which contain active ligand-candidates and leaving support particles containing inactive ligand-candidates colorless. Stained support particles are physically removed from the library (e.g., using tiny forceps that are coupled to a micromanipulator with the aid of a microscope) and used to structurally identify the biologically active ligand in the library after removel of the ligand acceptor from the complex by e.g., washing with 8M guanidine hydrochloride. With "solution-phase" libraries, the affinity selection techniques described by Zuckermann above may be employed.

An especially preferred type of combinatorial library is the encoded combinatorial library, which involves the synthesis of a unique chemical code (e.g., an oligonucleotide or peptide), that is readily decipherable (e.g., by sequencing using traditional analytical methods), in parallel with the synthesis of the ligand-candidates of the library. The structure of the code is fully descriptive of the structure of the ligand and used to structurally characterize biologically active ligands whose structures are difficult or impossible to elucidate using traditional analytical methods. Coding schemes for construction of combinatorial libraries have been described recently (for example, see S. Brenner and R. A. Lerner, *Proc. Natl. Acad. Sci. USA* 89, 5381 (1992); J. M. Kerr, et al. *J. Am. Chem. Soc.* 115, 2529 (1993)). These and other related schemes are contemplated for use in constructing encoded combinatorial libraries of oligomers and other complex structures derived from aminimide units.

The power of combinatorial chemistry in generating screenable libraries of chemical compounds e.g., in connection with drug discovery, has been described in several publications, including those mentioned above. For example, using the "split solid phase synthesis" approach outlined by Lam et al., the random incorporation of 20 different aminimide units into pentameric structures, wherein each of the five subunits in the pentamer is derived from one of the aminimide units, produces a library of $20^5 = 3,200,000$ peptidomimetic ligand-candidates, each ligand-candidate is attached to one or more solid-phase synthesis support particles and each such particle contains a single ligand-candidate type. This library can be constructed and screened for biological activity in just a few days. Such is the power of combinatorial chemistry using oxazolone modules to construct new molecular candidates.

The following is one of the many methods that are being contemplated for use in constructing random combinatorial libraries of aminimides-based compounds; the random incorporation of three aminimides derived from α-chloroacetyl chloride and the hydrazines shown below to produce 27 trimeric structures linked to the support via a succinoyl linker is given below.

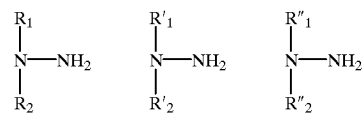

(1) A suitable solid phase synthesis support, e.g., the chloromethyl resin of Merrifield is treated with 4-hydroxyl butyric acid in the presence of $CsCO_3$ followed by tosylation with p-toluenesulfonyl chloride, under conditions known in the art;

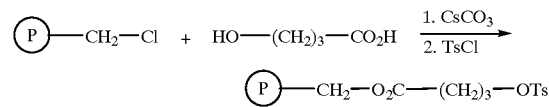

(2) The resulting resin is split into three equal portions. Each portion is coupled with one of the hydrazines shown above to give the hydrazinium resin which is converted to the aminimide by reaction with chloroacetyl chloride using the experimental conditions described above.

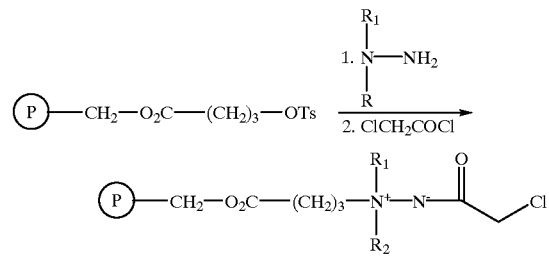

(3) The aminimide resin portions are mixed thoroughly and split again into three equal portions. Each resin portion is coupled with a different hydrazine followed by a coupling with a-chloracetyl chloride producing a resin with two linked aminimide subunits. The resin portions are then mixed thoroughly and split into three equal portions.

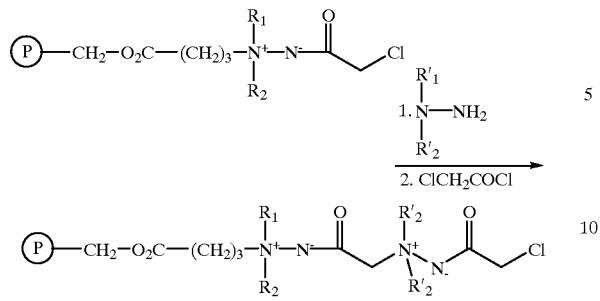
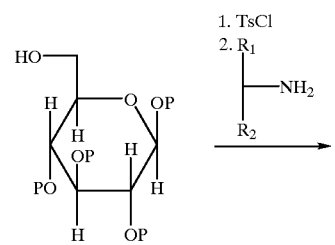

(4) Each resin portion is coupled with a different hydrazine followed by reaction with an acid chloride to produce a resin with three linked aminimide subunits;

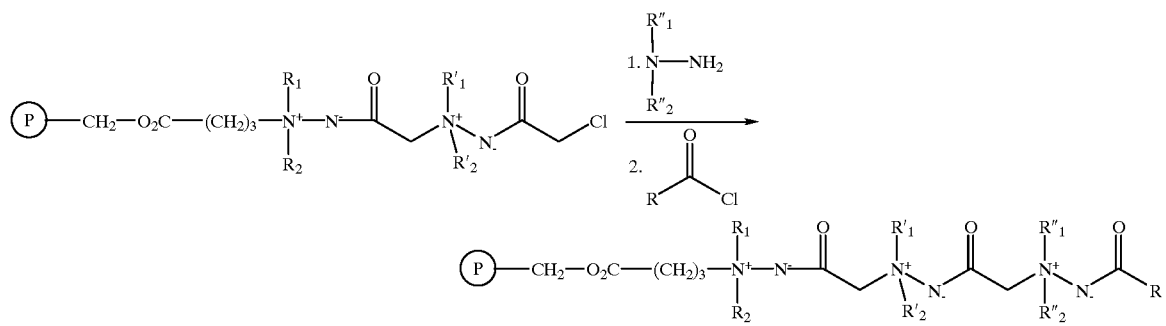

The resin portions are mixed producing a library containing 27 types of beads each bead type containing a single trimeric aminimide species for screening using the bead-stain method described above. Alternatively, the aminimides may be detached from the support via acidolysis producing a "solution-phase" library of aminimides containing a butyrylated terminal nitrogen. (Shown in the structure below in which $R=C_3H_7$)

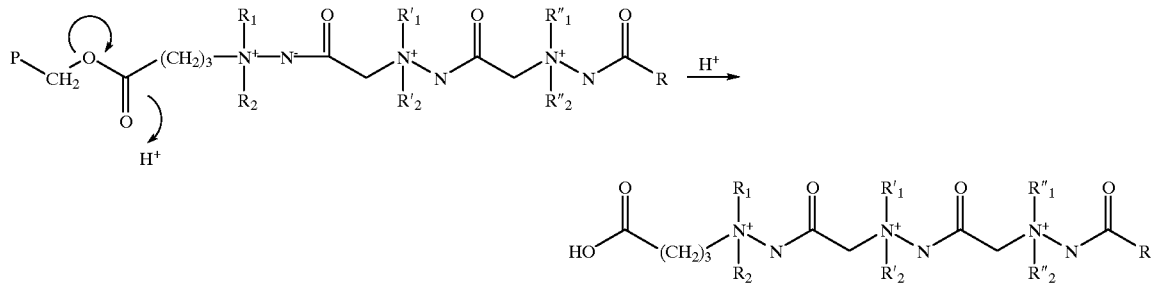

4.4.10 Design and Synthesis of Aminimide-Based Glycopeptide Mimetics

A great variety of saccharide and polysaccharide structural motifs incorporating aminimide structures are contemplated including, but not limited to, the following.

(1) Replacement of certain glycosidic linkages by aminimide backbones using reactions well known in the art of sugar chemistry and reactions described above.

ics. (*Comprehensive Organic Chemistry*, Sir Derek Barton, Chairman of Editorial Board, Vol. 5, E. Haslam, Editor, pp. 23–176).

A great variety of nucleotide and oligonucleotide structural motifs incorporating aminimide-based structures are contemplated including, but not limited to, the following.

(1) For the synthesis of oligonucleotides containing peptidic aminimide-based linkers in place of the phosphate diester groupings found in native oligonucleotides, the following approach is one of many that is expected to be useful.

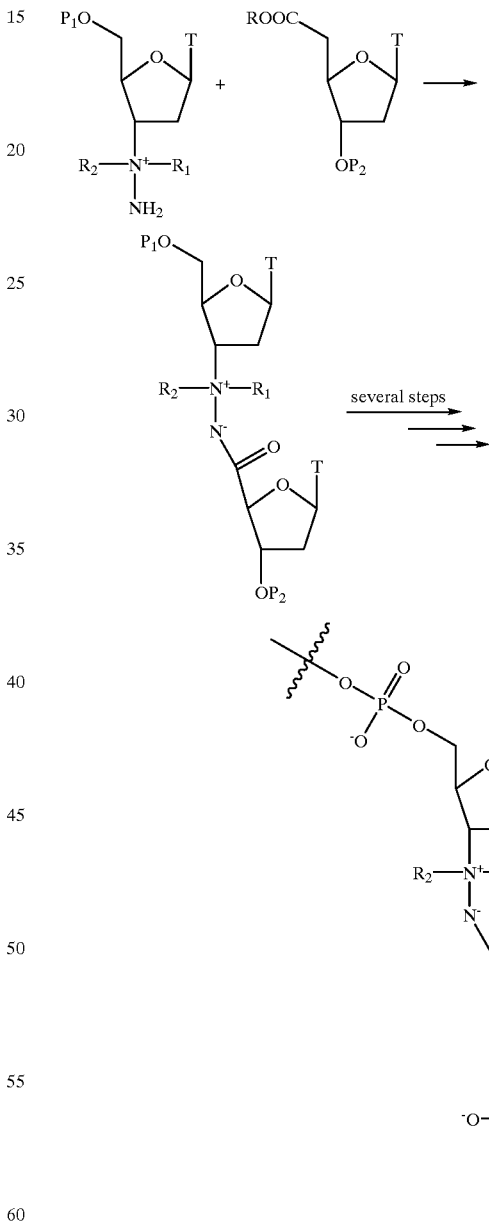

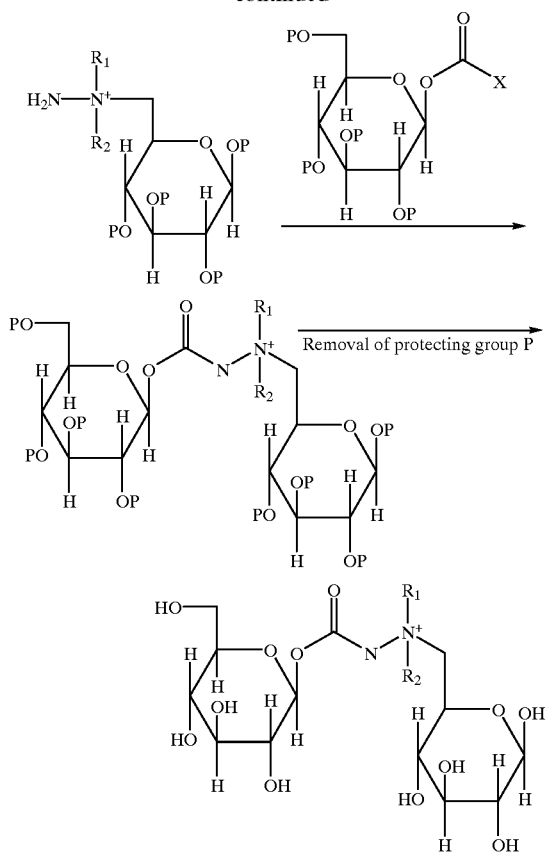

(2) Use of aminimide structures as linkers holding in place a sugar derivative and a tailored mimetic, or another sugar.

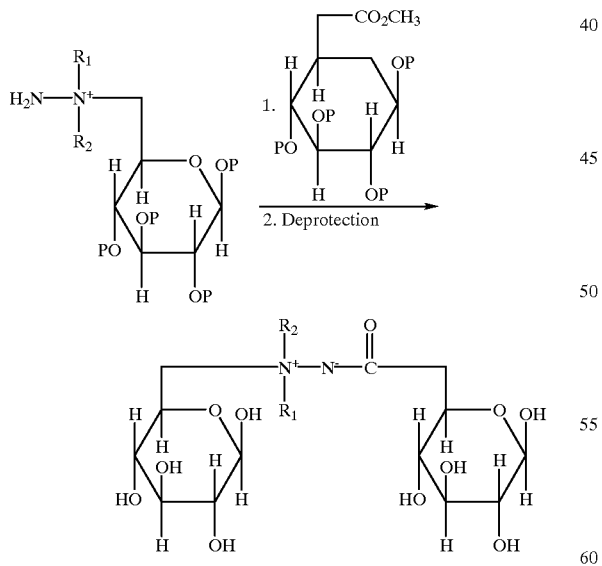

4.4.11 Design and Synthesis of Aminimide-Containing Oligonucleotide Mimetics

The art of nucleotide and oligonucleotide synthesis has provided a great variety of suitably blocked and activated furanoses and other intermediates which are expected to be very useful in the construction of aminimide-based mimet- (2) For the synthesis of structures in which an aminimide grouping is used to link complex oligonucleotide-derived units, an approach such as the following is expected to be very useful.

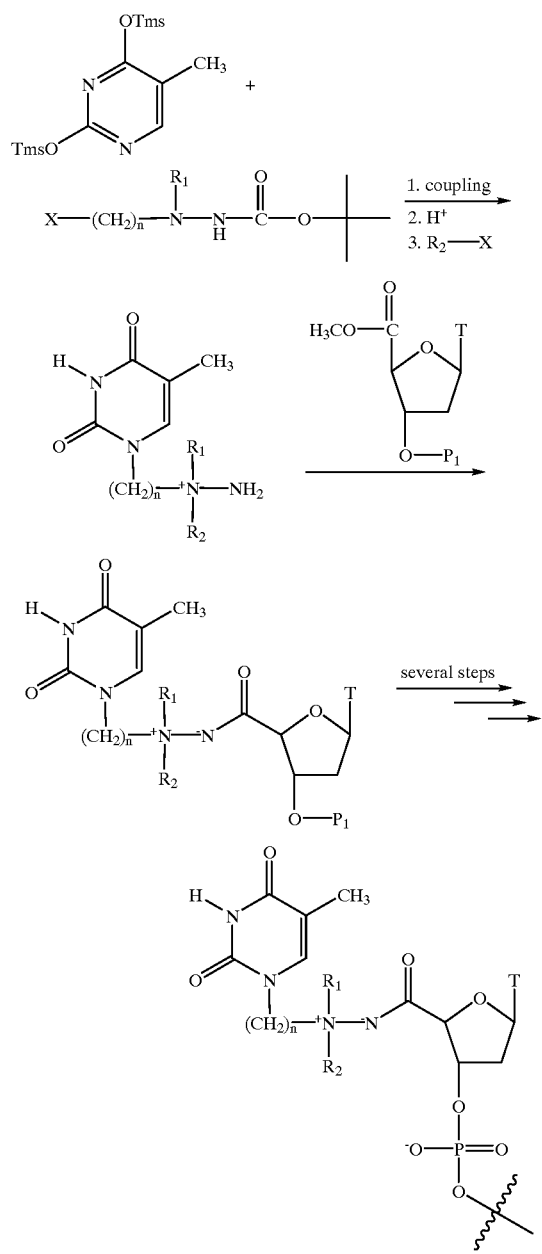

5. EXAMPLE
Synthesis of an Amphiphilic Ligand Mimetic Useful in Isolation and Purification of Receptors Binding Vincamine To a solution of 1.84 g (0.01 mol) of 1,2-epoxy dodecane (I) in a suitable solvent, such as n-propanol, is added with stirring 0.61 g (0.01 mol) of 1,1-dimethylhydrazine. The solution is stirred for 1 hour at room temperature, cooled to 10° C. in an ice bath, and a solution of 3.54 g (0.01 mol) of vincamine (II) dissolved in the minimum amount of the same solvent is added. The reaction mixture is stirred at 0° C. for 2 hours, allowed to come to room temperature, and stirred at room temperature for 3 days. At the end of this time the solvent is removed under high vacuum (0.2 torr) and the crude product is isolated. The conjugate (II) is useful as a stabilization agent for the isolation and purification of receptor proteins which are therapeutically acted upon by vincamine and by structurally related molecules.

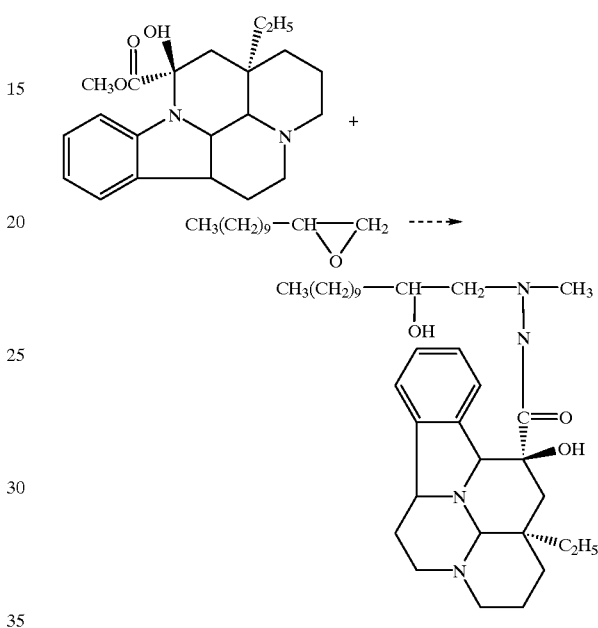

6. EXAMPLE
Synthesis of Amphiphilic Ligand Mimetic Useful in the Isolation and Purification of Serotonin Binding Receptor 8.61 g (0.1 mol) of methyl acrylate is added over a 15 minute period to a stirred solution of 17.62 g (0.1 mol) of serotonin in 100 ml of a suitable solvent. The reaction mixture is allowed to come to room temperature and stirred at room temperature for 2 days. The solvent is then removed by freeze drying to yield the ester (IV). 6.01 g (0.1 mol) of 1,1-dimethylhydrazine is added with stirring to a solution of 18.4 g (0.1 mol) of 1,2-epoxydodecane in a suitable solvent, such as propanol. The mixture is stirred at room temperature for 1 hour and a solution of (IV) dissolved in the same solvent is added. The mixture is then stirred at room temperature for 3 days. At the end of this time the solvent is removed in vacuo to yield the serotonin conjugate (V), which is useful as a ligand for the discovery, stabilization and isolation of serotonin-binding membrane receptor proteins.

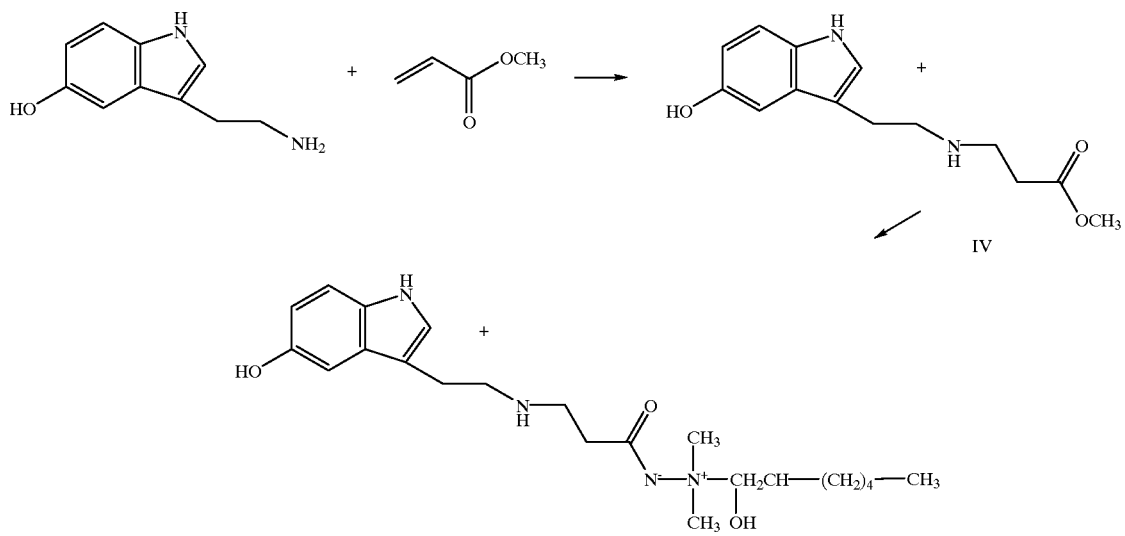

7. EXAMPLE
Synthesis of Rhodamine-B-Containing Ligand Mimetic Useful in the Isolation and Purification of Codeine-Binding Proteins 49.74 g (0.1 mol) of the acid chloride of Rhodamine B (VI), prepared from rhodamine B by the standard techniques for preparing acid chlorides from carboxylic acids, are dissolved in 500 ml of a suitable solvent and are added, with stirring, over a 1-hour period to a solution of 6.01 g (0.1 mol) of 1,1-dimethylhydrazine in 100 ml of the same solvent. The temperature is kept at 10° C. After the addition is complete, the mixture is stirred at room temperature for 12 hours, and the solvent is stripped away in vacuo to yield the Rhodamine B dimethylhydrazine (VII).

5.21 g (0.01 mol) of (VII) is dissolved in 100 ml of a suitable solvent, such as benzene, and 4.69 g (0.01 mol) of tosyl codeine (VIII), prepared from codeine by the standard techniques for the tosylation of an alcohol, in 50 ml of the same solvent is added over a 15-minute period with stirring. The mixture is heated to reflux and held at reflux for 1 hour. The mixture is then cooled, the solvent is removed in vacuo, the residue is redissolved in an appropriate alcohol and adjusted to pH 8 with 10% methanolic KOH. The precipitated salts are removed by filtration and the solvent is stripped in vacuo to yield the conjugate (IX), useful as a probe for the location, stabilization and isolation of receptor proteins that bind codeine and structurally similar analogues.

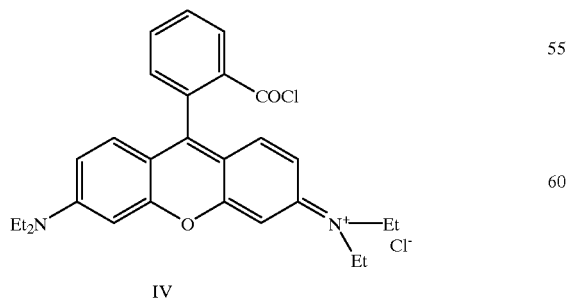

IV

-continued

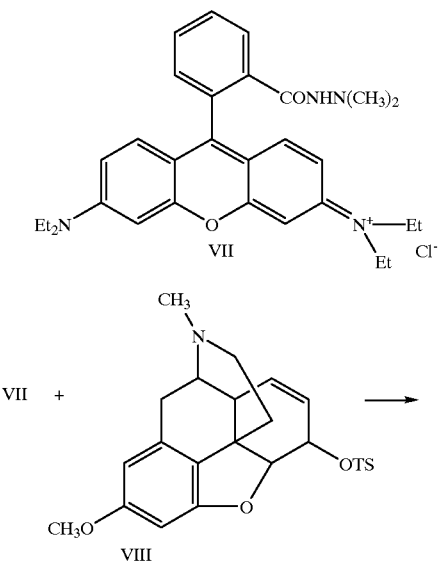

-continued

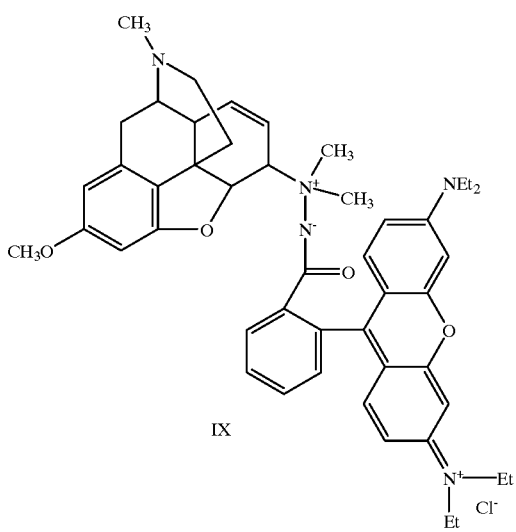

IX

8. EXAMPLE

Synthesis of Disperse-Blue-3-Containing Ligand Mimetic Useful in the Isolation and Purification of Codeine-Binding Proteins To a solution of 0.285 g (0.001 mol) of norcodeine (X) dissolved in 50 ml of a suitable solvent (such as benzene) is added a solution of 0.139 g (0.001 mol) of 4,4'-dimethylvinylazlactone (XI) in 10 ml of the same solvent and the resulting solution is heated to 70° C. and held at this temperature for 10 hrs. At the end of this time the temperature is brought to 10° C. with cooling and 0.06 g (0.001 mol) of 1,1-dimethylhydrazine dissolved in 10 ml of the same solvent is added dropwise. The solution is then re-heated to 70° C. and held at this temperature for 2 hours. 0.466 g (0.001 mol) of the Disperse blue 3 tosylate (XII), prepared by the standard tosylation techniques from a pure sample of the dye (obtained from the commercial material by standard normal-phase silica chromatography), is added and the mixture is heated at 70° C. for 2 more hours. The solvent is then removed in vacuo, the residue is redissolved in an appropriate alcohol solvent and titrated to pH 8 (measured with moist pH paper) with 10% (w/v) methanolic KOH. The precipitated salts are then removed by filtration, and the filtrate is stripped in vacuo to give conjugate (XIII), useful as a probe for the location and isolation of receptor proteins that bind codeine and similar molecules.

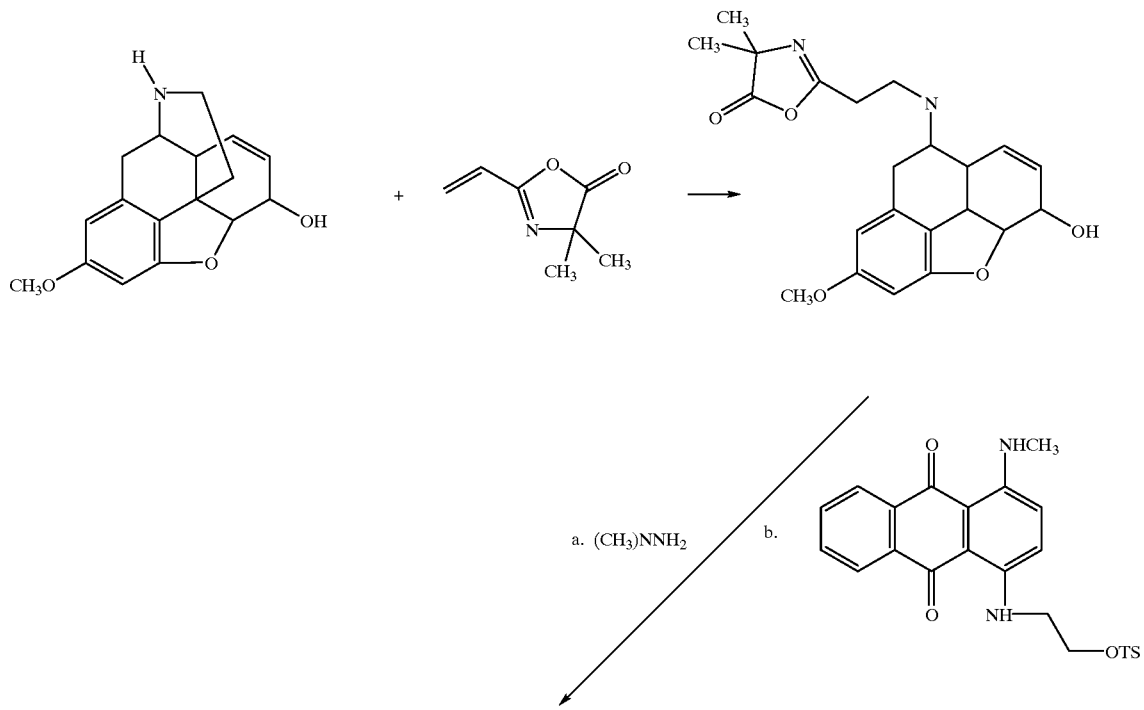

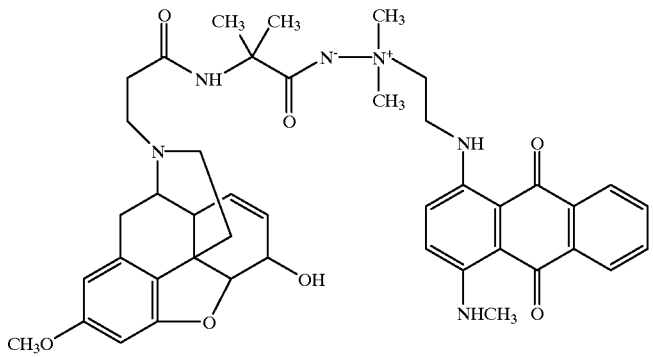

9. EXAMPLE
Synthesis of an Amphiphilic Ligand Mimetic for the Isolation and Purification of Codeine-Binding Proteins 29.95 g (0.1 mol) of octadecylisocyanate is added slowly to 6.01 g (0.1 mol) of 1,1-dimethylhydrazine in 100 ml of benzene. The mixture is stirred for 18 hours at room temperature and 54.2 g (0.1 mol) of tosyl codeine (VIII), prepared by the standard techniques, is added portionwise over a ½-hour period. The mixture is heated to reflux and stirred at reflux for 2 hours. At the end of this time the solvent is removed in vacuo, the residue is dissolved in an appropriate solvent (such as ethanol), and the pH is titrated to 8 (measured with moist pH paper) with 10% (w/v) methanolic KOH. The precipitated salts are then removed by filtration and the solvent is removed in vacua to give the crude conjugate (XIV), useful for stabilizing and isolating receptor proteins that bind to codeine and to similar molecules.

XIV

10. EXAMPLE
Synthesis of a Mimetic of the Protein-Kinase Binding Peptide a. The dodecamer peptide (BEAD)-Asp-His-Ile-Ala-Asn-Arg-Arg-Gly-Thr-Arg-Gly-Ser-$NH_2$ is obtained attached to the solid support as shown using standard FMOC peptide synthesis techniques, after deprotection of the terminal FMOC group. This peptide is shaken with a solution of an equivalent molar amount of $ClCH_2COCl$ in a suitable solvent at 50° C. for 6 hours. The solvent is removed by decantation, leaving a terminal —NH—CO—$CH_2$Cl group attached to the peptide.

b. A solution of equimolar amounts of 1,1-dimethylhydrazine and dicyclohexylcarbodiimide in a suitable solvent is treated with an equivalent molar amount of the heptamer peptide $H_2$N-Thr-Thr-Tyr-Ala-Asp-Phe-Ile-COOH, prepared and obtained in the free state using the standard FMOC solid phase peptide synthesis chemistry (e.g., using instruments and methods marketed by the Milligen Division of Millipore Corp.). The mixture is stirred for 4 hours at room temperature. The precipitated N,N'-dicyclohexyl urea is removed by centrifuging and decantation, and the solution is added to the functionalized beads prepared in a. above. The mixture is then heated to 50° C. and shaken overnight at this temperature. The mixture is cooled, the solvent removed by decantation, and the peptide released from the bead to yield the aminimide mimetic $H_2$N-Thr-Thr-Tyr-Ala-Asp-Phe-Ile-CO—N—N($CH_3$)$_2$—$CH_2$-Ser-Gly-Arg-Thr-Gly-Arg-Asn-Ala-Ile-His-Asp-COOH. This mimetic has the aminimide in place of alanine in the naturally occurring protein-kinase binding peptide, UK (5–24), and is useful as a synthetic binding peptide with enhanced proteolytic stability.

11.1. Synthesis of a Mimetic of a Human Elastase Inhibitor

This example teaches the synthesis of a competitive inhibitor for human elastase based on the structure of known N-trifluoroacetyl dipeptide analide inhibitors (see 162 *J. Mol. Biol.* 645 (1982) and references cited therein).

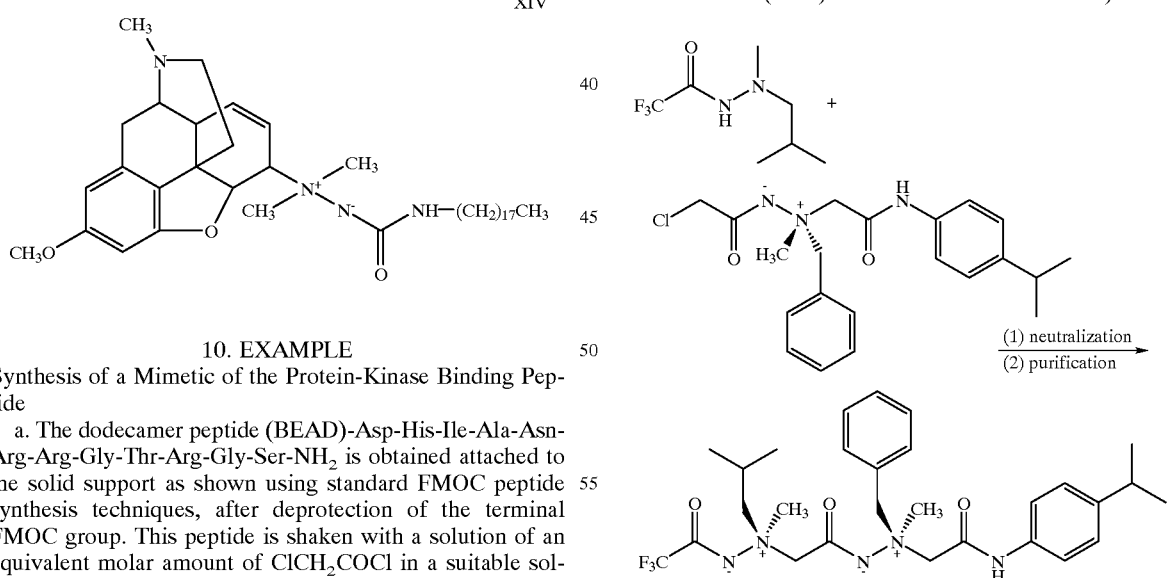

To 3.7 g (0.01 mol) of the aminimide N-(p-isopropylanalido)-methyl)-S-N-methyl-N-benzylchloromethylacetamide in 50 ml ethanol was added 1.86 g (0.01 mol) of 1-methyl-1-isobutyl-2-N-trifluoroacetyl hydrazone (prepared from the reaction of trifluoroacetic anhydride with 1-methyl-1-isobutylhydrazine [from methylisobutylamine and chloramine] using standard acylation methods) in 50 ml ethanol. The mixture was heated to reflux and stirred at reflux for 4 hours. The mixture was then cooled to room temperature and titrated with 10% (w/v) KOH in methanol to the phenolphthalein endpoint. The mixture was then filtered and the solvent removed in vacuo on a rotary evaporator. The residue was taken up in benzene and filtered. Removal of the benzene on the rotary evaporator yielded 5.1 g (95%) of crude mixed diastereomeric aminimides. The desired (S)-(S) isomer was obtained by normal-phase chromatographic purification over silica. This product is useful as a competitive inhibitor for human elastase, characterized by HPLC on Crownpack™ CR(+) chiral stationary phase (Daicell Chemical Industries Ltd.) using pH 2 aqueous mobile phase. NMR (DMSO-$d_6$): Chemical shifts, peak integrations and $D_2O$ exchange experiments diagnostic for structure.

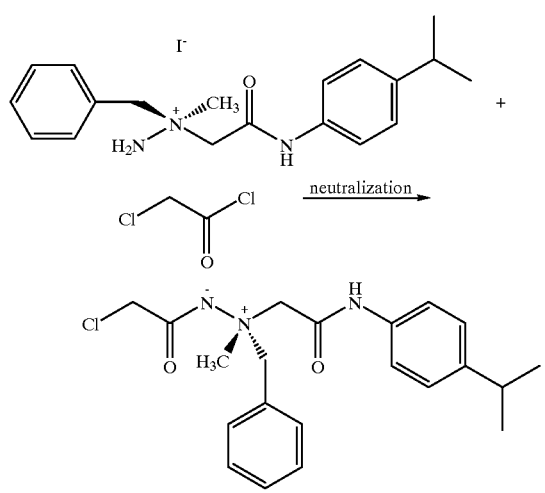

A mixture of 4.2 g (0.01 mol) of the hydrazinium iodide enantiomer prepared as outlined below, 1.0 g (0.0106 mol) chloroacetic acid and 1.24 g (0.011 mol) chloracetyl chloride, contained in a micro reaction flask equipped with a drying tube, was heated in an oil bath at 105° C. for 1 hour. The (homogeneous) reaction mixture was then cooled to room temperature and extracted with 4×20 ml of ethyl ether to remove chloracetyl chloride and chloracetic acid, with vigorous stirring each time. The residual semisolid was dissolved in the minimum amount of methanol and titrated with 10% KOH in methanol to the phenolphthalein end point. The precipitated salts were filtered and the filtrate evaporated to dryness on a rotary evaporator at 40° C. The residue was taken up in benzene and filtered. The solvent was removed on a rotary evaporator to yield 3.37 g (90%) of the (S)-aminimide enantiomer, characterized by $CDCL_3$ NMR spectrum and $D_2O$ exchange experiments and directly used in the next step in the sequence (see above).

11.3. Synthesis of the Chiral Aminimide Starting Material

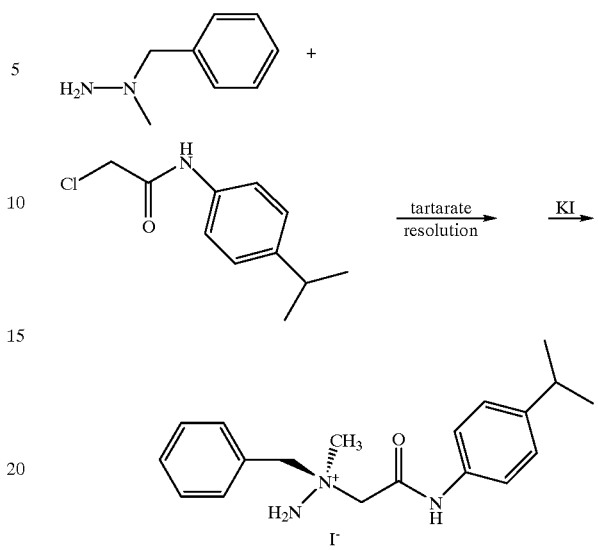

13.6 g (0.1 mol) of 1-methyl-1-benzyl-hydrazine (prepared from methyl benzyl amine and chloramine using standard methods [*J. Chem. Ed.* 485 (1959)]) in 125 ml of toluene was cooled to 5° C. in an ice bath. To this was gradually added, with vigorous stirring over a one-hour period, a solution of 21.17 g (0.1 mol) of p-isopropylphenyl chloromethyl analide (prepared from chloracetyl chloride and p-isopropylphenyl amine) dissolved in 100 ml of toluene. Throughout the addition, the temperature was maintained at 5° C. The reaction mixture was then allowed to warm to room temperature, and was stirred overnight. The precipitated solid hydrazinium salt was filtered, washed with cold toluene and dried in a vacuum oven at 60° C./30" to yield 34.3 g (98%) of racemic product. This racemate was slurried at room temperature overnight in 100 ml ethanol and a slight molar excess of moist silver oxide was added and the mixture was stirred at room temperature overnight. The mixture was then filtered into an ethanolic solution containing an equivalent of D-tartaric acid in the minimum amount of solvent. The alcoholic filtrate was concentrated to approximately 20% of its volume and diethylether was added until turbidity was observed. The turbid solution was then cooled at 0° C. overnight and the crystals were collected by filtration. The solid substance was purified by recrystallization from ethanol/ether to yield the desired pure diastereomeric salt, which was subsequently converted to the iodide form by precipitation from a water-ethanol solution of the tartrate (made alkaline by the addition of sodium carbonate) on treatment with an equivalent of solid potassium iodide, characterized by HPLC on Crownpack™ CR(+) chiral stationary phase (Daicell Chemical Industries Ltd.) using pH 2 aqueous mobile phase. NMR (DMSO-$d_6$): chemical shifts, peak integrations & $D_2O$ exchange experiments diagnostic for structure.

14. EXAMPLE

Synthesis of a Peptide Mimetic Inhibiting Human Elastase

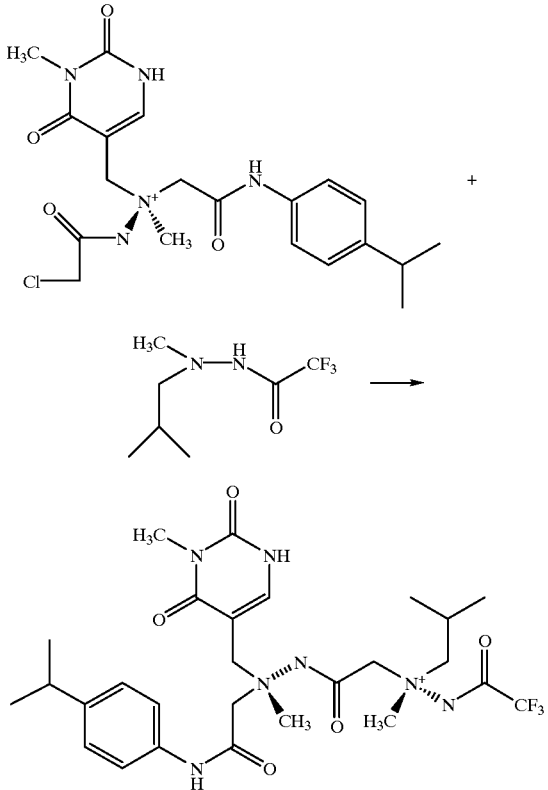

To 4.36 g (0.01 mol) of the chloromethylaminimide above in 50 ml ethanol was added a solution of 1.86 g (0.01 mol) of 1-methyl-1-isobutyl-2-N-trifluoroacetyl hydrazone (prepared from the reaction of trifluoroacetic anhydride with 1-methyl-1-isobutylhydrazine [from methyl isobutyl amine and chloramine] using standard acylation conditions) in 50 ml of ethanol. The mixture was heated to reflux, stirred at reflux for 4 hours, then cooled to room temperature and titrated with 10% (w/v) KOH in methanol to the phenolphthalein endpoint. The mixture was filtered and the solvent was removed in vacuo on a rotary evaporator. The residue was taken up in benzene and again filtered. Removal of the benzene on the rotary evaporator yielded 5.7 g (95%) of the mixed (R)-(S) and (S)-(S) aminimide diastereomers. The desired (S)-(S) isomer was obtained pure by normal-phase chromatographic purification over silica. This product is useful as a competitive inhibitor for human elastase, characterized by HPLC on Crownpack™ CR(+) chiral stationary phase (Daicell Chemical Industries Ltd.) using pH 2 aqueous mobile phase. NMR (DMSO-$d_6$): chemical shifts, peak integrations & $D_2O$ exchange experiments diagnostic for structure.

Synthesis of the Chiral Chloroaminimide

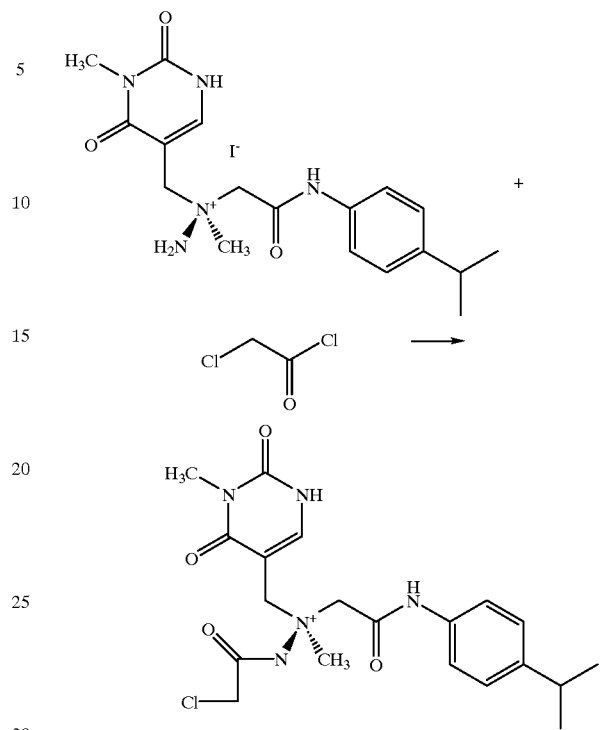

A mixture of 4.87 g (0.01 mol) of the hydrazinium iodide enantiomer prepared as described in 5.2.3, 1.0 g (0.0106 mol) chloroacetic acid and 1.24 g (0.011 mol) chloroacetyl chloride, contained in a micro reaction flask equipped with a drying tube, was heated at 105° C. for 1 hour with an oil bath. The (homogeneous) reaction mixture was then cooled to room temperature and extracted with 4×20 ml of ethyl ether to remove chloracetyl chloride and chloracetic acid. The residual semisolid mass was dissolved in the minimum amount of methanol and titrated with 10% KOH in methanol to the phenolphthalein end point. The precipitated salts were filtered and the filtrate was evaporated to dryness on a rotary evaporator at 40° C. The residue was then taken up in benzene and filtered. The solvent was removed on a rotary evaporator to give 3.88 g (89%) of the (S)-aminimide enantiomer, characterized by $CDCL_3$ NMR spectrum and $D_2O$ exchange experiments and used directly in the next step in the synthesis (see above).

Synthesis of the Chiral Aminimide

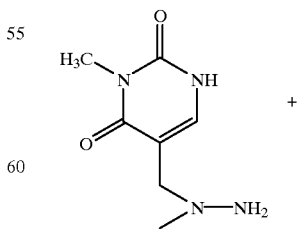

-continued

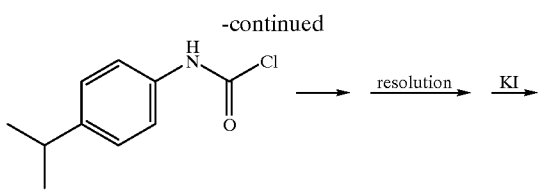

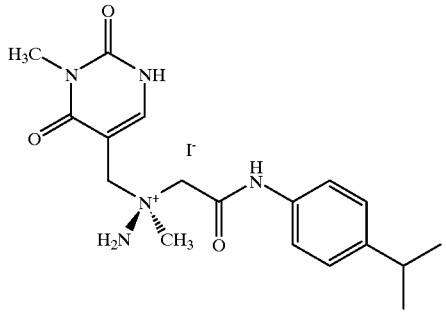

18.4 g (0.1 mol) of 1-(5'[3'-methyl uracil]methyl)-1-methylhydrazine (prepared by the alkylation of 2-methylphenylhydrazone with 5-chloromethyl-3-methyl uracil in ethanol, as described in 24 *J. Org. Chem.* 660 (1959) and references cited therein, followed by removal of the benzoyl group by acid hydrolysis) in 100 ml toluene was cooled to 5° C. in an ice bath and a solution of 21.1 g (0.1 mol) p-isopropylphenyl-chloromethylanalide (prepared from chloracetyl chloride and p-isopropylanaline), in 100 ml of toluene, was added thereto with vigorous stirring over a 1-hour period, maintaining a temperature of 5° C. The reaction mixture was then allowed to warm to room temperature and was stirred overnight. The solution was cooled to 0° C. and the precipitated hydrazinium chloride salt was filtered, washed with cold toluene and dried in a vacuum oven at 40° C./30" to yield 4.77 g (98%) of crude racemic product. This racemate was slurried in 100 ml ethanol, and a slight molar excess of moist silver oxide was added, and the mixture was stirred at room temperature overnight. This racemate was resolved via its tartrate salts and isolated as the iodide using the method of Singh, above, characterized by HPLC on Crownpack™ CR(+) chiral stationary phase (Daicell Chemical Industries Ltd.) using pH 2 aqueous mobile phase. NMR (DMSO-$d_6$): chemical shifts, peak integrations & $D_2O$ exchange experiments diagnostic for structure.

Synthesis of 3-methyl-5-chloromethyluracil

A. 74.08 g (1 mol) of N-methyl urea and 216.2 g (1 mol) diethylethoxymethylenemalonate were heated together at 122° C. for 24 hours, followed by 170° C. for 12 hours, to give the 3-methyluracil-5-carboxylic acid ethyl ester in 35% yield (following recrystallization from ethyl acetate).

B. 30 g 3-methyluracil-5-carboxylic acid ethyl ester was saponified with 10% NaOH to yield the free acid in 92% yield (after standard work-up and recrystallization from ethyl acetate).

C. 20 g of 3-methyluracil-5-carboxylic acid was decarboxylated at 260° C. to give a quantitative yield of 3-methyluracil.

D. 3-methyluracil-5-carboxylic acid was treated with HCl and $CH_2$ using standard chloromethylation conditions to give 3-methyl-5-chloromethyl uracil in 52% yield (following standard work-up and recrystallization from ethyl acetate). NMR (DMSO-$d_6$): chemical shifts, peak integrations & $D_2O$ exchange experiments diagnostic for structure.

13. EXAMPLE

Synthesis of a Peptide Mimetic Inhibiting the HIV Protease

This example teaches the synthesis of a competitive inhibitor for the HIV protease with enhanced stability, based on the insertion of a chiral aminimide residue into the scissile bond position of the substrate Ac-L-Ser(Bzl)-L-Leu-L-Phe-L-Pro-L-Ile-L-Val-OMe (see, e.g., 33 *J. Med. Chem.* 1285 (1990) and references cited therein).

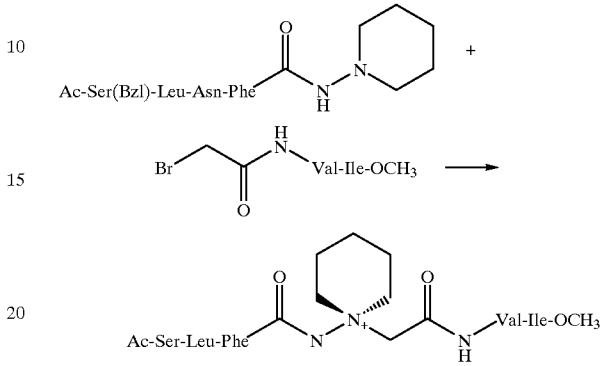

0.735 gms (1 mmol) of Ac-Ser(Bzl)-Leu-Asn-Phe-CO-NH-$NC_5H_{10}$ is dissolved in the minimum amount of DMF, and 0.344 g of $BrCH_2CONH$-Val-Ile-OMe, prepared by treatment of $H_2N$-Val-Ile-OMe with $(BrCH_2CO)_2O$ according to the method of Kent (256 *Science* 221 (1992), is added thereto. The mixture is heated to 60° C. and stirred at this temperature overnight. At this point the DMF is removed under high vacuum, and the desired (S) isomer is obtained from the enantiomeric mixture after neutralization by standard normal-phase silica chromatography to yield the protected peptide. The side chain blocking groups are subsequently removed using standard peptide deprotection techniques to yield the product Ac-Ser-Leu-Asn-Phe-CON⁻N+($C_5H_{10}$O)—$CH_2$—CO—NH-Val-Ile-OMe, useful as a enhanced stability competitive inhibitor for the HIV protease.

Synthesis of the Tetrapeptide Hydrazone

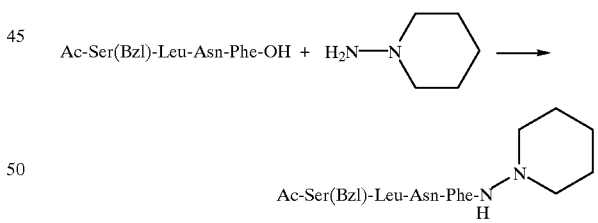

0.653 g (1 mmol) of AcSer(Bzl)-Leu-Asn-Phe-OH, prepared via standard peptide synthesis techniques (see 33 *J. Med. Chem.* 1285 (1990) and references cited therein), is coupled with 0.10 g (1 mmol) of 1-aminopiperidine using standard peptide-coupling methods and chemistries (see 33 *J. Org. Chem.* 851 (1968)) to give a 97% yield of the hydrazide, isolated by removal of the reaction solvent in vacuo.

14. EXAMPLE

Preparation of Chiral Monomer Useful in Polymerization Yielding Crosslinked Polymer-Chains

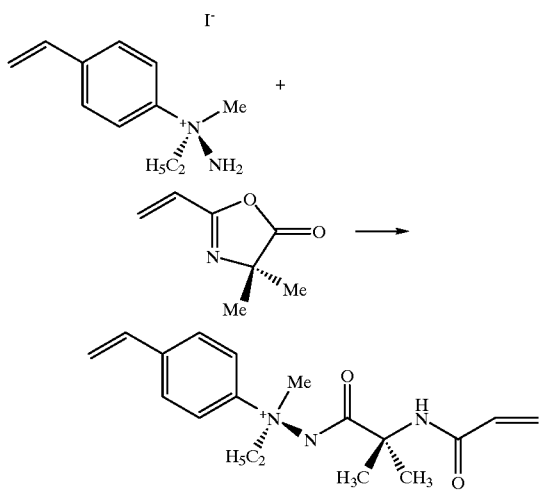

3.18 g (0.01 mol) of (S)-1-methyl-1-ethyl-1-p-vinyl-benzylhydrazinium iodide, prepared from p-vinylbenzyl chloride and 1-methyl-1-ethylhydrazine using standard alkylation conditions, and isolated as the (S)-enantiomer by the method of Singh (103 *J. Chem. Soc.* 604 (1913)), were added to 75 ml of anhydrous t-butanol. The mixture was stirred under nitrogen and 1.12 g (0.01 mol) of potassium t-butoxide was added. The mixture was stirred for 24 hours at room temperature and the reaction mixture was diluted with 75 ml of anhydrous THF, cooled in an ice bath and 1.39 g (0.01 mol) of 2-vinyl-4,4-dimethylazlactone in 50 ml of THF were then added over a 15-min. period. When addition was complete, the mixture was allowed to warm to room temperature and stirred at room temperature for 6 hours. The solvent was stripped under aspirator vacuum on a rotary evaporator to yield 3.0 g (92%) of crude monomer. The product was recrystallized from ethyl acetone at −30° C. to yield pure crystalline momomer, useful for fabricating crosslinked chiral gels, beads, membranes and composites for chiral separations, particularly for operation at high pH. NMR (CDCl$_3$) chemical shifts, presence of vinyl groups in 6 ppm region, vinyl splitting patterns, peak integrations and D$_2$O experiments diagnostic for structure. FTIR absence of azlactone CO band in 1820 cm$^{-1}$ region.

15. EXAMPLE

Functionalization of Silica with an Oxazolone Followed by Conversion to a Chiral Aminimide Useful in the Resolution of Racemic Carboxylic Acids

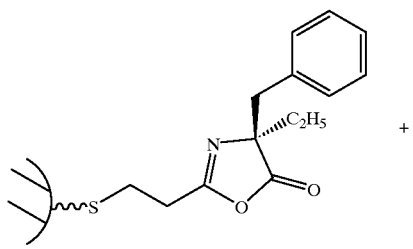

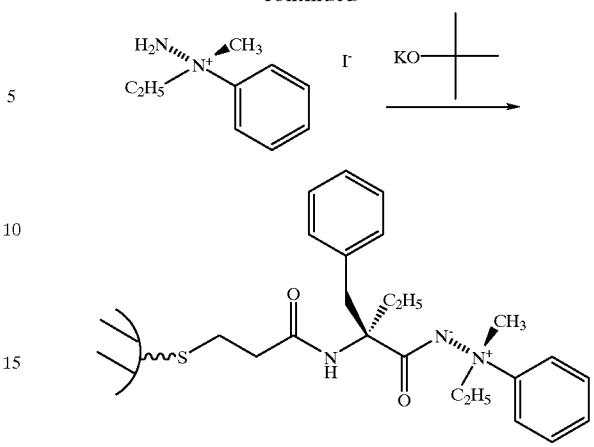

2.81 g (0.01 mol) of (S)-1-methyl-1-ethyl-1-phenyl-hydrazinium iodide, prepared by the method of Singh (103 *J. Chem Soc.* 604 (1913)), was added to 100 ml anhydrous t-butanol. The mixture was stirred under nitrogen and 1.12 g (0.01 mol) potassium t-butoxide was added. The mixture was stirred for 24 hours at room temperature, after which the reaction mixture was diluted with 100 ml anhydrous THF. To this mixture was added 5.0 g silica functionalized with the Michael-addition product of (S)-4-ethyl-4-benzyl-2-vinyl-5-oxazolone to mercaptopropyl-functional silica. This mixture was stirred at room temperature for 8 hours. The functionalized silica was collected by filtration and successively reslurried and refiltered using 100-ml portions of toluene (twice), methanol (four times) and water (twice). The resulting wet cake was dried in a vacuum oven at 60° C. under 30" vacuum to constant weight, yielding 4.98 g of chiral-aminimide-functionalized silica, useful for the separation of racemic mixtures of carboxylic acids, such as ibuprofen, ketoprofen and the like.

16. EXAMPLE

Functionalization of Silica with a Chiral Aminimide for Use in the Separation of Mandelates

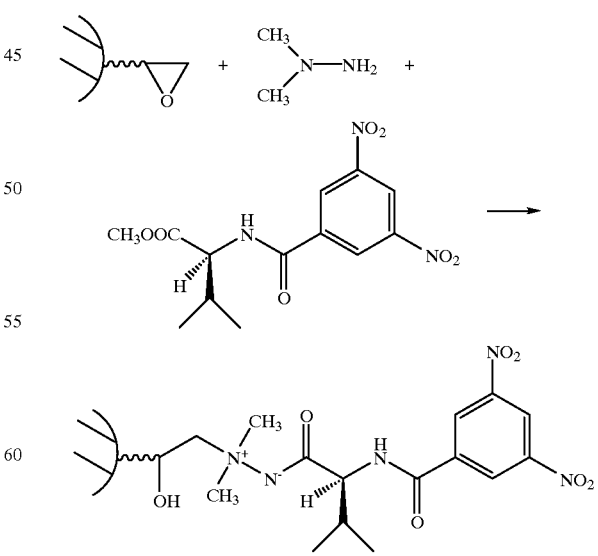

10.0 g epoxy silica (15μ Exsil C-200 silica) was slurried in 75 ml methanol and shaken to uniformly wet the surface.

To this slurry was added 6.01 g (0.01 mol) 1,1-dimethylhydrazine, and the mixture was allowed to stand at room temperature with periodic shaking for 45 min. 32.5 g (0.1 mol) of (S)-3,5-dinitrobenzoylvaline methyl ester was added and the mixture was allowed to stand at room temperature with periodic shaking for three days. The functionalized silica was then collected by filtration, re-slurried in 100 ml methanol and re-filtered a total of five times, then dried in a vacuum oven at 60° C./30" overnight to give 9.68 g of the product. This functionalized silica was slurry packed from methanol into a 0.46×15 cm stainless steel column and used to separate mixtures of mandelic acid derivatives under standard conditions.

Preparation of Epoxy Silica 50 g of 5μ C-200 Exsil silica (SA 250 μ²/g) was added to 650 ml toluene in a two-liter three-necked round-bottomed flask equipped with a Teflon paddle stirrer, a thermometer and a vertical condenser set up with a Dean-Stark trap through a claisen adaptor. The slurry was stirred, heated to a bath temperature of 140° C. and the water was azeotropically removed by distillation and collection in the Dean-Stark trap. The loss in toluene volume was measured and compensated for by the addition of incremental dry toluene. 200 g of glycidoxypropyl trimethoxysilane was added carefully through a funnel and the mixture was stirred and refluxed overnight with the bath temperature set at 140° C. The reaction mixture was then cooled to about 40° C. The resulting functionalized silica was collected on a Buechner filter, washed twice with 50 ml toluene, sucked dry, reslurried in 500 ml toluene, refiltered, reslurried in 500 ml methanol and refiltered a total of four times.

The resulting methanol wet cake was dried overnight in a vacuum oven set for 30" at 60° C. to yield 48.5 g of epoxy silica.

Synthesis of N-3,5-Dinitrobenzoyl-(S)-Valine Methyl Ester

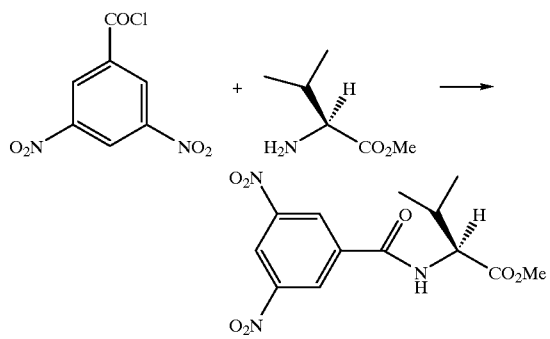

13.12 g (0.1 mol) of (S)-valine methyl ester was added with stirring to a solution of 8 g (0.2 mol) sodium hydroxide in 50 ml of water, cooled to about 10° C., and the mixture stirred at this temperature until complete solubilization was achieved. 23.1 g (0.1 mol) of 3,5-dinitrobenzoylchloride was then added dropwise with stirring, keeping the temperature at 10–15° C. with external cooling. After the addition was complete, stirring was continued for 30 min. To this solution was added over a 10-min. period 10.3 ml (1.25 mol) of concentrated hydrochloric acid, again keeping the temperature at 15° C. After this addition was complete, the reaction mixture was stirred for an additional 30 min. and cooled to 0° C. The solid product was collected by filtration, washed well with ice water and pressed firmly with a rubber dam.

The resulting wet cake was recrystallized from ethanol/water and dried in a vacuum oven under 30" vacuum at 60° C. to yield 28.5 g (90%) of N-3,5-dinitrobenzoyl-(S)-valine methyl ester. NMR ($CDCl_3$): chemical shifts, splitting patterns, integrations and $D_2O$ exchange experiments diagnostic for structure.

17. EXAMPLE

Preparation of Aminimide-Containing Ion-Exchange Silica Matrix

This example describes preparation of an aminimide-functionalized ion-exchange silica matrix using epoxy silica as the support to be modified. The reaction sequence is:

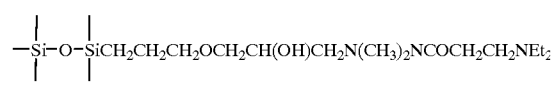

25 g of epoxy silica (15μ Exsil AWP 300 silica, with surface area of 100 m²/g) was slurried in 100 ml methanol until completely wetted by the solvent. 10.2 g of 1,1-dimethylhydrazine were then added with swirling and the mixture allowed to stand at room temperature for 3 hours. 24.7 g of $Et_2NCH_2CH_2COOEt$ were then added and the mixture kept at room temperature with periodic shaking for 2 days.

The diethylaminoethyl (DEAE) functionalized silica was collected by filtration, re-slurried in 100 ml methanol and re-filtered a total of five times. The packing was dried in a vacuum oven at 60° C./30" overnight. A 1.0 ml bed of this material was then packed in a 15 mM NaAc buffer at pH 7.7. The column was then equilibrated with 15 mM NaAc buffer at pH 5.6, and a solution of 1 mg/ml ovalbumin in this buffer run through the bed at a flow rate of 1.6 ml/min. A total of 59.2 ml of protein solution was run.

The column was then washed with 41.7 ml of 15 mM NaAc buffer at pH 5.58 and at a flow rate of 3.9 ml/min. The bound protein was eluted using 23.4 ml of 0.5M NaCl at a flow rate of 3.9 ml/min. The eluent (15.2 ml) was then collected and the transmission of an aliquot measured at 280 mμ with a spectrophotometer. The ovalbumin concentration was determined from a calibration curve. The total amount of ovalbumin collected was 63.7 mg.

18. EXAMPLE

Preparation of Aminimide-Containing Size-Exclusion Silica Matrix

This example describes preparation of an aminimide-functionalized size-exclusion silica matrix using the epoxy silica support described above.

10.0 g of epoxy silica (15μ Exsil C-200 silica, with surface area of 250 m²/g) was slurried in 75 ml of methanol and shaken to uniformly wet the surface. To this slurry was added 10.2 g of 1,1-dimethylhydrazine. The mixture was allowed to stand at room temperature with periodic shaking for 45 min.

15 g of ethyl acetate were then added and the mixture allowed to stand at room temperature with periodic shaking for 3 days. The functionalized silica was then collected by filtration, re-slurried in 100 ml methanol, re-filtered a total of five times and dried in a vacuum oven at 60° C./30"

overnight. The functionalized silica was slurry packed from methanol into a 10 mm interior-diameter jacketed glass column with adjustable pistons to provide an 8 cm-long packed bed. This packing was used to separate mixtures of polyethylene glycol polymers of varying molecular weight with good resolution using a mobile phase.

In a second experiment, the bulk packing was found to selectively adsorb polyethylene-glycol functionalized hemoglobin from serum samples taken from test animals that had been treated with this derivative as a blood substitute. Filtration of the serum, after treatment with the bulk packing, gave a serum free from the functionalized hemoglobin, thus allowing blood screening or testing by means of standard methods.

19. EXAMPLE
Coating of a Silica Matrix with Hydroxypropyl Cellulose Functionalized with an Aminimide Hydroxypropylcellulose is mono-functionalized by reaction, under strong alkaline conditions (preferably provided by a strong base, such as potassium t-butoxide) with $ClCH_2CON^-N^+(CH_3)_3$. The result is replacement of approximately one hydroxyl group in each saccharide unit with the aminimide as follows:

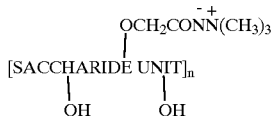

The resulting aminimide derivative is coated onto a surface (e.g., silica). Upon heating to 140° C., the $N(CH_3)_3$ group leaves, resulting in formation of an isocyanate moiety:

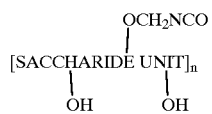

The isocyanate groups then react with unreacted hydroxyl groups on the saccharide units to produce a cross-linked coating.

Alternatively, the cellulose can be coated onto the surface and immobilized using standard techniques (e.g., reaction with bisoxiranes), and then mono, di- or tri-substituted with desired aminimide derivatives as described above.

The foregoing reaction sequence can also be employed with polymers or oligomers bearing NH or SH groups instead of hydroxyl groups and can also be utilized to fabricate structures such as crosslinked cellulose membranes.

20. EXAMPLE
Coating of a Silica Matrix Via Polymerization of an Aminimide on the Matrix This example illustrates an alternative immobilization technique, namely, polymerizing aminimide precursors containing vinyl groups and which have been coated onto a surface. The chemistry resembles the approach described above, except polymerization forms a sturdy shell around an existing support rather than creating a solid block of material.

This sequence makes use of the reaction described above. An epoxide,

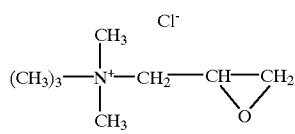

is combined with methyl methacrylate and dimethylhydrazine as set forth in 2.a above to form $CH{=}C(CH_3)$—CO—$NN(CH_3)_2$—$CH_2$—$CH(OH)$—$CH_2$—$N^+(CH_3)_3Cl$. 3.11 g of this material and 0.598 g n-methylol acrylamide were dissolved in 75 ml of methanol, and 3.54 ml of water were then added. To this solution were added 15 g of epoxy silica (15μ Exsil AWP 300 silica, with surface area of 100 m²/g).

The mixture was stirred in a rotary at room temperature for 15 min and then stripped using a bath temperature of 44° C. to a volatiles content of 15% as measured by weight loss (from 25–200° C. with a sun gun). The coated silica was slurried in 100 ml of isooctane containing 86 mg of VAZO-64 dissolved in 1.5 ml toluene which had been de-aerated with nitrogen. The slurry was thoroughly de-aerated with nitrogen and then stirred at 70° C. for two hours.

The coated silica was collected by filtration and washed three times in 100 ml methanol and air dried. The silica was heated at 120° C. for 2 hours to cure the coating. 13.1 g of coated silica were obtained. A 1 ml bed of this material was packed in an adjustable glass column and successfully used to separate BSA from lactoglobulin.

21. EXAMPLE
Preparation of Silica Support Containing Crosslinked Aminimide Polymer Chains In this example, an epoxy-functionalized surface is reacted with disubstituted hydrazine, a bisepoxide and a triester to form a crosslinked network of aminimide chains attached covalently to the surface as follows:

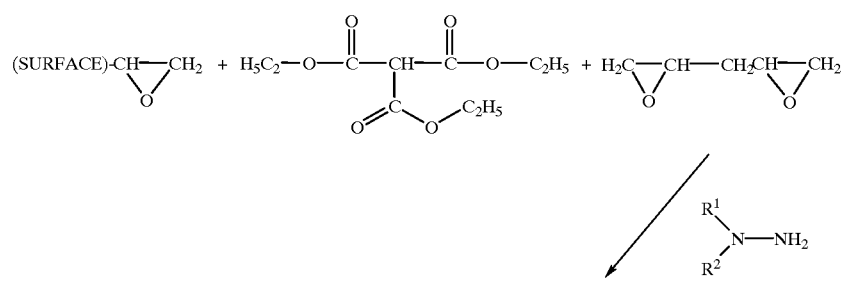

-continued

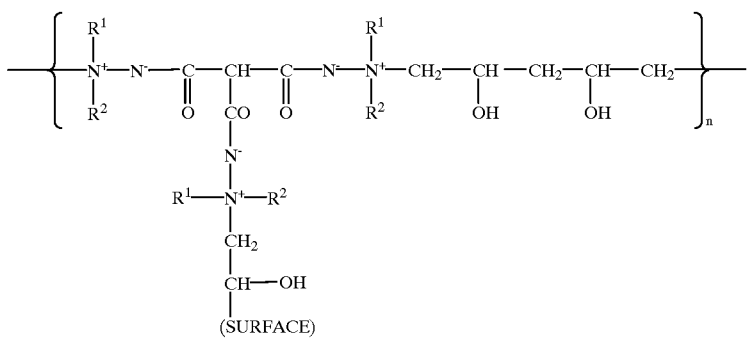

The reaction can be carried out in water at room temperature without special conditions.

22. EXAMPLE
Preparation of Cross-Linked Porous Aminimide Ion-Exchange Beads

This example describes preparation of three-dimensional cross-linked porous copolymeric aminimide ion-exchange beads. It involves reaction of three monomers:

Monomer A: $CH_2=CH-CON^-N^+(CH_3)_3$
Monomer B: $CH_2=C(CH_3)-CON^-N^+(CH_3)_2-CH_2-CH(OH)-CH_2-N^+(CH_3)_3Cl$
Crosslinker: $CH_2=CH-CO-NH-C(CH_3)_2-CON^-N^+(CH_3)_2-CH_2-Ph-CH=CH_2$ where Ph is phenyl.

Preparation of Monomer A: This monomer was prepared according to the method described in 21 *J. Polymer Sci., Polymer Chem. Ed.* 1159 (1983).

Preparation of Monomer B: 30.3 g (0.2 mol) of glycidyltrimethylammonium chloride was dissolved in 100 ml of methanol and filtered free of insolubles. 22 g (0.22 mol) of methyl methacrylate was added thereto, followed by 12 g (0.2 mol) of 1,1-dimethylhydrazine. The solution grew warm and turned slightly pink. It was allowed to stand for 6 days at room temperature, and was then treated with charcoal, filtered, and concentrated on a rotary evaporator at 55° C. and 10 mm to produce a thick lavendar-colored, viscous material. This material was triturated with diethylether and hot benzene and dissolved in the minimum amount of methanol. The mixture was then treated with charcoal, filtered, heated to boiling and brought to the cloud point with ethyl acetate. The resulting solution was allowed to stand at 0° C. for a week. The white crystals that formed were collected by filtration, washed with cold ethyl acetate and dried in a vacuum oven at room temperature to yield 7.3 g of monomer B.

Preparation of Monomer C: 18 g (0.3 mol) of 1,1-dimethylhydrazine was dissolved in 50 ml $CH_2Cl_2$ and cooled in an ice bath with stirring. 41.7 g (0.3 mol) of vinylazlactone in 50 ml $CH_2Cl_2$ were added slowly to keep the temperature below 5° C. The clear solution was stirred and allowed to come to room temperature over 1 hour (resulting in formation of a white solid) and was stirred at room temperature for an additional 1.5 hours. The white solid was collected by filtration, re-slurried in 100 ml $CH_2Cl_2$ and re-filtered. It was then dried in a vacuum oven at room temperature overnight to yield a total of 26.81 g of the intermediate $CH_2=CH-CO-NH-C(CH_3)_2-CO-NH-N-(CH_3)_2$. 10.0 g (0.05 mol) of this intermediate and 7.66 g (0.05 mol) of vinyl benzyl chloride were dissolved in a mixture of 50 ml ethanol and 50 ml $CH_3CN$. The solution was refluxed for 4 hours under a nitrogen stream. It was then cooled to room temperature and concentrated on a rotary evaporator at 55° C. to produce a thick yellow oil. The oil was triturated three times with diethylether to yield 17.08 g of an off-white solid. This solid was dissolved in 100 ml of hot methanol and filtered through a celite pad to remove a small amount of gelatinous material, and the clear filtrate was stripped to yield 10.0 g of Monomer C as a white solid.

Polymerization: 1ml of the emulsifier Span 80 and 175 ml of mineral oil were introduced into a 500 ml round-bottomed flask equipped with stirrer and a heating bath. The mixture was mechanically stirred at 70 RPM and brought to a temperature of 55° C. 40.5 g of monomer A, 7.2 g of monomer B and 5.7 g of the cross-linker were dissolved in 100 ml of demineralized water and heated to 55° C. To this solution were added 150 mg of ammonium persulfate, and the mixture was then poured into the stirred mineral oil. The agitation was adjusted to produce a stable emulsion with an average droplet diameter of approximately 75μ (as determined with an optical microscope).

After 15 min, 0.15 ml of TMED was added and stirring was continued for an additional 45 min. The reaction mixture was cooled and allowed to stand overnight. The supernatant mineral oil phase was removed by aspiration and the beads were collected by decantation. The beads were washed three times with a 0.05% solution of Triton X-100 in demineralized water to remove any remaining mineral oil and then washed with water and allowed to settle. The water was removed by decantation.

This procedure was repeated a total of five times. The beads obtained at the conclusion of the foregoing steps had a mean diameter of approximately 75μ and an ion-exchange capacity of 175 μeq/ml.

23. EXAMPLE
Preparation of an Aminimide-Based Electrophoretic Gel

This example describes preparation of an aminimide electrophoresis gel. As a control, the standard Sigma protein electrophoresis mix (available from Sigma Chemical Co., St. Louis, Mo.) was run on an acrylamide/methylene bisacrylamide linear gradient gel prepared using a gradient maker with 5% and 12.5% monomer solutions, as shown below. The gel was overlayed with isobutanol and allowed to polymerize overnight.

| Monomer | 5% Monomer | 12.5% |
|---|---|---|
| Lower Tris | 5.0 ml | 5.0 ml |
| H$_2$O | 11.7 ml | 4.7 ml |
| 30% Acrylamide | 3.3 ml | 8.3 ml |
| Glycerol | — | 2.0 ml |
| Ammonium Persulfate | 30 µl | 30 µl |
| TMED | 15 µl | 15 µl |

Lower Tris 1.5M: 6.06 g Tris base, 8 ml 10% SDS, volume adjusted to 90 ml with double-distilled water. The pH was adjusted to 6.0 with concentrated HCl, and the final volume adjusted to 100 ml with DD water.

Acrylamide 30% w/v: 29.2 g acrylamide, 0.8 g of methylene bisacrylamide and 100 ml DD water.

SDS 10% w/v: 10 g of SDS dissolved in DD water and adjusted to a volume of 100 ml.

Ammonium persulfate 10%: 0.1 g ammonium persulfate was dissolved in 0.9 ml DD water. The solution was used within 4 hours of preparation.

TMED: used directly as obtained from Sigma Chemical Co., St. Louis, Mo., under the tradename TMEDA.

A second gel was prepared by replacing the acrylamide with an equal weight of the aminimide monomer $CH_2=CH-CO-N-N(CH_3)_3$ and the protein standard was run in the same way as the first.

Separation of proteins with the aminimide gel were equivalent to the acrylamide gel, but the aminimide gel produced Rf (i.e., the ratio of distance traversed by a particular protein to the distance traversed by the solvent front) levels approximately 20% higher than those of the acrylamide gel.

24. EXAMPLE
Preparation of Aminimide-Based Latex Particles

This example describes preparation of latex particles containing an aminimide comonomer.

591.1 ml of distilled water was charged to a three-necked round-bottomed flask. A nitrogen dip tube was placed below the liquid level and the nitrogen flow rate set to 2 cm$^3$/min. The solution was mechanically agitated with a Teflon paddle at 250 RPM and heated to 80 ° C. over a half-hour period. In a separate flask were dissolved 121.6 g of butyl acrylate, 54.6 g of ethyl acrylate, 13.0 g of acrylic acid, 9.97 g of methyl methacrylate, 59.7 g of the aminimide monomer $CH_2=CH-CO-N-N(CH_3)_2-CH_2-CH_2-OH$ and 0.92 g of Aerosol TR-70 so as to obtain solution without exceeding a temperature of 25° C. When completely dissolved, 1.53 g of additional TR-70 were added and the mixture was then stirred until solution was achieved.

20.7 ml of distilled water was purged with nitrogen for 10 min and 1.59 g of K$_2$S$_2$O$_8$ is dissolved in it. This persulfate solution was added to the heated water in the reaction flask after it stabilized at 80° C. The nitrogen dip tube was raised and a nitrogen blanket was maintained. The monomer mix was pumped in at a steady, calibrated rate such that the constant addition took exactly 4 hours. When addition was complete, the latex was post-heated at 80° C. for 1 hour, cooled to 25° C. and titrated to pH 5.0 by dropwise addition of triethylamine (approximately 20 cm$^3$) over 20 min with agitation. The latex was then filtered through cheese cloth and stored. Average particle size was measured at about 0.14µ.

It should be apparent to those skilled in the art that other compositions and processes for preparing the compositions not specifically disclosed in the instant specification are, nevertheless, contemplated thereby. Such other compositions and processes are considered to be within the scope and spirit of the present invention. Hence, the invention should not be limited by the description of the specific embodiments disclosed herein but only by the following claims.

What is claimed is:

1. A composition having the structure

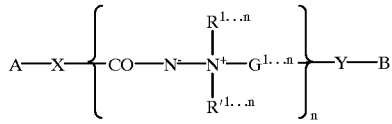

wherein
  a. A and B are the same or different, and each is a chemical bond; hydrogen; an electrophilic group; a nucleophilic group; R; an amino acid derivative; a nucleotide derivative; a carbohydrate derivative; a reporter element; an organic moiety containing a polymerizable group; or a macromolecular component, wherein A and B are optionally connected to each other or to other structures and R is as defined below;
  b. X and Y are the same or different and each represents a chemical bond or one or more atoms of carbon, nitrogen, sulfur, oxygen or combination thereof;
  c. R and R' are the same or different and each is an alkyl, cycloalkyl, aryl, aralkyl or alkaryl group or a substituted or heterocyclic derivative thereof, wherein R and R' may be different in adjacent n units and have a selected stereochemical arrangement about the nitrogen atom to which they are attached;
  d. G is a chemical bond or a connecting group that includes a terminal carbon atom for attachment to the quaternary nitrogen and G may be different in adjacent n units; and
  e. n≧2;

provided that if G is a chemical bond, Y includes a terminal carbon atom for attachment to the quaternary nitrogen.

2. The composition of claim 1 wherein G includes at least one of an aromatic ring, a heterocyclic ring, a carbocyclic moiety, an alkyl group or substituted derivatives thereof.

3. The composition of claim 1 wherein at least one of R and R' includes a hydroxyl containing substituent.

4. The composition of claim 1 wherein A and B are the same.

5. The composition of claim 1 where R and R' are different so that the composition is chiral.

6. The composition of claim 1 wherein at least one of A and B is a terminal-structural moiety of formula T-U, wherein:
  a. U is selected from the group consisting of aliphatic chains having from 2 to 6 carbon atoms, substituted or unsubstituted aryl, substituted or unsubstituted cycloalkyl, and substituted or unsubstituted heterocyclic rings; and
  b. T is selected from the group consisting of —OH, —NH$_2$, —SH, (CH$_3$)$_3$N$^+$—SO$_3$, —COO, CH$_3$, H and phenyl.

7. The composition of claim 1 wherein at least one of A and B is HO—CH$_2$—(CHOH)$_n$—.

8. The composition of claim 1 wherein A and B are part of the same cyclic moiety.

9. The composition of claim 1 in the form of:
  (A) a peptide mimetic wherein at least one of A and B is an amino acid derivative of the form (AA)$_m$ where AA is a natural or synthetic amino acid residue and m is an integer;

(B) a nucleotide mimetic wherein at least one of A and B is a nucleotide derivative of the form $(NUCL)_1$, wherein 1 is an integer, such that $(NUCL)_1$ is a natural or synthetic nucleotide when 1=1, nucleotide probe when 1=2–25 and an oligonucleotide when 1>25 including both deoxyribose (DNA) and ribose (RNA) variants;

(C) a carbohydrate mimetic wherein at least one of A and B is a natural carbohydrate, a synthetic carbohydrate residue or derivative thereof or a related organic acid thereof;

(D) a pharmaceutical compound wherein at least one of A and B is an organic structural motif of the organic compound which is obtained from a pharmaceutical compound, a pharmacophore or metabolite thereof and has specific binding properties to a ligand;

(E) a reporter compound wherein at least one of A and B is a reporter element of a natural or synthetic dye or a photographically active residue which possess reactive groups of an amino, thio, hydroxy, carboxylic acid, acid chloride, isocyanate alkyl halide, aryl halide or an oxirane group, which may be synthetically incorporated into the aminimide structure or reaction scheme and may be attached through the groups without adversely interfering with the reporting functionality of the group;

(F) a polymerizable compound wherein at least one of A and B is an organic moiety containing a polymerizable group of a vinyl group, oxirane group, carboxylic acid, acid chloride, ester, amide, lactose or lactam; or (G) a substrate wherein at least one of A and B is a macromolecular component of a surface or structure which is attached to the aminimide module via a reactive group in a manner where the binding of the attached species to a ligand-receptor molecule is not adversely affected and the interactivity of the attached functionality is determined or limited by the macromolecule, said macromolecule component having a molecular weight of at least about 1000 Daltons or being in the form of a ceramic particle, a nanoparticle, a latex particle, a porous or non-porous beads, a membrane, a gel, a macroscopic surface or a functionalized or coated version or composite thereof.

* * * * *

UNITED STATES PATENT AND TRADEMARK OFFICE
CERTIFICATE OF CORRECTION

PATENT NO. : 5,981,467

DATED : November 9, 1999

INVENTOR : Joseph C. Hogan, Jr.

It is certified that error appears in the above-identified patent and that said Letters Patent is hereby corrected as shown below:

On the title page at [73] Assignee: change "Arqule" to --ArQule--.

In column 72, line 26: change "combination" to --combinations--.

Signed and Sealed this

Sixteenth Day of May, 2000

*Attest:*

Q. TODD DICKINSON

*Attesting Officer*     *Director of Patents and Trademarks*